United States Patent [19]

Nagata et al.

[11] Patent Number: 5,616,586
[45] Date of Patent: Apr. 1, 1997

[54] TRICYCLIC QUINOXALINEDIONES

[75] Inventors: Ryu Nagata, Kyoto; Norihiko Tanno, Ibaraki; Toru Kodo, Osaka, all of Japan

[73] Assignee: Sumitomo Pharmaceuticals Company, Limited, Osaka-fu, Japan

[21] Appl. No.: 211,314

[22] PCT Filed: Oct. 22, 1992

[86] PCT No.: PCT/JP92/01375

§ 371 Date: Apr. 1, 1994

§ 102(e) Date: Apr. 1, 1994

[87] PCT Pub. No.: WO93/08188

PCT Pub. Date: Apr. 29, 1993

[30] Foreign Application Priority Data

Oct. 23, 1991 [JP] Japan .................. 3-305456

[51] Int. Cl.⁶ ............ A61K 31/495; C07D 471/06; C07D 487/06; C07D 215/48
[52] U.S. Cl. .............. 514/250; 544/344; 546/165; 546/168
[58] Field of Search .............. 544/344; 514/250

[56] References Cited

U.S. PATENT DOCUMENTS

| | | | |
|---|---|---|---|
| 3,296,267 | 1/1967 | Ross | 260/250 |
| 3,813,392 | 5/1974 | Sellstedt et al. | 260/250 R |
| 3,992,378 | 11/1976 | St. Clair | 260/250 |
| 4,075,206 | 2/1978 | Holmes | 260/250 Q |

FOREIGN PATENT DOCUMENTS 9015058 12/1990 WIPO.

OTHER PUBLICATIONS

Brodie, The Lancet 341, 1445 (1995).
Organic Syn. Collected vol. I, pp. 12–13 (1955).
Mareh, "Advanced Organic Chemistry", 4th Ed. p1200 (1989).
Rundfelt, Brain Res. 653, 125 (1994).
Meldrum, "Glutanate Antagonists is Potential Antepileptic Agents", Nov. 11, 1995 Symposium on Pre and Post Synoptic Modulation (San Diego).
Kemp, Tips, 14, 20 (1993.
McCabe J Pharm Exper. Therapeutics 264, 1248 (1993).
Leeson, J. Med Chem 37, 4053 (1994).
Chapman, Neurology and Neurobiology 46, 204–205 (1988).
Wasterlane Neurology 43, 2303 (1993).
G. W. Albers, Clinical Neuropharmacology, vol. 13, No. 3, pp. 177–197, 1990.
Richardson et al. (1959) J. Org. Chem. 25:1138–47.
Pellegrini–Giampietro et al. (1989) Br. J. Pharmacol. 98:1281–86.
Sheardown et al. (1989) Eur. J. of Pharmacology 174:197–204.
Yoneda et al. (1989) Biochem. and Biophys. Research Comm. 164(2):841–49.
Sheardown et al. (1990) Science 247:571–74.
A. Richardson (1965) Journal of Organic Chemistry 30(8):2589–93.
Lipton et al., The New England Journal of Medicine, vol. 330, No. 9, pp. 613–622, Mar., 1994.
McCabe et al., The Journal of Pharmacology and Experimental Therapeutics, vol. 264, No. 3, pp. 1248–1252, 1993.
Leeson et al., Journal of Medicinal Chemistry, vol. 37, No. 24, pp. 4053–4067, Nov. 1994.
Nagata et al., J. Med. Chem. vol. 37, No. 23, pp. 3956–3968, 1994.
J. Grotta, 19th International Joint Conference on Stroke and Cerebral Circulation, para. 52, p. 255. (1960).
Takizawa et al., Journal of Cerebral Blood Flow and Metabolism, vol. 11, No. 5, pp. 786–793, 1991.
Dr. Eckard Weber, "Antagonists at the Glycine Coagonist Site of the NMDA Receptor: In Vivo Efficacy Profiles in Animal Models of Stroke", New Strategies to Prevent Neural Damage From Ischemic Stroke, Oct. 27–28, 1994.
Gill et al., Journal of Cerebral Blood Flow and Metabolism, vol. 11, Suppl. 2, 1991.
Kristensen et al., Pain, vol. 51 No. 2, 1992.
James McCullough, Br. J. clin. Pharmac., 34, pp. 106–114, 1992.
Ferkany et al., The Journal of Pharmacology and Experimental Therapeutics, vol. 264, No. 1, pp. 256–264, 1993.

Primary Examiner—Mark L. Berch
Attorney, Agent, or Firm—Birch, Stewart, Kolasch & Birch, LLP

[57] ABSTRACT

Tricyclic quinoxalinediones of the formula:

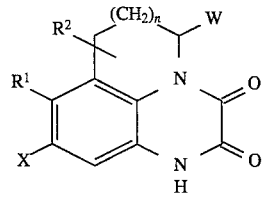

wherein X is alkyl, halogen, cyano, trifluoromethyl, nitro, hydroxy, amino, etc.; $R^1$ is H, etc.; $R^2$ is H, alkyl, cycloalkyl, alkenyl, alkynyl, cycloalkylalkyl, arylalkyl, substituted arylalkyl, aryl, or substituted aryl; W is H, $CO_2R^3$, $CO_2Y$, $CONR^3R^4$, $CONR^3Y$, $CON(OR^3)R^4$, $COR^3$, CN, tetrazolyl, or substituted alkyl; $R^3$ and $R^4$ independently are H, alkyl, cycloalkyl, alkenyl, alkynyl, etc.; Y is mono-substituted alkyl or di-substituted alkyl; and n is an integer 0 or 1, or a pharmaceutically acceptable salt thereof, which are useful as a selective antagonist of glutamate receptor for the treatment or prevention of various diseases in animals including human being, for example, minimizing damage of central nervous system induced by ischaemic or hypoxylic conditions, treatment and/or prevention of neurodegenerative disorders, and further analgesics, antidepressants, anxiolitics, and anti-schizophrenics.

7 Claims, No Drawings

TRICYCLIC QUINOXALINEDIONES

This application is a 371 of PCT/JP92/01375, filed Oct. 22, 1992.

TECHNICAL FIELD

This invention relates to a new class of tricyclic quinoxalinediones which are selective antagonists of glutamate receptors such as NMDA (N-methyl-D-aspartate) receptors and AMPA (2-amino-3-hydroxy-5-methyl-4-isoxazolepropionic acid) receptors. Particularly, the compounds provided by the present invention antagonize the action of glycine at strychnine-insensitive glycine modulatory site of NMDA receptors and therefore, are especially useful for minimizing damage of central nervous system induced by ischaemic or hypoxylic conditions such as stroke, hypoglycaemia, cardiac arrest, and physical trauma, (see, J. McCulloch, Br. J. clin. Pharmacol., 34, 106 (1992)). The compounds are also useful in treatment of a number of neurodegenerative disorders including epilepsy, Huntington's chorea, Parkinson's disease, and Alzheimer's disease (reviews: G. Johnson, Annu. Rep. Med. Chem., 24, 41 (1989) and G. Johson and C. F. Bigge, ibid., 26, 11, (1991)). The present compounds may also have analgestic, antidepressant, anxiolitic, and anti-schizophrenic activities, by virtue of these NMDA-glycine antagonism, as indicated by recent reports, e.g. A. H. Dickenson and E. Aydar, Neuroscience Lett., 121,263 (1991), R. Trullas and P. Skolnick, Eur. J. Pharmacol., 185, 1 (1990), J. H. Kehne, et al., Eur. J. Pharmacol., 193,283 (1991) P. H. Hutson, et al., Br. J. Pharmacol., 103, 2037 (1991), in which the reagents affecting glycine-binding site of NMDA receptors have shown such activities. Excessive release of glutamic acid and/or glycine from synaptosome results in overexcitation of NMDA receptor-$Ca^{2+}$ channel complexes and successive massive amount of $Ca^{2+}$ influx into the cell, which leads to neuronal cell death. NMDA-glycine antagonist described in the present invention would obviously regulate the amount of $Ca^{2+}$ influx from the glycine modulatory site of NMDA receptor-channel complex to maintain normal activities of neuronal cell. Therefore, the compounds of the present invention may be potential therapeutic agents for any diseases of animals including human caused by excessive glutamic acid and/or glycine release in addition to the diseases indicated above.

BACKGROUND ART

Nonsubstituted tricyclic quinoxalinediones, 6,7-dihydro-1H, 5H-pyrido[1,2,3-de]quinoxaline-2,3-dione and 5,6-dihydro-1H-pyrrolo[1,2,3-de-quinoxaline-2,3-dione are described in A. Richardson, JR. and E. D. Amstutz, J. Org. Chem., 25 1138 and A. Richardson, JR., ibid., 25, 2589 (1965), respectively. Amine-substituted tricyclic quinoxalinedione,6,7-dihydro-6-(di-n-propylamino)-1H, 5H-pyrido[1,2,3,-de]quinoxaline-2,3-dione is disclosed in WO 90/15058, and M. W. Moon, et al., J. Med. Chem., 35, 1076 (1992) as an example of series of imidazoquinolinones and related compounds having dopaminergic and serotonergic activities, and especially, as a selective and potent $D_2$ agonist. The compound described there would not be expected to exhibit antagonistic activities of glutamate receptors, since, to date, none of compounds possessing cross affinities to both glutamate and dopamine receptors have been appeared.

Certain quinoxalinediones and benzo[1,2-f]qunoxalinediones have been shown to have antagonist activities against glutamate receptors including glycine modulatory site of NMDA receptors and AMPA receptors (For example, D. E. Pellegrini-Giampietro, et al., Br. J. Pharmacol., 98, 1281 (1989), M. J. Sheardown, et al., Eur. J. Pharmacol., 174, 197 (1989), Y. Yoneda and K. Ogita, Biochem. Biophys. Res. Commun., 164, 841 (1989), and M. J. Sheardown, et al., Science, 247, 571 (1990)).

DISCLOSURE OF INVENTION

The present invention provides novel quinoxalinediones depicted by formula 1 and pharmaceutically acceptable salts thereof:

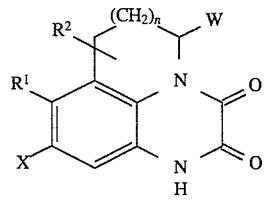

wherein

X represents alkyl, halogen, cyano, trifluoromethyl, nitro, hydroxy, amino, alkylamino, alkoxy, alkanoyl, alkoxycarbonyl, sulfamoyl, carbamoyl, alkylcarbamoyl, alkylthio, alkylsulfinyl, alkylsulfonyl, alkylsulfamoyl, alkylsulfonyl amino, or acylamino;

$R^1$ represents hydrogen, alkyl, halogen, cyano, trifluoromethyl, nitro, hydroxy, amino, alkylamino, alkoxy, alkanoyl, alkoxycarbonyl, sulfamoyl, carbamoyl, alkylcarbamoyl, alkylthio, alkylsulfinyl, alkylsulfonyl, alkylsulfamoyl, alkylsulfonylamino, or acylamino;

$R^2$ represents hydrogen, alkyl, cycloalkyl, alkenyl, alkynyl, cycloalkylalkyl, arylalkyl, substituted arylalkyl, aryl, or substituted aryl;

W represents hydrogen, $CO_2R^3$, $CO_2Y$, $CONR^3R^4$, $CONR^3Y$, $CON(OR^3)R^4$, $COR^3$, CN, tetrazolyl, or substituted alkyl;

$R^3$ and $R^4$ independently represent hydrogen, alkyl, cycloalkyl, alkenyl, alkynyl, cycloalkylalkyl, arylalkyl, substituted arylalkyl, aryl, substituted aryl, heteroarylalkyl, heteroaryl, substituted heteroaryl, substituted heteroarylalkyl or heterocyclic;

Y represents mono-substituted alkyl or di-substituted alkyl; and n is an integer 0 or 1.

The term "alkyl" as used herein includes straight-chained or branched alkyl groups containing from 1 to 6 carbon atoms. Typical examples are methyl, ethyl, n-propyl, isopropyl, sec-butyl, tert-butyl, neopentyl, n-pentyl, and n-hexyl.

The term "halogen" as used herein includes fluorine, chlorine, bromine, and iodine. Typical examples are chlorine and bromine.

The term "alkoxy" as used herein includes straight-chained or branched alkoxy groups containing from 1 to 6 carbon atoms. Typical examples are methoxy, ethoxy, propoxy, isopropoxy, sec-butoxy, tert-butoxy, neopentoxy, pentoxy, and hexoxy.

The term "alkanoyl" as used herein includes straight-chained or branched alkanoyl groups containing from 1 to 6 carbon atoms. Typical examples are formyl, acetyl, propanoyl, n-butanoyl, and pivaloyl.

The term "alkoxycarbonyl" as used herein includes straight-chained or branched alkoxycarbonyl groups containing from 1 to 6 carbon atoms. Typical examples are methoxycarbonyl, ethoxycarbonyl, propoxycarbonyl, isopropoxycarbonyl, sec-butoxycarbonyl, and tert-butoxycarbonyl.

The term "alkylthio" as used herein includes straight-chained or branched alkylthio groups containing from 1 to 6 carbon atoms. Typical examples are methylthio, ethylthio, n-propylthio, isopropylthio, sec-butylthio, tert-butylthio, neopentylthio, n-pentylthio, and n-hexylthio.

The term "alkylsulfinyl" as used herein includes straight-chained or branched alkylsulfinyl groups containing from 1 to 6 carbon atoms. Typical examples are methylsulfinyl, ethylsulfinyl, n-propylsulfinyl, isopropylsulfinyl, sec-butylsulfinyl, tert-butylsulfinyl, neopentylsulfinyl, n-pentylsulfinyl, and n-hexylsulfinyl.

The term "alkylsulfonyl" as used herein includes straight-chained or branched alkylsulfonyl groups containing from 1 to 6 carbon atoms. Typical examples are methylsulfonyl, ethylsulfonyl, n-propylsulfonyl, isopropylsulfonyl, sec-butylsulfonyl, tert-butylsulfonyl, neopentylsulfonyl, n-pentylsulfonyl, and n-hexylsulfonyl.

The term "alkylcarbamoyl" as used herein includes mono- and dialkylcarbamoyl, wherein an alkyl moiety contains from 1 to 6 carbon atoms which may be straight-chained or branched. Typical examples are methylcarbamoyl, methylethylcarbamoyl, diethylcarbamoyl, propylcarbamoyl, diisopropylcarbamoyl, and hexylcarbamoyl.

The term "alkylsulfamoyl" as used herein includes sulfamoyl groups substituted with 1 or 2 alkyl groups containing from 1 to 6 carbon atoms which may be straight-chained or branched. Typical examples are methylsulfamoyl, methylethylsulfamoyl, diethylsulfamoyl, propylsulfamoyl, diisopropylsulfamoyl, and hexylsulfamoyl.

The term "alkylsulfonylamino" as used herein includes straight-chained or branched alkylsulfonylamino groups containing from 1 to 6 carbon atoms. Typical examples are methylsulfonylamino, ethylsulfonylamino, n-propylsulfonylamino, isopropylsulfonylamino, sec-butylsulfonylamino, tert-butylsulfonylamino, neopentylsulfonylamino, n-pentylsulfonylamino, and n-hexyisulfonylamino.

The term "acylamino" as used herein includes straight-chained or branched alkanoylamino groups containing from 1 to 6 carbon atoms. The term "acylamino" as used herein also includes aroylamino groups containing from 7 to 11 carbon atoms. Typical examples are formylamino, acetylamino, propanoylamino, butanoylamino, sec-butanoylamino, n-pentanoylamino, n-hexanoylamino, benzoylamino, and 1- or 2-naphthoylamino.

The term "cycloalkyl" as used herein includes cycloalkyl groups containing from 3 to 7 carbon atoms. Typical examples are cyclopropyl, cyclobutyl, cyclopentyl, cyclohexyl, and cycloheptyl.

The term "alkenyl" as used herein includes straight-chained or branched alkenyl groups containing from 2 to 6 carbon atoms. Typical examples are vinyl, allyl, 1-propenyl, and 1-, 2- or 3-butenyl.

The term "alkynyl" as used herein includes straight-chained or branched alkynyl groups containing from 2 to 6 carbon atoms. Typical examples are ethynyl, propargyl, 1-propynyl, butynyl, and pentynyl.

The term "cycloalkylalkyl" as used herein includes straight-chained or branched alkyl groups attached with cycloalkyl groups, which contains up to 13 carbon atoms. Typical examples are cyclopropylmethyl, cyclopentylethyl, cyclohexylmethyl, and cyclohexylpropyl.

The term "arylalkyl" as used herein includes straight-chained or branched alkyl groups attached with aryl groups, which contains up to 15 carbon atoms. Typical examples are benzyl, phenylethyl, 1- or 2-naphthylmethyl, and 1- or 2-naphthylpropyl.

The term "aryl" as used herein includes aryl groups containing up to 10 carbon atoms. Typical examples are phenyl, and 1- or 2-naphthyl.

The term "heteroaryl" as used herein includes 5 or 6 membered heteroaryl groups containing up to 4 nitrogen atoms, and 5 or 6 membered heteroaryl groups containing up to 2 nitrogen atoms, up to 1 oxygen atom, and/or up to 1 sulfur atom. The term "heteroaryl" also includes 5 or 6 membered heteroaryl rings groups containing up to 3 nitrogen atoms, up to 1 oxygen atoms, and or 1 sulfur atom, which are fused with a benzene ring. Typical examples are pyridyl, quinolyl, isoquinolyl, pyridazinyl, pyrimidinyl, pyrazinyl, pyrrolyl, indolyl, pyranyl, furyl, benzofuryl, thienyl, benzothienyl, imidazolyl, oxazolyl, thiazolyl, isoxazolyl, isothiazolyl, oxadiazolyl, thiadiazolyl, tetrazolyl, benzoxazolyl, benzothiazolyl, benzisoxazolyl, benzisothiazolyl, benzimidazolyl, and benzotriazolyl.

The term "heteroarylalkyl" as used herein includes straight-chained or branched alkyl groups containing up to 6 carbon atoms, which is attached to a heteroaryl group, wherein the heteroaryl group is as defined above. Typical examples are pyridylmethyl, quinolylethyl, isoquinolylpropyl, pyridazinylmethyl, pyrimidinylethyl, pyrazinylpropyl, pyrrolylmethyl, indolylethyl, pyranylpropyl, furylmethyl, benzofurylethyl, thienylpropyl, benzothienylmethyl, imidazolylethyl, oxazolylpropyl, thiazolylmethyl, isoxazolylmethyl, isothiazolylethyl, oxadiazolylethyl, thiadiazolylproyl, tetrazolylmethyl, benzoxazolylethyl, benzothiazolylpropyl, benzisoxazolylmethyl, benzisothiazolylethyl, benzimidazolylpropyl, and benzotriazolylmethyl.

The term "heterocyclic" as used herein includes heterocyclic groups containing up to 6 carbon atoms together with 1 or 2 heteroatoms which are selected from nitrogen, oxygen and sulfur atoms. Typical examples are piperidyl, piperazinyl, morpholinyl, tetrahydropyranyl, tetrahydrofuranyl, pyrrolidinyl, and dithianyl. The term "heterocyclic" as used herein also includes heterocyclic groups fused with a benzene-ring wherein the fused rings contain up to 10 carbon atoms together with 1 or 2 heteroatoms which are selected from nitrogen, oxygen and sulfur atoms. Typical examples are indolinyl, isoindolinyl, tetrahydro-1-quinolinyl, and tetrahydro-2-quinolinyl, tetrahydroquinoxalinyl.

The term "alkylamino" as used herein includes mono- and dialkylamino groups, wherein an alkyl group contains from 1 to 6 carbon atoms which may be straight-chained or branched. Typical examples are methylamino, methylethylamino, diethylamino, propylamino, diisopropylamino, and hexylamino.

The alkyl groups of the term both "substituted alkyl" as used in W and "mono-substituted alkyl" as used in Y include straight-chained or branched alkyl groups containing from 1 to 4 carbon atoms. Typical examples are methyl, ethyl, propyl, and butyl.

The substituent of the term "substituted alkyl" as used in W includes $CO_2R^3$, $CO_2Y$, $CONR^3R^4$, $CONR^3Y$, $CON(OR^3)R^4$, $COR^3$, $CN$, $NR^3CO_2R^4$, $NR^3CONR^4R^5$, phthalimido, heteroaryl, substituted heteroaryl, heterocyclic, $NR^3R^4$, $NR^3SO_2R^4$, $NR^3COR^4$, $NR^3COY$, $NR^3COCO_2R^4$, $NR^3COCONR^4R^5$, $NR^3COCOR^4$, $OR^3$, $OCOR^3$, $OCOY$, $OCO_2R^3$, $OCONR^3R^4$, $OCOCO_2R^3$, $OCOCOR^3$, $OCOCONR^3R^4$, $OSO_2R^3$, $PO(OR^3)_2$, $SR^3$, $SOR^3$, $SO_2R^3$, $SO_3R^3$, $SO_2NR^3R^4$, Cl, Br, and I;

wherein $R^3$, $R^4$, and $R^5$ independently represent hydrogen, alkyl, cycloalkyl, alkenyl, alkynyl, cycloalkylalkyl, arylalkyl, substituted arylalkyl, aryl, substituted aryl, heteroarylalkyl, heteroaryl, substituted heteroaryl, substituted heteroarylalkyl or heterocyclic; and Y represents mono-substituted alkyl, or di-substituted alkyl, The substituent of the term "mono-substituted alkyl" as used in Y includes $CO_2R^3$, $CONR^3R^4$, $COR^3$, CN, $NR^3CO_2R^4$, $NR^3CONR^4R^5$, phthalimido, $NR^3R^4$, $NR^3SO_2R^4$, $NR^3COR^4$, $OR^3$, $OCOR^3$, $OCO_2R^3$ and $OCONR^3R^4$;

wherein $R^3$, $R^4$, and R5 are the same as defined above.

The alkyl groups of the term "di-substituted alkyl" as used in Y include straight-chained alkyl groups containing from 1 to 4 carbon atoms. Typical examples are 1,1-disubstituted methyl, 1,1-disubstituted ethyl, 1,2-disubstituted ethyl, and 2,2-disubstituted ethyl.

The substituent of the term "di-substituted alkyl" as used in Y includes independently $CO_2R^3$, $CONR^3R^4$, $COR^3$, CN, $NR^3CO_2R^4$, $NR^3CONR^4R^5$, phthalimido, aryl, substituted aryl, heteroaryl, substituted heteroaryl, heterocycloalkyl, $NR^3R^4$, $NR^3SO_2R^4$, $NR^3COR^4$, $OR^3$, $OCOR^3$, $OCO_2R^3$ and $OCONR^3R^4$;

wherein $R^3$, $R^4$, and $R^5$ are the same as defined above.

The number of the substituents of substituted aryl, substituted arylalkyl, substituted heteroaryl, or substituted heteroarylalkyl, respectively, as used herein may be permitted to be up to 3, and the substituents include alkyl, halogen, cyano, trifluoromethyl, nitro, hydroxy, mercapto, amino, alkylamino, alkoxy, alkanoyl, alkoxycarbonyl, carboxy, sulfamoyl, carbamoyl, alkylcarbamoyl, alkylthio, alkylsulfinyl, alkylsulfonyl, alkylsulfamoyl, alkylsulfonylamino, acylamino, substituted alkyl, substituted alkenyl, and substituted alkynyl;

wherein the alkyl groups of the term "substituted alkyl" include straight-chained or branched alkyl groups containing from 1 to 4 carbon atoms, and the substituent of the term "substituted alkyl" includes amino, alkylamino, alkoxycarbonyl, carboxy, and carbamoyl. Typical examples of "substituted alkyl" are methoxycarbonylmethyl, carboxymethyl, α-ethoxycarbonylethyl, β-ethoxycarbonylethyl, α-carboxyethyl, β-carboxyethyl, aminomethyl, methylaminomethyl, dimethylaminomethyl, α-aminoethyl, β-aminoethyl, α-methylaminoethyl, β-ethylaminoethyl, α-ethylaminoethyl, and carbamoylmethyl. The alkenyl groups of the term "substituted alkenyl" include straight-chained or branched alkenyl groups containing from 2 to 5 carbon atoms, and the substituent of the term "substituted alkenyl" includes amino, alkylamino, alkoxycarbonyl, carboxy, and carbamoyl. Typical examples of "substituted alkenyl" are methoxycarbonylvinyl, carboxyvinyl, α-ethoxycarbonylvinyl, α-carboxyvinyl, 3-aminopropenyl, 3-methylaminopropenyl, 3-diethylaminopropenyl, and 4-carbamoybutenyl. The alkynyl groups of the term "substituted alkynyl" include straight-chained or branched alkynyl groups containing from 2 to 5 carbon atoms, and the substituent of the term "substituted alkynyl" includes amino, alkylamino, alkoxycarbonyl, carboxy, and carbamoyl. Typical examples of "substituted alkynyl" are methoxycarbonylethynyl, carboxyethynyl, 3-amino-1-propynyl, 3-methylamino-1-propynyl, 3-diethylamino-1-propynyl, and 4-carbamoyl-1-butynyl.

The expression "pharmaceutically acceptable salts thereof" represents either non-toxic acid addition salts or base addition salts.

The acid which forms non-toxic salts with the compounds provided by formula 1 include inorganic acid such as hydrochloric, hydrobromic, sulfuric, and phosphoric acid or organic acid such as acetic, oxalic, citric, lactic, tartaric, malonic, fumaric, and maleic acid. On the other hand, the non-toxic base addition salts include inorganic metal salt such as lithium, sodium, potassium, magnesium, aluminum, and barium salt or organic quarternally ammonium salt such as ammonium, triethylammonium, tetrabutylammonium, pyridinium, pyrrolidinium, and piperidinium salts.

The compounds provided by the present invention may have at least one asymmetric center. Such compounds exist as enantiomers. When the compounds according to the invention have more than two asymmetric centers, they additionally exist as diastereomers. All such isomers and enantio- and diastereo-mixtures of these compounds are also encompassed within the scope of the present invention.

Examples of compounds within the scope of the present invention include:

8-bromo-5,6-dihydro-1H-pyrrolo[1,2,3-de]quinoxaline-2,3-dione; 8-bromo-5-methoxycarbonyl-5,6-dihydro-1H-pyrrolo[1,2,3-de]quinoxaline-2,3-dione;

8-bromo-5-carboxy-5,6-dihydro-1H-pyrrolo[1,2,3-de]quinoxaline-2,3-dione; 8-bromo-5-phthalimidomethyl-5,6-dihydro-1H-pyrrolo[1,2,3-de]quinoxaline-2,3-dione;

8-bromo-5-benzylcarbamoyl-5,6-dihydro-1H-pyrrolo[1,2,3-de]-quinoxaline-2,3-dione;

8-bromo-5-(2-phenylethylcarbamoyl)-5,6-dihydro-1H-pyrrolo[1,2,3-de]quinoxaline-2,3-dione;

8-bromo-5-(phenylcarbamoyl)-5,6-dihydro-1H-pyrrolo[1,2,3-de]quinoxaline-2,3-dione;

8-bromo-5-aminomethyl-5,6-dihydro-1H-pyrrolo[1,2,3-de]quinoxaline-2,3-dione hydrochloride;

8-bromo-5-methoxycarbonylmethyl-5,6-dihydro-1H-pyrrolo[1,2,3-de]quinoxaline-2,3-dione;

8-bromo-5-carboxymethyl-5,6-dihydro-1H-pyrrolo[1,2,3-de]quinoxaline-2,3-dione;

8-bromo-5-carbamoylmethyl-5,6-dihydro-1H-pyrrolo[1,2,3-de]quinoxaline-2,3-dione;

8-bromo-5-phenylcarbamoylmethyl-5,6-dihydro-1H-pyrrolo[1,2,3-de]quinoxaline-2,3-dione;

8-bromo-5-benzylcarbamoylmethyl-5,6-dihydro-1H-pyrrolo[1,2,3-de]quinoxaline-2,3-dione;

8-bromo-5-(N'-phenylureidomethyl)-5,6-dihydro-1H-pyrrolo[1,2,3-de]quinoxaline-2,3-dione;

8-bromo-5-benzoylaminomethyl-5,6-dihydro-1H-pyrrolo[1,2,3-de]quinoxaline-2,3-dione;

8-bromo-5-(N-hydroxycarbamoylmethyl)-5,6-dihydro-1H-pyrrolo[1,2,3-de]-quinoxaline-2,3-dione;

9-bromo-5-methoxycarbonyl-6,7-dihydro-1H, 5H-pyrido[1,2,3-de]quinoxaline-2,3-dione;

9-bromo-5-carboxy-6,7-dihydro-1H, 5H-pyrido[1,2,3-de]quinoxaline-2,3-dione;

9-bromo-5-phenylcarbamoyl-6,7-dihydro-1H, 5H-pyrido[1,2,3-de]quinoxaline-2,3-dione;

9-bromo-5-benzylcarbamoyl-6,7-dihydro-1H, 5H-pyrido[1,2,3-de]quinoxaline-2,3-dione;

9-bromo-5-phenethylcarbamoyl-6,7-dihydro-1H, 5H-pyrido[1,2,3-de]quinoxaline-2,3-dione;

9-bromo-5-methoxycarbonylmethyl-6,7-dihydro-1H, 5H-pyrido[1,2,3-de]-quinoxaline-2,3-dione;

9-bromo-5-carboxymethyl-6,7-dihydro-1H, 5H-pyrido[1,2,3-de]-quinoxaline-2,3-dione;

9-bromo-5-carbamoyl-6,7-dihydro-1H, 5H-pyrido[1,2,3-de]quinoxaline-2,3-dione;

9-bromo-5-(N-hydroxycarbamoyl)-6,7-dihydro-1H, 5H-pyrido[1,2,3-de]quinoxaline-2,3-dione;

9-bromo-5-phenylcarbamoylmethyl-6,7-dihydro-1H, 5H-pyrido[1,2,3-de]quinoxaline-2,3-dione;

9-bromo-5-phthalimidomethyl-6,7-dihydro-1H, 5H-pyrido[1,2,3-de]quinoxaline-2,3-dione;

9-bromo-5-aminomethyl-6,7-dihydro-1H, 5H-pyrido[1,2,3-de]-quinoxaline-2,3-dione hydrochloride;

9-bromo-5-benzoylaminomethyl-6,7-dihydro-1H, 5H-pyrido[1,2,3-de]quinoxaline-2,3-dione;

9-bromo-5-(N'-phenylureidomethyl)-6,7-dihydro-1H, 5H-pyrido[1,2,3-de]quinoxaline-2,3-dione;

9-bromo-5-ethoxycarbonylethyl-6,7-dihydro-1H, 5H-pyrido[1,2,3-de]quinoxaline- 2,3-dione;

9-bromo-5-carboxyethyl-6,7-dihydro-1H, 5H-pyrido[1.2.3-de]quinoxaline-2,3-dione;

9-bromo-5-cyclohexylcarbamoyl-6,7-dihydro-1H, 5H-pyrido[1,2,3-de]quinoxaline-2,3-dione;

9-bromo-5-hydroxymethyl-6,7-dihydro-1H, 5H-pyrido[1,2,3-de]quinoxaline-2,3-dione;

9-bromo-5-methylsulfonyloxymethyl-6,7-dihydro-1H, 5H-pyrido[1,2,3-de]quinoxaline-2,3-dione;

9-bromo-5-iodomethyl-6,7-dihydro-1H, 5H-pyrido[1,2,3-de]quinoxaline-2,3-dione;

9-bromo-5-(O-2-tetrahydropyranyl-N-hydroxycarbamoylmethyl)-6,7-dihydro-1H, 5H-pyrido[1,2,3-de]quinoxaline-2,3-dione;

9-bromo-5-[(1 S)-1-methoxycarbonyl-2-phenylethylcarbamoyl]-6,7-dihydro-1H, 5H-pyrido[1,2,3-de]quinoxaline-2,3-dione;

9-bromo-5-[(1 R)-1-methoxycarbonyl-2-phenylethylcarbamoyl]-6,7-dihydro-1H, 5H-pyrido[1,2,3-de]quinoxaline-2,3-dione;

9-bromo-5-ethoxalylaminomethyl-6,7-dihydro-1H, 5H-pyrido[1,2,3-de]quinoxaline-2,3-dione;

9-bromo-5-oxaloaminomethyl-6,7-dihydro-1H, 5H-pyrido[1,2,3-de]quinoxaline-2,3-dione;

9-bromo-5-cyclopropylcarbamoyl-6,7-dihydro-1H, 5H-pyrido[1,2,3-de]quinoxaline-2,3-dione;

9-bromo-5-(m-ethoxycarbonylphenylcarbamoyl)-6,7-dihydro-1H, 5H-pyrido[1,2,3-de]quinoxaline-2,3-dione;

9-bromo-5-(m-carboxyphenylcarbamoyl)-6,7-dihydro-1H, 5H-pyrido-[1,2,3-de]quinoxaline-2,3-dione;

9-bromo-5-[(1 S)-1-carboxy-2-phenylethylcarbamoyl]-6,7-dihydro-1H, 5H-pyrido[1,2,3-de]quinoxaline-2,3-dione;

9-bromo-5-[(1 R)-1-carboxy-2-phenylethylcarbamoyl]-6,7-dihydro-1H, 5H-pyrido[1,2,3-de]quinoxaline-2,3-dione;

9-bromo-5-benzylcarbamoylmethyl-6,7-dihydro-1H, 5H-pyrido[1,2,3-de]quinoxaline-2,3-dione;

9-bromo-5-benzylmethylcarbamoylmethyl-6,7-dihydro-1H, 5 H-pyrido[1,2,3-de]quinoxaline-2,3-dione;

9-bromo-5-cyclopropylcarbamoylmethyl-6,7-dihydro-1H, 5H-pyrido[1,2,3-de]quinoxaline-2,3-dione;

9-bromo-5-(m-ethoxycarbonylphenylcarbamoylmethyl)-6,7-dihydro-1H, 5H-pyrido[1,2,3-de]quinoxaline-2,3-dione;

9-bromo-5-(p-ethoxycarbonylphenylcarbamoylmethyl)-6,7-dihydro-1H, 5H-pyrido[1,2,3-de]quinoxaline-2,3-dione;

9-bromo-5-(o-ethoxycarbonylphenylcarbamoylmethyl)-6,7-dihydro-1H, 5H-pyrido[1,2,3-de]quinoxaline-2,3-dione;

9-bromo-5-(o-carboxyphenylcarbamoylmethyl)-6,7-dihydro-1H, 5H-pyrido[1,2,3-de]quinoxaline-2,3-dione;

9-bromo-5-(m-carboxyphenylcarbamoylmethyl)-6,7-dihydro-1H, 5H-pyrido[1,2,3-de]quinoxaline-2,3-dione;

9-bromo-5-(p-carboxyphenylcarbamoylmethyl)-6,7-dihydro-1H, 5H-pyrido[1,2,3-de]quinoxaline-2,3-dione;

9-bromo-5-carbamoylmethyl-6,7-dihydro-1H, 5 H-pyrido[1,2,3-de]quinoxaline-2,3-dione;

9-bromo-5-methylphenylcarbamoylmethyl-6,7-dihydro-1H, 5H-pyrido[1,2,3-de]quinoxaline-2,3-dione;

9-bromo-5-cyclohexylcarbamoylmethyl-6,7-dihydro-1H, 5H-pyrido[1,2,3-de]quinoxaline-2,3-dione;

9-bromo-5-(o-sulfamoylphenylcarbamoylmethyl)-6,7-dihydro-1H, 5H-pyrido[1,2,3-de]quinoxaline-2,3-dione;

9-bromo-5-(m-sulfamoylphenylcarbamoylmethyl)-6,7-dihydro-1H, 5H-pyrido[1,2,3-de]quinoxaline-2,3-dione;

9-bromo-5-(p-sulfamoylphenylcarbamoylmethyl)-6,7-dihydro-1H, 5H-pyrido[1,2,3-de]quinoxaline-2,3-dione;

9-bromo-5-(o-methoxyphenylcarbamoylmethyl)-6,7-dihydro-1H, 5H-pyrido[1,2,3-de]quinoxaline-2,3-dione;

9-bromo-5-(m-methoxyphenylcarbamoylmethyl)-6,7-dihydro-1H, 5H-pyrido[1,2,3-de]quinoxaline-2,3-dione;

9-bromo-5-(p-methoxyphenylcarbamoylmethyl)-6,7-dihydro-1H, 5H-pyrido[1,2,3-de]quinoxaline-2,3-dione;

9-bromo-5-(o-acetylphenylcarbamoylmethyl)-6,7-dihydro-1H, 5H-pyrido[1,2,3-de]quinoxaline-2,3-dione;

9-bromo-5-(m-acetylphenylcarbamoylmethyl)-6,7-dihydro-1H, 5 H-pyrido[1,2,3-de]quinoxaline-2,3-dione;

9-bromo-5-(p-acetylphenylcarbamoylmethyl)-6,7-dihydro-1H, 5H-pyrido[1,2,3-de]quinoxaline-2,3-dione;

9-bromo-5-(N-hydroxycarbamoylmethyl)-6,7-dihydro-1H, 5H-pyrido[1,2,3-de]quinoxaline-2,3-dione;

9-bromo-5-(O-methyl-N-hydroxycarbamoylmethyl)-6,7-dihydro-1H, 5H-pyrido[1,2,3-de]quinoxaline-2,3-dione;

trans-9-bromo-5-methoxycarbonylmethyl-6-methyl-6,7-dihydro-1H, 5H-pyrido[1,2,3-de]quinoxaline-2,3-dione;

trans-9-bromo-5-carboxymethyl-6-methyl-6,7-dihydro-1H, 5H-pyrido[1,2,3-de]quinoxaline-2,3-dione;

trans-9-bromo-6-methyl-5-phenylcarbamoylmethyl-6,7-dihydro-1H, 5H-pyrido[1,2,3-de]quinoxaline-2,3-dione;

cis-9-bromo-5-methoxycarbonylmethyl-6-methyl-6,7-dihydro-1H, 5H-pyrido[1,2,3-de]quinoxaline-2,3-dione;

cis-9-bromo-5-carboxymethyl-6-methyl-6,7-dihydro-1H, 5H-pyrido-[1,2,3-de]quinoxaline-2,3-dione;

cis-9-bromo-6-methyl-5-phenylcarbamoylmethyl-6,7-dihydro-1H, 5H-pyrido[1,2,3-de]quinoxaline-2,3-dione;

trans-9-bromo-5-methoxycarbonylmethyl-7-methyl-6,7-dihydro-1H, 5H-pyrido[1,2,3-de]quinoxaline-2,3-dione;

trans-9-bromo-5-carboxymethyl-7-methyl-6,7-dihydro-1H, 5H-pyrido[1,2,3-de]quinoxaline-2,3-dione;

trans-9-bromo-7-methyl-5-phenylcarbamoylmethyl-6,7-dihydro-1H, 5H-pyrido[1,2,3-de]quinoxaline-2,3-dione;

cis-9-bromo-5-methoxycarbonylmethyl-7-methyl-6,7-dihydro-1H, 5H-pyrido[1,2,3-de]quinoxaline-2,3-dione;

cis-9-bromo-5-carboxymethyl-7-methyl-6,7-dihydro-1H, 5H-pyrido[1,2,3-de]quinoxaline-2,3-dione;

cis-9-bromo-7-methyl-5-phenylcarbamoylmethyl-6,7-dihydro-1H, 5H-pyrido[1,2,3-de]quinoxaline-2,3-dione;

9-bromo-5-(O-benzyl-N-hydroxycarbamoylmethyl)-6,7-dihydro-1H, 5H-pyrido[1,2,3-de]quinoxaline-2,3-dione;

9-bromo-5-(2-pyridylcarbamoylmethyl)-6,7-dihydro-1H, 5H-pyrido[1,2,3-de]quinoxaline-2,3-dione;

9-bromo-5-(3-pyridylcarbamoylmethyl)-6,7-dihydro-1H, 5H-pyrido[1,2,3-de]quinoxaline-2,3-dione;

9-bromo-5-(4-pyridylcarbamoylmethyl)-6,7-dihydro-1H, 5H-pyrido[1,2,3-de]quinoxaline-2,3-dione;

9-bromo-5-(O-methyl-N-hydroxycarbamoylmethyl)-6,7-dihydro-1H, 5H-pyrido[1,2,3-de]quinoxaline-2,3-dione;

9-bromo-5-(2-thiazolylcarbamoylmethyl)-6,7-dihydro-1H, 5H-pyrido[1,2,3-de]quinoxaline-2,3-dione;

9-bromo-5-(2-cyanoethylcarbamoylmethyl)-6,7-dihydro-1H, 5H-pyrido[1,2,3-de]quinoxaline-2,3-dione;

9-bromo-5-(2-tetrazolylcarbamoylmethyl)-6,7-dihydro-1H, 5H-pyrido[1,2,3-de]quinoxaline-2,3-dione;

9-bromo-5-(N-hydroxy-phenylcarbamoylmethyl)-6,7-dihydro-1H, 5H-pyrido[1,2,3-de]quinoxaline-2,3-dione;

9-bromo-5-(p-cyanophenylcarbamoylmethyl)-6,7-dihydro-1H, 5H-pyrido[1,2,3-de]quinoxaline-2,3-dione;

9-bromo-5-(p-carbamoylphenylcarbamoylmethyl)-6,7-dihydro-1H, 5H-pyrido[1,2,3-de]quinoxaline-2,3-dione;

9-bromo-5-(p-trifluoromethylphenylcarbamoylmethyl)-6,7-dihydro-1H, 5H-pyrido[1,2,3-de]quinoxaline-2,3-dione;

9-bromo-5-(p-acetylaminophenylcarbamoylmethyl)-6,7-dihydro-1H, 5H-pyrido[1,2,3-de]quinoxaline-2,3-dione;

9-bromo-5-(p-methoxycarbonyl-m-chlorophenylcarbamoylmethyl)-6,7-dihydro-1H, 5H-pyrido[1,2,3-de]quinoxaline-2,3-dione;

9-bromo-5-(p-carboxy-m-chlorophenylcarbamoylmethyl)-6,7-dihydro-1H, 5H-pyrido[1,2,3-de]quinoxaline-2,3-dione;

9-bromo-5-(p-nitrophenylcarbamoylmethyl)-6,7-dihydro-1H, 5H-pyrido[1,2,3-de]quinoxaline-2,3-dione;

9-bromo-5-(o-hydroxyphenylcarbamoylmethyl)-6,7-dihydro-1H, 5H-pyrido[1,2,3-de]quinoxaline-2,3-dione;

9-bromo-5-(o-aminophenylcarbamoylmethyl)-6,7-dihydro-1H, 5H-pyrido[1,2,3-de]quinoxaline-2,3-dione;

9-bromo-5-(p-methoxycarbonylmethylphenylcarbamoylmethyl)-6,7-dihydro-1H, 5H-pyrido[1,2,3-de]quinoxaline-2,3-dione;

9-bromo-5-(p-carboxymethylphenylcarbamoylmethyl)-6,7-dihydro-1H, 5H-pyrido[1,2,3-de]quinoxaline-2,3-dione;

trans-9-bromo-6-methyl-5-(p-sulfamoylphenylcarbamoylmethyl)-6,7-dihydro-1H, 5H-pyrido[1,2,3-de]quinoxaline-2,3-dione;

trans-9-bromo-5-(p-ethoxycarbonylphenylcarbamoylmethyl)-6-methyl-6,7-dihydro-1H, 5H-pyrido[1,2,3-de]quinoxaline-2,3-dione;

trans-9-bromo-5-(p-carboxyphenylcarbamoylmethyl)-6-methyl-6,7-dihydro-1H, 5H-pyrido[1,2,3-de]quinoxaline-2,3-dione;

trans-9-bromo-5-(o-ethoxycarbonylphenylcarbamoylmethyl)-6-methyl-6,7-dihydro-1H, 5H-pyrido[1,2,3-de]quinoxaline-2,3-dione;

trans-9-bromo-5-(o-carboxyphenylcarbamoylmethyl)-6-methyl-6,7-dihydro-1H, 5H-pyrido[1,2,3-de]quinoxaline-2,3-dione;

9-bromo-5-methoxycarbonylmethyl-5-methyl-6,7-dihydro-1H, 5H-pyrido[1,2,3-de]quinoxaline-2,3-dione;

9-bromo-5-carboxymethyl-5-methyl-6,7-dihydro-1H, 5H-pyrido[1,2,3-de]quinoxaline-2,3-dione;

9-bromo-5-methyl-5-phenylcarbamoylmethyl-6,7-dihydro-1H, 5H-pyrido[1,2,3-de]quinoxaline-2,3-dione;

9-bromo-5-(p-aminophenylcarbamoylmethyl)-6,7-dihydro-1H, 5H-pyrido[1,2,3-de]quinoxaline-2,3-dione;

9-bromo-5-(p-1-methoxycarbonylethylphenylcarbamoylmethyl)-6,7-dihydro-1H, 5H-pyrido[1,2,3-de]quinoxaline-2,3-dione;

9-bromo-5-(p-1-carboxyethylphenylcarbamoylmethyl)-6,7-dihydro-1H, 5H-pyrido-[1,2,3-de]quinoxaline-2,3-dione;

9-bromo-5-(1-methoxycarbonylethyl)-6,7-dihydro-1H, 5H-pyrido[1,2,3-de]quinoxaline-2,3-dione; (less polar)

9-bromo-5-(1-methoxycarbonylethyl)-6,7-dihydro-1H, 5H-pyrido[1,2,3-de]quinoxaline-2,3-dione; (more polar)

9-bromo-5-(1-carboxyethyl)-6,7-dihydro-1H, 5H-pyrido[1,2,3-de]quinoxaline-2,3-dione; (less polar)

9-bromo-5-(1-carboxyethyl)-6,7-dihydro-1H, 5H-pyrido[1,2,3-de]quinoxaline-2,3-dione; (more polar)

9-bromo-5-(1-phenylcarbamoylethyl)o6,7-dihydro-1H, 5H-pyrido[1,2,3-de]quinoxaline-2,3-dione; (less polar)

9-bromo-5-(1-phenylcarbamoylethyl)-6,7-dihydro-1H, 5H-pyrido[1,2,3-de]quinoxaline-2,3-dione; (more polar)

9-bromo-5-(2-benzimidazolylmethyl)-6,7-dihydro-1H, 5H-pyrido[1,2,3-de]quinoxaline-2,3-dione hydrochloride;

9-bromo-5-(p-tolylcarbamoylmethyl)-6,7-dihydro-1H, 5H-pyrido[1,2,3-de]quinoxaline-2,3-dione;

9-bromo-5-[(o-methoxycarbonylmethyiphenyl)carbamolylmethyl]-6,7-dihydro-1H, 5H-pyrido[1,2,3-de]quinoxaline-2,3-dione;

9-bromo-5-[(o-carboxymethylphenyl)carbamoylmethyl]-6,7-dihydro-1H, 5H-pyrido[1,2,3-de]quinoxaline-2,3-dione;

9-bromo-5-(p-tert-butoxycarbonylaminomethylphenylcarbamoylmethyl)-6,7-dihydro-1H, 5H-pyrido[1,2,3-de]quinoxaline-2,3-dione;

9-bromo-5-[(p-aminomethylphenyl)carbamoylmethyl]-6,7-dihydro-1H, 5H-pyrido[1,2,3-de]quinoxaline-2,3-dione hydrochloride;

9-bromo-5-(1-naphthylcarbamoylmethyl)-6,7-dihydro-1H, 5H-pyrido[1,2,3-de]quinoxaline-2,3-dione;

9-bromo-5-(8-quinolylcarbamoylmethyl)-6,7-dihydro-1H, 5H-pyrido[1,2,3-de]quinoxaline-2,3-dione;

9-bromo-5-(o-carbamoylphenylcarbamoylmethyl)-6,7-dihydro-1H, 5H-pyrido[1,2,3-de]quinoxaline-2,3-dione;

9-bromo-5-(2-benzothiazolylcarbamoylmethyl)-6,7-dihydro-1H, 5H-pyrido[1,2,3-de]quinoxaline-2,3-dione;

9-bromo-5-(N,O-dimethyl-N-hydroxycarbamoylmethyl)-6,7-dihydro-1H, 5H-pyrido[1,2,3-de]quinoxaline-2,3-dione;

9-bromo-5-{[p-2-methoxycarbonyl-(E)-ethenylphenyl]carbamoylmethyl}-6,7-dihydro-1H, 5H-pyrido[1,2,3-de]quinoxaline-2,3-dione;

9-bromo-5-{[p-2-carboxy-(E)-ethenylphenyl]carbamoyl-methyl}-6,7-dihydro-1H, 5H-pyrido[1,2,3-de]quinoxaline-2,3-dione;

9-chloro-5-methoxycarbonylmethyl-6,7-dihydro-1H, 5H-pyrido[1,2,3-de]quinoxaline-2,3-dione;

9-chloro-5-carboxymethyl-6,7-dihydro-1H, 5H-pyrido[1,2,3-de]quinoxaline- 2,3-dione;

9-chloro-5-phenylcarbamoylmethyl-6,7-dihydro-1H, 5H-pyrido[1,2,3-de]quinoxaline-2,3-dione;

9-cyano-5-methoxycarbonylmethyl-6,7-dihydro-1H, 5H-pyrido[1,2,3-de]quinoxaline-2,3-dione;

cyano-5-carboxymethyl-6,7-dihydro-1H, 5H-pyrido[1,2,3-de]quinoxaline-2,3-dione;

9-cyano-5-phenylcarbamoylmethyl-6,7-dihydro-1H, 5H-pyrido[1,2,3-de]quinoxaline-2,3-dione;

9-iodo-5-methoxycarbonylmethyl-6,7-dihydro-1H, 5H-pyrido[1,2,3-de]quinoxaline-2,3-dione; 9-iodo-5-carboxymethyl-6,7-dihydro-1H, 5H-pyrido[1,2,3-de]quinoxaline-2,3-dione;

5-methoxycarbonylmethyl-9-nitro-6,7-dihydro-1H, 5H-pyrido[1,2,3-de]quinoxaline-2,3-dione;

9-bromo-6,7-dihydro-1H, 5H-pyrido[1,2,3-de]quinoxaline-2,3-dione;

9-bromo-5-cyanomethyl-6,7-dihydro-1H, 5H-pyrido[1,2,3-de]quinoxaline-2,3-dione;

9-bromo-5-formyl-6,7-dihydro-1H, 5H-pyrido[1,2,3-de]quinoxaline-2,3-dione;

9-bromo-5-benzylaminomethyl-6,7-dihydro-1H, 5H-pyrido[1,2,3-de]quinoxaline-2,3-dione hydrochloride;

and salts thereof;

wherein the numbering used for the novel tricyclic quinoxaline systems is as shown in the following figure.

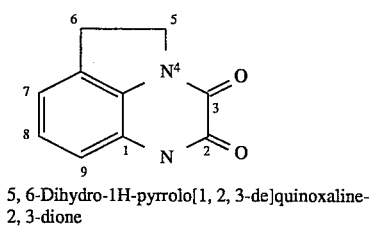

5, 6-Dihydro-1H-pyrrolo[1, 2, 3-de]quinoxaline-2, 3-dione

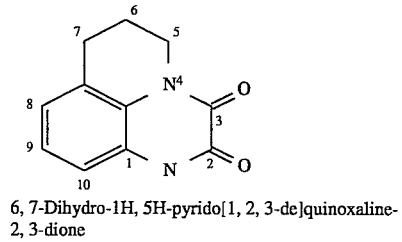

6, 7-Dihydro-1H, 5H-pyrido[1, 2, 3-de]quinoxaline-2, 3-dione

The tricyclic quinoxalinediones of the present invention can be formulated to conventional pharmaceutical preparations such as tablets, pills, capsules, powders, granules, suspensions, or emulsions all for oral administration, and such as sterile parenteral solutions or suppositories for parenteral or rectal administration, respectively. The solid compositions such as tablets can be routinely prepared by mixing the active ingredient with conventional pharmaceutical carriers such as lactose and sucrose, binders such as corn starch, disintegrating agents such as potato starch, lubricant such as stearic acid, or preservatives. For parenteral administration, the active compound is dissolved or suspended in a physiologically acceptable pharmaceutical carrier such as water, saline, oils or dextrose solution, which may contain auxiliary agents such as emulsifiers, stabilizers, salt for influencing osmotic pressure, or buffers, if desired. The dosage range can be varied widely depending on the severity of the particular disease, age, weight, and sex of the patient, and the route of administration. Typically, effective dosages are in the range of 1 to 1000 mg/day, or preferably of 10 to 500 mg/day orally for adult patients, which may be given in a single dose or in multiple doses. For parenteral administration, the dosage range of 0.1 to 500 mg/day, or more suitably of 3 to 100 mg/day/patient can be employed with a single dose or with multiple doses.

The key intermediary compounds represented by formula 7, which themselves are also the desired compounds of the present invention, may be prepared as illustrated in the following scheme;

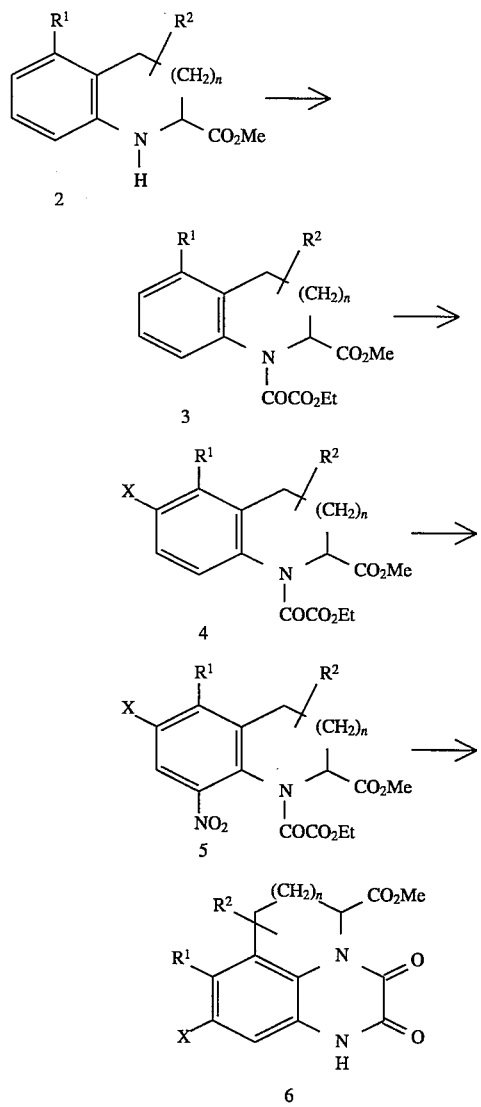

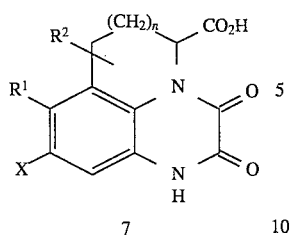

wherein $R^1$, $R^2$, n, and X are as defined above.

1) Compounds of formula 2 are transformed to compounds 3 by reaction with ethyl chloroglyoxalate in an inert solvent such as methylene chloride, chloroform, tetrahydrofuran (THF), and ethyl acetate, at temperature range of −10° to 30° C. Compounds of formula 2 may be readily prepared by a method described in literatures. For example, tetrahydroquinoline-2-carboxylic acid methyl ester may conveniently be prepared by hydrogenation of quinaldinic acid over $PtO_2$ in methanol followed by treatment of thionyl chloride in methanol at ambient to refluxing temperature, or by direct hydrogenation of quinaldinic acid methyl ester in acetic acid. Alternatively, tetrahydroquinoline-2-carboxylic acid methyl ester may be prepared by reduction of quinaldinic acid methyl ester with combination of $NiCl_2$ and sodium borohydride in methanol at 0° C. to room temperature. $R^1$ and/or $R^2$-substituted tetrahydroquinoline-2-carboxylic acid methyl esters included in compounds 2 can be prepared by following sequence: a) Carboxyl group can be introduced into C-2 position of $R^1$ and/or $R^2$-substituted quinolines by using Reissert reaction followed by hydrolysis (W. E. McEwen and R. L. Cobb, Chem. Rev., 55, 511 (1955)); and b) the resulting substituted quinoline-2-carboxylic acids are methylated, and then reduced to the corresponding tetrahydroquinoline-2-carboxylic acid methyl esters as mentioned above. The $R^1$ and/or $R^2$ substituted quinolines may be commercially available or readily prepared by using Skraup reaction (R. H. F. Manske and M. Kulka, Org. Rect., 7, 59 (1953)). Similarly, indoline-2-carboxylate derivatives (n=0) may be prepared by a method, for example, disclosed in J. L. Stanton et al., J. Med. Chem., 26, 1267 (1983). When $R^2$ is not hydrogen, compounds 2 may exist as a diastereomixture. Such a diastereomer can be conveniently separated to a pure isomer by a conventional column chromatography technique.

2) Compounds 3 are converted to compounds 4 by using conventional aromatic electrophilic substitution technique (see, for example Advanced Organic Chemistry, Jerry March ed., Chapter 13, 576). In the case of X=Br, compounds 3 are reacted with bromine in a halogenated solvent such as methylene chloride in the presence or absence of a catalyst such as Fe powder to give the brominated compounds inclusive in 4. When X is Br, compounds 4 can also be synthesized by direct bromination of compounds 3 with N-bromosuccinimide in dimethylformamide (DMF) followed by acylation with ethyl chloroglyoxalate.

3) Compounds 4 can be transformed to compounds 5 by conventional nitration conditions including treatment with fuming nitric acid at 0° C. to ambient temperature, nitric acid or isopropyl nitrate in concentrated sulfuric acid at 0° C. to ambient temperature, a mixed reagent of trifluoroacetic anhydride and ammonium nitrate in a halogenated solvent such as chloroform and methylene chloride at ambient to refluxing temperature, and nitronium tetrafluoroborate in a halogenated solvent such as chloroform and methylene chloride at ambient temperature.

4) Reductive ring closure of compounds 5 to 6 are effected by aqueous titanium trichloride in a protic solvent such as methanol, ethanol, and acetic acid or in an aprotic solvent such as acetone, THF, and DMF at 0° C. to ambient temperature. Other reducing reagents including stannous dichloride, zinc, iron powder, and formate-palladium on carbon may be utilizable for the ring closure.

5) Carboxylic acids 7 can be prepared by hydrolysis of 6. The hydrolytic conditions include treatment with an alkaline metal hydroxide or carbonate such as lithium hydroxide, sodium hydroxide, potassium carbonate in a mixed solvent of water and a protic or aprotic solvent such as methanol, ethanol, or THF at temperature range of 0° to 50° C., or treatment with an aqueous strong acid such as 1N~12N hydrochloric acid, or 5~48% hydrobromic acid in a protic or aprotic solvent such as acetic acid or dioxane at temperature range of ambient temperature to 100° C.

Compounds of formula 2 wherein the $R^2$ is attached to the C-2 position can be prepared by the route outlined below;

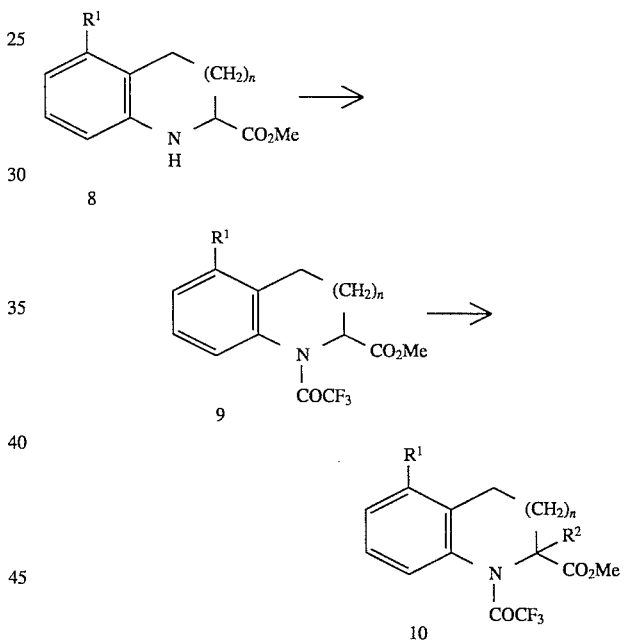

wherein $R^1$, $R^2$, and n are as defined above.

1) Compounds 8 are protected to the corresponding trifluoroacetyl derivatives 9 with trifluoroacetic anhydride by using conventional acylating conditions as described in the conversion of 2 to 3.

2) The trifluoroacetyl derivatives 9 are deprotonated at −78° C. in an inert solvent such as diethyl ether and THF by using a strong base such as lithium diisopropylamide and potassium hexamethyldisilazide, followed by treatment with an iodide represented by $R^2I$ to provide 10.

3) Acid hydrolysis of 10 affords the compounds having $R^2$ at C-2 position, which are inclusive in 2.

Compounds of the present invention represented by formula 12 may be prepared from 11 according to a sequence analogous to that used in the conversion of 2 to 6 as shown below;

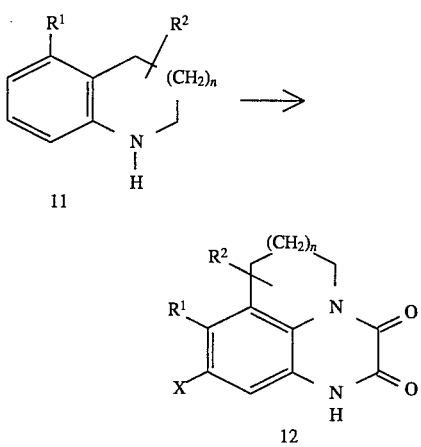

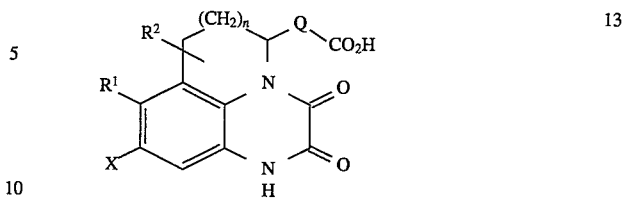

wherein R1, R2, n, and X are as defined above and Q represents straight chained or branched alkylene.

Compounds 18 which has a —CH$_2$— group as Q of formula 13 may be prepared as illustrated in the following scheme;

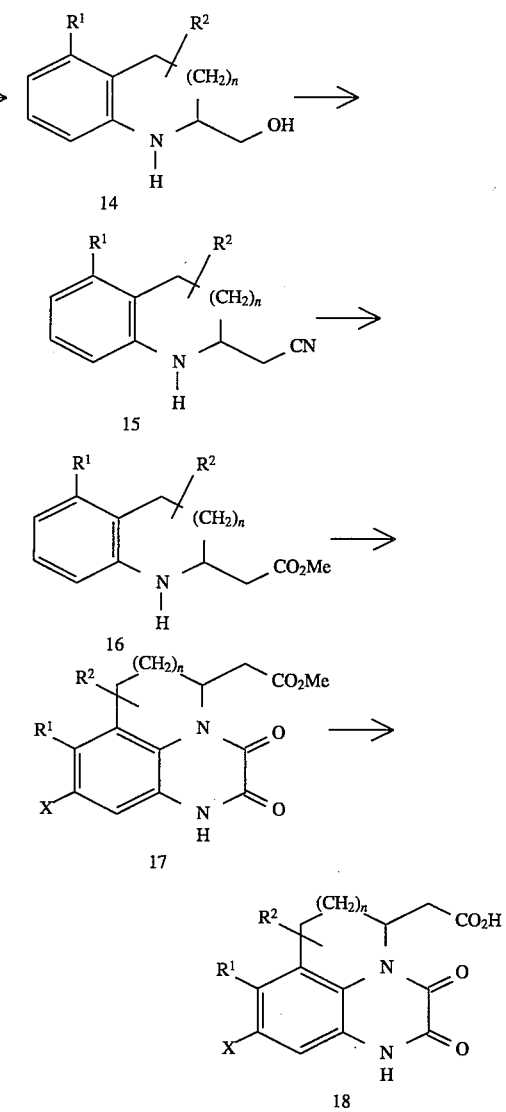

wherein R$^1$, R$^2$, n, and X are as defined above.

wherein R$^1$, R$^2$, n, and X are as defined above.

Compounds 11 are commercially available or readily prepared. For example, tetrahydroquinoline derivatives are obtained by hydrogenation over PtO$_2$ or reduction with sodium borohydride-NiCl$_2$ of the corresponding quinoline derivatives. Indoline drivatives are prepared, for example, by cyclization of the corresponding o-bromoethylanilines.

Condensation of the carboxylic acids 7 with a suitable amine or alcohol represented by R$^3$R$^4$NH (including NH$_3$), R$^4$(R$^3$O)NH, R$^3$YNH, R$^3$OH, or YOH provides the compounds having —CONR$^3$R$^4$ (including —CONH$_2$), —CON(OR$^3$)R$^4$, —CONR$^3$Y, —CO$_2$R$^3$, or —CO$_2$Y group as substituent W of formula 1, respectively. The condensation may be carried out in the presence of a conventional condensation reagent such as 1-ethyl-3-(3'-dimethylaminopropyl)carboximide-hydroxybenzotriazole, isobutyl chloroformate-triethylamine, and N,N-bis(2-oxo-3-oxazolidinyl)phosphinic chloride-triethylamine in an inert solvent such as DMF, THF, and dichloromethane at 0° C. to ambient temperature.

Compounds of formula 1 wherein W is a —COR$^3$ group may be prepared by reaction of the corresponding N,O-dimethylhydroxamate (—CONMeOMe) with a Grignard reagent R$^3$MgBr or organolithium reagent R$^3$Li (R$^3$ is not hydrogen) or isobutyl aluminum hydride (for providing —CHO) in an aprotic solvent such as THF at 0° C. to ambient temperature (S. Nahm and S. M. Weinreb, Tetrahedron Lett., 22, 3819 (1981)). The N,O-dimethylhydroxamates are readily prepared by condensation of the corresponding carboxilic acid 7 with N,O-dimethylhydroxylamine as mentioned above.

Compounds of formula 1 wherein W is a —COR$^3$ group may also be prepared by oxidation of the corresponding alcohol having a —CH(OH)R$^3$ group as substituent W with an appropriate oxidizing reagent such as PCC and Dess-Martin reagent. Examples for preparation of such alcohols are described later.

Compounds of formula 1 wherein W is a cyanide group may be prepared by dehydration of the corresponding amide (W is CONH$_2$) with a suitable dehydrating reagent such as POCl$_3$ at ambient to elevated temperature. The amides can be prepared by condensation of 7 with ammonia as mentioned above.

Compounds of formula 1 wherein W is a tetrazolyl group may be prepared by reaction of the corresponding cyanide prepared as above with sodium azide in an aprotic solvent such as DMF at temperature range of 50° to 80° C.

The carboxylic acids 13, which are another key intermediates to produce compounds of the present invention, can 1) Compounds 2 are reduced to the corresponding alcohols 14 by using lithium aluminum hydride in an inert solvent such as diethyl ether or THF at 0° C. to refluxing temperature.

2) Compounds 14 can be converted into 15 by two step sequences: a) treatment with triphenyl phosphine-imidazole-iodine in toluene or in a mixed solvent of toluene-acetonitrile at 0° C. to ambient temperature to form the corresponding iodides, and b) replacement of the iodide to the cyanide with sodium cyanide in DMF at ambient temperature to around 80° C. to provide 15.

3) Hydrolysis of compounds 15 with a strong acid such as 12N hydrochloric acid at elevated temperature followed by methylation of the resulting carboxylic acid with thionyl chloride in methanol gives compounds 16.

4) Ring closure of 16 to compounds 17 can be carried out as described in the formation of 2 to 6.

5) Hydrolysis of 17 may provide 18 as shown in the conversion of 6 to 7.

Compounds 24 which possess a branched alkylene —$CH(CH_2A^2)$— as Q can be prepared as outlined in the following scheme;

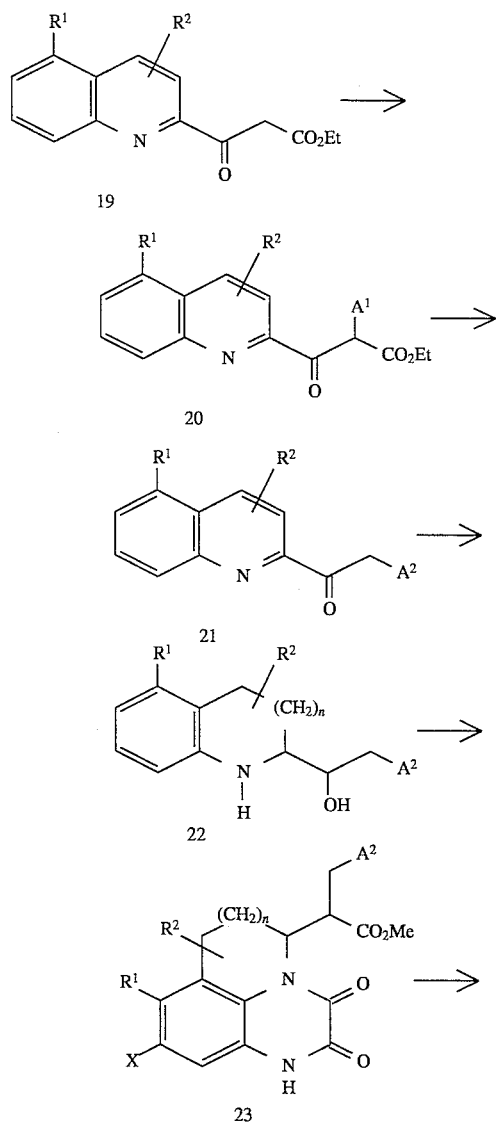

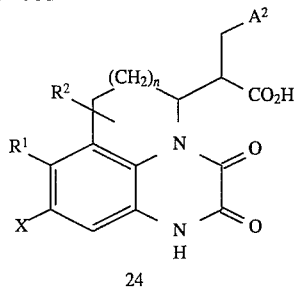

wherein $R^1$, $R^2$, n, and X are as defined above, $A^1$ represents an appropriate alkyl including methyl and ethyl, and $A^2$ represents hydrogen or $A^1$.

For example, the synthesis can be started with 19, when n is 1. Compounds 19 are readily available by Claisen condensation of the corresponding methyl quinoline-2-carboxylate derivative with ethyl acetate in the presence of sodium ethoxide.

1) Compounds 19 are deprotonated with a base such as NaH and potassium tert-butoxide in an aprotic solvent such as THF at 0° C. to ambient temperature followed by treatment with $A^1l$ or $A^1OTs$ to give compounds 20.

Compounds 19 or 20 are hydrolyzed with a strong acid such as 12N hydrochloric acid at elevated temperature to give compounds 21.

3) Hydrogenation of compounds 21 over $PtO_2$ in a protic solvent such as acetic acid and ethanol directly affords intermediates 22 (n=1).

Similarly, starting with indoline-2-carboxylic acid methyl ester derivative 3 (n=0), the sequence of Claisen condensation with ethyl acetate, alkylation with $A^1l$ or $A^1OTs$, acid hydrolysis, and subsequently reduction with sodium borohydride in methanol may provide 22 (n=0).

Transformation of 22 into carboxylic acids 24 via 23 can be carried out as described in the conversion of 14 into 18.

Compounds 30 which have a straight chained or branched alkylene —$CH_2CH(A^2)$— group as Q may be prepared as illustrated in the following scheme;

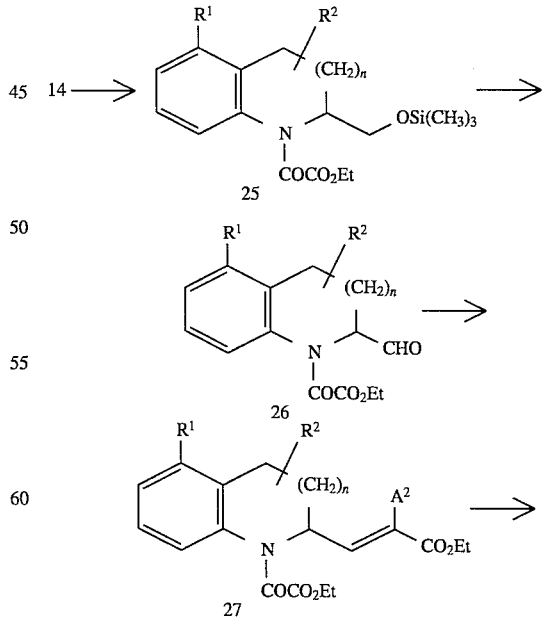

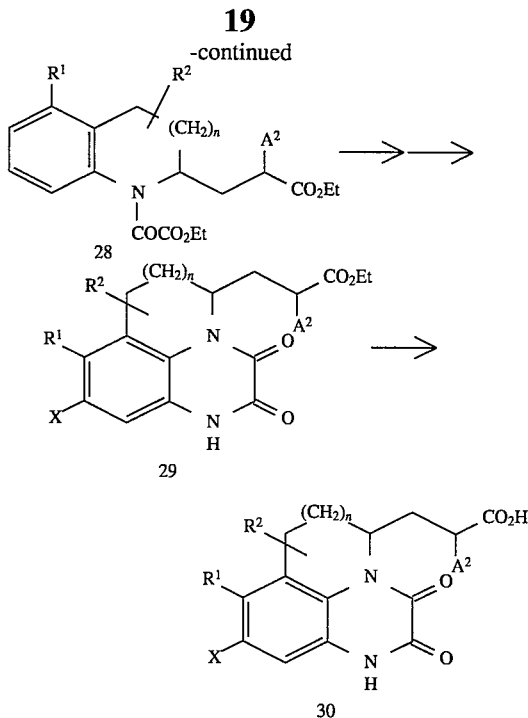

wherein $R^1$, $R^2$, n, $A^2$ and X are as defined above.

1) Compounds 14 are selectively N-acylated to give 25 by subsequent treatment at first with trimethylsilyl chloride and secondly with ethyl chloroglyoxalate in the presence of triethylamine in a halogenated solvent such as dichloromethane at 0° C.

2) Compounds 25 are oxidized to aldehydes 26 by using Dess-Martin periodinane in methylene chloride in the presence of trifluoroacetic acid (D. B. Dess and J. C. Martin, J. Am. Chem. Soc., 113, 7277 (1991)).

3) Wittig-Horner reaction of the aldehydes 26 with an anion of diethyl phosphonoacetic acid ethyl ester derivative in an inert solvent such as THF at 0° C. to ambient temperature provides 27.

4) Olefins 27 can be readily hydrogenated over palladium on charcoal in an inert solvent such as ethyl acetate and ethanol to afford 28.

5) Transformation of 28 into compounds 29 and then 30 can be carried out as described in the conversion of 3 into 7 via 6.

Thus, by applying the reactions explained above, a straight chained or branched alkylene group containing desired number of carbon atoms as Q of formula 13 may be available.

The carboxylic acids of formula 13 can provide compounds of formula 1 wherein W is a group of, e.g. —Q—$CO_2R^3$, —Q—$CO_2Y$, —Q—$CONR^3R^4$, —Q—$CONR^3Y$, —Q—$CON(OR^3)R^4$, —Q—$COR^3$, —Q—CN, —Q-tetrazolyl, etc., by the same manner as described in the transformation of the carboxylic acids 7 into the compounds of formula 1 wherein W is a —$CO_2R^3$, —$CO_2Y$, —$CONR^3R^4$, —$CONR^3Y$, —$CON(OR^3)R^4$, —$COR^3$, —CN, or -tetrazolyl.

Compounds of formula 1 wherein W is a —$CH_2OH$ group may be prepared from 7. Namely, 7 is condensed with N-hydroxysuccinimide by using a condensation reagent such as 1-ethyl-3-(3'-dimethylaminopropyl)carboximide in an aprotic solvent such as DMF, followed by treatment with sodium borohydride in THF at 0° C. to give the alcohols in which substituent W of formula 1 is a —$CH_2OH$ group.

Similarly, alcohols of the invention in which substituent W of formula 1 is a —Q—$CH_2OH$ group can be obtained from the carboxylic acids represented by formula 13.

Reduction of ketones and aldehydes which have a —$COA^3$ or —Q—$COA^3$ group as substituent W of formula 1 with sodium borohydride in methanol may also give the alcohols having a —$CH(OH)A^3$ or —Q—$CH(OH)A^3$ group as W, respectively. The compounds having a —$COA^3$ or —Q—$COA^3$ group as W of formula 1 may be prepared by the same manner as described in the synthesis of the compounds having a —$COR^3$ or —Q—$COR^3$ group as W of formula 1, wherein $A^3$ represents hydrogen or alkyl.

As shown above, the alcohols represented by formula 32 may be readily available;

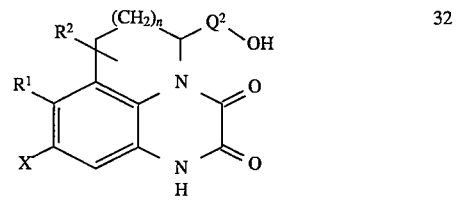

wherein $R^1$, $R^2$, n, and X are as defined above and $Q^2$ represents straight chained or branched alkylene including —$CH^2$—, —Q—$CH_2$—, —$CH(A^3)$—, and —Q—$CH(A^3)$—(Q and $A^3$ are as defined above).

The hydroxyl group of compounds 32 thus obtained may be interconvertible into various substituents by a conventional method, for example, as described below.

Condensation of alcohols 32 of the invention with a suitable carboxylic acid represented by $R^3CO_2H$, $YCO_2H$, $R^3OCOCO_2H$, $R^3COCO_2H$, or $R^3R^4NCOCO_2H$ provides the corresponding esters which have a —$Q^2$—$OCOR^3$, —$Q^2$—OCOY, —$Q^2$—$OCOCO_2R^3$, —$Q^2$—$OCOCOR^3$ or $OCOCONR^3R^4$ group, respectively, as W of formula 1. The condensation may be carried out in the presence of a condensation reagent such as 1-ethyl-3-(3'-dimethylaminopropyl)carboximide-hydroxybenztriazole, isobutyric anhydride-triethylamine, and N,N-bis(2-oxo-3-oxazolidinyl)-phosphinic chloride-triethylamine in an inert solvent such as DMF, THF, and dichloromethane at 0° C. to ambient temperature. Alternatively, the same esters as above may be prepared by reaction of the alcohol 32 with a suitable acid chloride represented by $R^3COCl$, YCOCl, $R^3OCOCOCl$, $R^3COCOCl$, or $R^3R^4NCOCOCl$ in the presence of an appropriate organic base such as triethylamine in an inert solvent such as DMF, THF, and dichloromethane at ambient temperature.

Reaction of the alcohols 32 of the invention with a suitable isocyanate represented by $R^3NCO$ in the presence of an appropriate organic base such as triethylamine in an inert solvent such as DMF, THF, and dichloromethane at ambient temperature to elevated temperature provides the corresponding carbamates which have a —$Q^2$—$OCONHR^3$ group as W of formula 1.

Reaction of the alcohols 32 of the invention with a suitable chloroformate represented by $R^3R^4NCOCl$ or $R^3OCOCl$ in the presence of an appropriate organic base such as triethylamine in an inert solvent such as DMF, THF, and dichloromethane at ambient temperature to elevated temperature provides the corresponding carbamates and carbonates which have a —$Q^2$—$OCONR^3R^4$ or —$Q^2$—$OCO_2R^3$ group, respectively, as W of formula 1.

Interconversion of the alcohols represented by formula 32 into the iodides 34 and the amines 31 may be achieved as shown below;

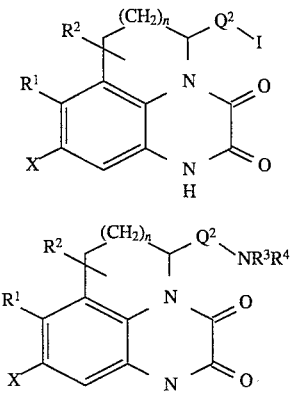

34

31 wherein $R^1$, $R^2$, n, $Q^2$, $R^3$, $R^4$ and X are as defined above.

For example, 32 is reacted with methanesulfonyl chloride in the presence of an appropriate base such as triethylamine in an inert solvent such as THF and dichloromethane to give the corresponding methanesulfonates, which are converted to iodides 34 by treatment with metal iodide such as sodium iodide in an aprotic solvent such as DMF at elevated temperature.

Compounds 31 wherein W of formula 1 is a —$Q^2$—$NR^3R^4$ group (including —$Q^2$—$NHR^3$) may be obtained by reaction of 34 with $HNR^3R^4$ (including $H_2NR^3$) in a polar solvent such as DMF or THF in the presence or absence of a base such as triethylamine and potassium carbonate at ambient to elevated temperature. Alternatively, reductive amination of the compounds having a —$COA^3$ or —Q—CO—$A^3$ group as W of formula 1 with $HNR^3R^4$ (including $H_2NR^3$) by using sodium borohydride or sodium cyanoborohydride in methanol may also afford the compounds having a —$CH(A^3)NR^3R^4$ or —Q—$CH(A^3)NR^3R^4$ group (including —$CH(A^3)NHR^3$ or —Q—$CH(A^3)NHR^3$ group) as W of formula 1, which are inclusive in the compounds represented by formula 31.

Condensation of the compounds having a —$Q^2$—$NHR^3$ group as W of formula 1, which are inclusive in compounds 31, with a suitable carboxylic acid represented by $R^4CO_2H$, $YCO_2H$, $R^4OCOCO_2H$, $R^4COCO_2H$, or $R^4R^5NCOCO_2H$ provides the corresponding amides which have a —$Q^2$-$NR^3COR^4$, —$Q^2$—$NR^3COY$, —$Q^2$—$NR^3COCO_2R^4$, —$Q^2$—$NR^3COCOR^4$ or —$Q^2$—$NR^3COCONR^4R^5$ group, respectively, as W of formula 1. The condensation may be carried out in the presence of a condensation reagent such as 1-ethyl-3-(3'-dimethylaminopropyl)carboximide-hydroxybenztriazole, isobutyric anhydride-triethylamine, and N,N-bis(2-oxo-3-oxazolidinyl)-phosphinic chloride-triethylamine in an inert solvent such as DMF, THF, and dichloromethane at 0° C. to ambient temperature. Alternatively, the same amides as above may be prepared by reaction of amine 31 with a suitable acid chloride represented by $R^4COCl$, YCOCl, $R^4OCOCOCl$, $R^4COCOCl$, or $R^4R^5NCOCOCl$ in the presence of an appropriate organic base such as triethylamine in an inert solvent such as DMF, THF, and dichloromethane at ambient temperature.

Reaction of the compounds having a —$Q^2$—$NHR^3$ group as W of formula 1, which are inclusive in compounds 31, with a suitable isocyanate represented by $R^4NCO$ in the presence of an appropriate organic base such as triethylamine in an inert solvent such as DMF, THF, and dichloromethane at ambient temperature to elevated temperature provides the corresponding ureas which have a —$Q^2$—$NR^3CONHR^4$ group as W of formula 1.33

Reaction of the compounds having a —$Q^2$—$NHR^3$ group as W of formula 1, which are inclusive in compounds 31, with a suitable chloroformate represented by $R^4R^5NCOCl$ or $R^4OCOCl$ in the presence of an appropriate organic base such as triethylamine in an inert solvent such as DMF, THF, and dichloromethane at ambient temperature to elevated temperature provides the corresponding ureas, and carbamates which have a —$Q^2$—$NR^3CONR^4R^5$ or —$Q^2$—$NR^3CO_2R^4$ group, respectively, as W of formula 1.

According to a similar method for preparing the methanesulfonates in the synthesis of iodides 34, reaction of alcohols 32 with $R^3SO_2Cl$ may provide the corresponding sulfonates which have a —$Q^2$—$OSO_2R^3$ group as W of formula 1. Similarly, reaction of the compounds having a —$Q^2$—$NHR^3$ group as W of formula 1, which are inclusive in compounds 31, with $R^4SO_2Cl$ may also give the compounds which have a —Q—$NR^3SO_2R^4$ group as W of formula 1.

Iodides 34 may be converted into various compounds having a —$Q^2$—CN, —$Q^2PO(OR^3)_2$, —$Q^2$—$OR^3$, —$Q^2$—$SR^3$, —$Q^2$—$SO_2R^3$, —$Q^2$—$SO_3H$, —$Q^2$—Cl, or —$Q^2$—Br group by reaction with NaCN, $P(OR^3)_3$, $R^3ONa$, $R^3SNa$ (including HSNa), $R^3SO_2Na$, $HSO_3Na$, LiCl, or LiBr, respectively, in a polar solvent such as THF and DMF at elevated temperature.

Iodides 34 may also be exchangeable to the compounds having a —$Q^2$-heterocycloalkyl group such as —$Q^2$-1-piperidinyl or —$Q^2$-1-morpholinyl as W of formula 1 by reaction with piperidine and morpholine, respectively, in a polar solvent such as THF at elevated temperature.

Treatment of iodides 34 with potassium phthalimide in DMF at 50° to 80° C. may provide the compounds having a —$Q^2$-phthalimido group as W of formula 1. Acid hydrolysis of the phthalimides may afford the compounds which have a —$Q^2$—$NH_2$ group as W of formula 1. The acid hydrolysis conditions include treatment with an aqueous strong acid such as 6N~12N hydrochloric acid, or 25~48% hydrobromic acid in a protic or aprotic solvent such as acetic acid or dioxane at temperature range of 50° to 100° C.

Alternatively, phthalimido group of W can be introduced into a molecule at initial stage of the synthesis leading to the compounds of the invention as shown below, where synthesis of the compounds having a —$CH_2$-phthalimido group as W of formula 1 are typically exemplified;

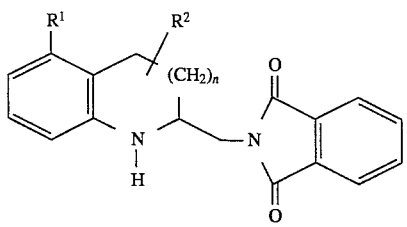

33 wherein $R^1$, $R^2$, n, and X are as defined above.

1) Compounds 14 can be converted into 33 by two steps sequence: a) treatment with triphenyl phosphine-imidazole-iodine in toluene or in a mixed solvent of toluene-acetonitrile at 0° C. to ambient temperature to form the corresponding iodide, and b) replacement of the iodide to the phthalimide with potassium phthalimide in DMF at ambient temperature to around 80° C. to provide 33. Alternatively, compounds 33 are prepared from 2 by three steps sequence: a) treatment of 2 with ammonia in methanol to give the corresponding amide, b) conversion of the amide to the corresponding primary amine by using lithium aluminum hydride in THF at reflux temperature, and c) condensation of the diamine with phthalic anhydride in toluene under azeotropic conditions.

2) Transformation of 33 into the compounds having a —$CH_2$-phthalimido group as W of formula 1 can be carried out as described in the conversion of 2 into 6.

Compounds of formula 1 wherein W is a sulfoxide group —$Q^2$—$SOR^3$ may be readily prepared by oxidation of the corresponding sulfide —$Q^2$—$SR^3$ with an appropriate oxidizing reagent such as hydrogen peroxide. Furthermore, compounds of formula 1 wherein W is a sulfone group —$Q^2$—$SO_2R^3$ may be readily prepared by oxidation of the corresponding sulfide —$Q^2$—$SR^3$ or sulfoxide —$Q^2$—$SOR^3$ with an appropriate oxidizing reagent such as m-chloroperbenzoic acid.

Compounds of formula 1 wherein W is a sulfonic acid —$Q^2$—$SO_3H$ may be converted into the corresponding sulfonyl chlorides which have a —$Q^2$—$SO_2Cl$ group as W of formula 1 by reaction with phosphorous pentachloride in the presence of pyridine. Treatment of the sulfonyl chlorides with $R^3OH$ or $R^3R^4NH$ in an inert solvent such as THF and dichloromethane in the presence of a base such as triethylamine may provide the compounds having a sulfonate —$Q^2$—$SO_3R^3$ or sulfoneamide —$Q^2$—$SO_2NR^3R^4$ group as W of formula 1.

Compounds of formula 1 wherein W is a —$Q^2$-heteroaryl group (or —$Q^2$-substituted heteroaryl) may generally be synthesized by reaction of iodide 34 with a heteroaryl (or substituted heteroaryl) cuprate reagent or a heteroaryl (or substituted heteroaryl) Grignard-cuprous bromide mixed reagent in an inert solvent such as THF and diethyl ether at 0° C. to ambient temperature. Under these conditions, the trifluoromethanesulfonates having a —$Q^2$-OTf group as W of formula 1, instead of 34, may be utilized. The trifluoromethanesulfonates can be prepared by reaction of 32 with trifluoromethanesulfonic anhydride in the presence of triethylamine in an inert solvent such as THF and dichloromethane at −20° to 0° C.

As another example of the compounds having a —Q-heteroaryl group as W of formula 1, synthesis of compounds which possess a —Q-2-benzimidazolyl group is described. Namely, condensation of the carboxilic acid 13 with orthophenylenediamine followed by heating in an inert solvent such as THF in the presence of an acid such as hydrochloric acid affords the corresponding benzimidazolyl derivative having a —Q-2-benzimidazolyl group as W of formula 1.

Synthesis of compounds having a —Q-tetrazolyl group as W of formula 1, which are also inclusive in compounds of formula 1 wherein W is a heteroaryl alkyl, is mentioned above.

The compounds of formula 1 wherein X is Br may be especially useful, since the Br substituent of X can be readily displaced to various substituents such as Cl, I, CN, $CH_3$, and $CF_3$ under conditions such as CuCl-dimethyl sulfoxide-150° C., CuI-KI-hexamethylphosphorous triamide-150° C., CuCN-dimethyl sulfoxide-150° C., methyl cuprate-THF-0° C., and $CF_3CO_2Na$-CuI-N-methylpyrrolidone-160° C., respectively. The Br substituent of X of formula 1 may be replaced to $NO_2$ substituent by debromination with catalytic hydrogenation by using Pd/C in methanol followed by standard nitration as mentioned before.

According to the methods as described above, the compounds of the invention may be prepared in racemic form. However, the compounds of the invention may be obtained in enantiomeric pure form by resolving an appropriate racemic intermediate during the synthesis, or the compounds of the invention themselves. The resolution includes salt-formation of the compound having a basic moiety with an optically pure acid such as (+)-tartaric acid, and also salt-formation of the compound having an acidic moiety with an optically pure amine such as quinine and quinidine, followed by fractional recrystallization and regeneration of the parent compound. The resolution technique also includes amide or ester formation of the compound having carboxylate, amine, or alcohol with chiral-auxiliary, followed by chromatographic separation and removal of the auxiliary.

A certain compound in the invention may be obtained by using conventional protection-deprotection techniques, if necessary or desirable, during synthesis as described above. Such techniques are described in T. W. Greene, Protective Groups in Organic Synthesis, John Wiley & Sons, 1981.

The quinoxalinediones of the present invention strongly inhibit both [$^3$H] MK-801 binding and [$^3$H] glycine binding to the rat brain synaptic membrane preparation, implying that these compounds are potent antagonists at strychnine-insensitive glycine modulatory site of NMDA (N-methyl D-aspartate) receptors (see, for example, A. C. Foster, et al., Mol. Pharmacol., 41, 914 (1992)). The activities of the quinoxalinediones were measured by [$^3$H] MK-801 and [$^3$H] glycine binding inhibition studies as illustrated below.

[$^3$H] glycine binding studies

A crude rat brain synaptic membrane preparation was washed three times by centrifugation at 50,000× g for 30 min with 50 mM tris acetate (pH 7.4). The pellets obtained were suspended in 0.23M sucrose solution and stored at −80° C. For binding studies, The frozen suspension was thawed, treated with 0.08% triton X-100 at 2° C. for 10 min, and washed twice by the centrifugation as mentioned above. The synaptic membrane thus prepared (ca. 150–200 μg protein) was incubated with 10 nM [$^3$H] glycine (40 Ci/mmol) and the test compound (10 μg/mL–1 ng/mL) at 2° C. for 10 min in 50 mM tris acetate (pH 7.4). The incubation was terminated by suction filtration using Whatman GF/B glass filter. The radioactivities bound to the membrane on the filter was measured by scintillation counting. Non-specific binding was calculated by the radioactivities measured under the incubations in the presence of 0.1 mM D-serine. The [$^3$H] glycine binding was not inhibited by addition of 0.1 mM strychnine.

[$^3$H] MK-801 binding studies

A crude frozen rat brain membrane preparation was thawed and washed once by centrifugation at 50,000× g for 30 min with 50 mM tris acetate (pH 7.4). The pellet obtained (ca. 200–300 μg protein) was incubated with 5 nM [$^3$H] MK-801 (29.4 Ci/mmol) and the test compound (10 μg/mL–100 ng/mL) at 30° C. for 30 min in 50 mM tris acetate (pH 7.4). The incubation was terminated by suction filtration using Whatman GF/B glass filter. The radioactivities bound to the membrane on the filter was measured by scintillation counting. Non-specific binding was calculated by the radioactivities measured under the incubations in the presence of 0.1 mM MK-801.

BEST MODE FOR CARRYING OUT OF THE INVENTION

The preparation of the compounds of the present invention is illustrated by the following examples but should not be construed to be limited thereto.

EXAMPLE 1

8-Bromo-5,6-dihydro-1H-pyrrolo[1,2,3-de]quinoxaline-2,3-dione

1) N-Ethoxalylindoline

To a solution of indoline (2.0 g, 16.8 mmol) and triethylamine (5 mL) in dichloromethane (30 mL) was added slowly ethyl chlorooxalate (2.3 mL, 20.1 mmol) at 0° C. The mixture was stirred for 10 min at 0° C. and then for 1 h at room temperature. Brine was added and organic layer was separated. The organic layer was washed with diluted aqueous hydrochloric acid and successively brine, dried over magnesium sulfate, and concentrated to give 4.0 g of N-ethoxalylindoline (100%): $^1$H NMR (270 MHz, CDCl$_3$) δ8.18 (dd, 1H, J=8, 1 Hz), 7.22 (m, 2H), 7.10 (dd, 1H, J=8, 1 Hz), 4.38 (q, 2H, J=7 Hz), 4.22 (t, 2H, J=8 Hz), 3.20 (t, 2H, J=8 Hz), 1.40 (t, 3H, J=7 Hz).

2) 5-Bromo-N-ethoxalylindoline

To a mixture of N-ethoxalylindoline (4 g, 18.3 mmol), and iron powder (0.40 g) in dichloromethane (40 mL) was added dropwise bromine (1.43 mL, 27.7 mmol) at 0° C. The mixture was stirred for 4 h at room temperature and filtered. The filtrate was washed with aqueous sodium thiosulfate and then brine, dried over magnesium sulfate, and concentrated to give 5.24 g of 5-bromo-N-ethoxalylindoline (95%): $^1$H NMR (270 MHz, CDCl$_3$) δ8.07(d, 1H, J=8 Hz), 7.35 (dd, 2H, J=8, 1 Hz), 4.38 (q, 2H, J=7 Hz), 4.27 (t, 2H, J=8 Hz), 3.20 (t, 2H, J=8 Hz), 1.41 (t, 3H, J=7 Hz).

3) 5-Bromo-7-nitro-N-ethoxalylindoline

To a solution of 5-bromo-N-ethoxalylindoline (5.23 g, 17.5 mmol) in concentrated sulfuric acid was added slowly isopropyl nitrate (1.87 mL, 18.5 mmol) at 0° C. The mixture was stirred for 1 h at 0° C. and poured into a mixture of water and crashed ice. The mixture was extracted with ethyl acetate and the organic layer was washed with brine, dried over magnesium sulfate, and concentrated. The crude residue was purified by silica gel column chromatography to give 5.02 g of 5-bromo-7-nitro-N-ethoxalylindoline (83%): $^1$H NMR (270 MHz, CDCl$_3$) δ7.91 (d, 1H, J=1 Hz), 7.62 (d, 1H, J=1 Hz), 4.39 (t, 2H, J=8 Hz), 4.38 (q, 2H, J=7 Hz), 3.22 (t, 2H, J=8 Hz), 1.39 (t, 3H, J=7 Hz).

4) 8-Bromo-5,6-dihydro-1H-pyrrolo[1,2,3-de]quinoxaline-2,3-dione

To a solution of 5-bromo-7-nitro-N-ethoxalylindoline (2.0 g, 5.83 mmol) in a mixture of THF (50 mL), water (10 mL), and acetic acid (10 mL) was added aqueous 20% titanium trichloride (31 mL, 40.8 mmol) and the mixture was stirred for 4 h at room temperature. The precipitates formed were collected by filtration, washed with diluted aqueous hydrochloric acid and then distilled water, and dried in vacuo to give 772 mg of the title compound (50%): mp>300° C.; $^1$H NMR (270 MHz, DMSO-d$_6$) δ11.91 (bs, 1H), 7.21 (d, 1H, J=1 Hz), 7.02 (d, 1H, J=1 Hz), 4.22 (t, 2H, J=7 Hz), 3.32 (t, 2H, J=7 Hz).

EXAMPLE 2

8-Bromo-5-methoxycarbonyl-5,6-dihydro-1H-pyrrolo[1,2,3-de]quinoxaline-2,3-dione

The title compound was prepared by the route outlined in Example 1 starting with 2-methoxycarbonylindoline: mp 266.5°–267.5° C. (dec); $^1$H NMR (270 MHz, DMSO-d$_6$) δ12.11 (bs, 1H), 7.24 (d, 1H, J=1 Hz), 7.09 (d, 1H, J=1 Hz), 5.31 (dd, 1H, J=11, 5 Hz), 3.79 (dd, 1H, J=17, 11 Hz), 3.73 (s, 3H), 3.39 (dd, 1H, J=17, 5 Hz).

EXAMPLE 3

8-Bromo-5-carboxy-5,6-dihydro-1H-pyrrolo[1,2,3-de]quinoxaline-2,3-dione

To a solution of 8-bromo-5-methoxycarbonyl-5,6-dihydro-1H-pyrrolo[1,2,3-de]quinoxaline-2,3-dione (256 mg, 0.76 mmol) in a mixture of THF (5 mL) and methanol (5 mL) was added aqueous 1N NaOH (2.5 mL) and the mixture was stirred for 12 h at room temperature. Aqueous 1N HCl was added and the resulting mixture was concentrated to ca. 5 mL. The precipitates formed were collected by filtration, washed with distilled water, and dried in vacuo to give 256 mg of the title compound (quant): mp 285° C. (dec); $^1$H NMR (270 MHz, DMSO-d$_6$) δ13.45 (bs, 1H), 12.09 (s, 1H), 7.22 (d, 1H, J=1Hz), 7.08 (d, 1H, J=1 Hz), 5.18 (dd, 1H, J=11, 4 Hz), 3.79 (dd, 1H, J=17, 11 Hz), 3.33 (dd, 1H, J=17, 4 Hz).

EXAMPLE 4

8-Bromo-5-phthalimidomethyl-5,6-dihydro-1H-pyrrolo[1,2,3-de]quinoxaline-2,3-dione 1) 2-Carbamoylindoline To a solution of 2-methoxycarbonylindoline (22.733 g, 0.128 mmol) in methanol (230 mL) was introduced gaseous NH$_3$ at room temperature until the solution was saturated with NH$_3$. The mixture was stirred for 6 h at room temperature. The precipitates formed were collected, washed with methanol, and dried in vacuo to give 17.78 g of 2-carbamoylindoline (85%): $^1$H NMR (270 MHz, CDCl$_3$) δ7.30 (bs, 1H), 7.11 (bs, 1H), 7.01 (d, 1H, J=7 Hz), 6.93 (dt, 1H, J=1, 7 Hz), 6.56 (m, 2H), 5.87 (bs, 1H), 4.12 (dd, 1H, J=10, 8 Hz), 3.25 (dd, 1H, J=16, 10 Hz), 2.93 (dd, 1H, J=16, 8 Hz).

2) 2-Aminomethylindoline

To a suspension of LiAlH$_4$ (6.0 g, 0.157 mol) in THF (200 mL) was added dropwise a suspension of 2-carbamoylindoline (17.0 g, 0.105 mol) in THF (700 mL) over 50 min. The mixture was refluxed for 5 h and then LiAlH$_4$ (6.0 g) was added further. The reflux was continued additionally for 6 h and the mixture was treated with 10% aqueous THF after being cooled with ice bath. Aqueous 1N NaOH was added and the mixture was extracted with a mixture of diethyl ether and THF. The organic layer was washed with water and brine, dried over magnesium sulfate, and concentrated to give 13.91 g of 2-aminomethylindoline (90%): $^1$H NMR (270 MHz, CDCl$_3$) δ7.11 (dd, 1H, J=7, 1 Hz), 7.01 (dt, 1H, J=1, 7 Hz), 6.68 (dt, 1H, J=1, 7 Hz), 6.61 (d, 1H, J=7 Hz), 3.84 (m, 1H), 3.11 (dd, 1H, J=16, 9 Hz), 2.86 (dd, 1H, J=13, 5 Hz), 2.70 (m, 2H).

3) 2-Phthalimidomethylindoline

A mixture of 2-aminomethylindoline (6.0 g, 40.48 mmol) and phthalic anhydride (6.30 g, 42.51 mmol) in toluene (600 mL) was refluxed for 4 h, while water generated during the reaction was removed by azeotropic distillation by using Dean-Stark apparatus. The mixture was concentrated to give a crude 2-phthalimidomethylindoline (11.84 g), which was used for the next step without further purification: $^1$H NMR (270 MHz, CDCl$_3$) δ7.82 (m, 2H), 7.71 (m, 2H), 7.03 (d, 1H, J=7 Hz), 6.95 (dt, 1H, J=1,7 Hz), 6.61 (m, 2H), 4.19 (m, 1H), 3.86 (d, 2H, J=6 Hz), 3.18 (dd, 1H, J=16, 9 Hz), 2.93 (dd, 1H, J=16, 6 Hz).

4) 8-Bromo-5-phthalimidomethyl-5,6-dihydro-1H-pyrrolo-[1,2,3-de]quinoxaline-2,3-dione The title compound was prepared from 2-phthalimidomethylindoline by the route outlined in Example 1: mp 267° C. (dec); $^1$H NMR (270 MHz, DMSO-d$_6$) δ11.91 (s, 1H), 7.83 (bs, 4H), 7.15 (d, 1H, J=1 Hz), 6.99 (d, 1H, J=1 Hz), 5.13–5.26 (m, 1H), 4.07 (dd, 1H, J=14, 6 Hz), 3.99 (dd, 1H, 14, 5 Hz), 3.50 (dd, 1H, J =17, 10 Hz), 3.11 (dd, 1H, J=17, 3 Hz).

EXAMPLE 5

8-Bromo-5-benzylcarbamoyl-5,6-dihydro-1H-pyrrolo[1,2,3-de]quinoxaline-2,3-dione

To a solution of 8-bromo-5-carboxy-5,6-dihydro-1H-pyrrolo[1,2,3-de]quinoxaline- 2,3-dione (300 mg, 0.96 mmol) and benzylamine (114 mg, 1.06 mmol) in DMF (3 mL) was added 1-ethyl-3-(3'-dimethylaminopropyl)carbodiimide (164 mg, 1.06 mmol) and N-hydroxybenztriazole (162 mg, 1.06 mmol) at 0° C. The mixture was stirred at room temperature overnight and aqueous 0.1N HCl was added. The precipitates formed were collected by filtration, washed with distilled water, and dried in vacuo to give 384 mg of the title compound (99%): mp 152.5°~153° C.; $^1$H NMR (270 MHz, DMSO-$d_6$) δ12.01 (s, 1 H), 11.52 (t, 1H, J=5.6 Hz), 7.34 (m, 5H), 7.21 (d, 1H, J=1 Hz), 7.07 (d, 1H, J=1 Hz), 5.17 (dd, 1H, J=17, 10 Hz), 4.32 (d, 2H, J=5.6 Hz), 3.74 (dd, 1H, J=17, 10 Hz), 3.20 (dd, 1H, J=17, 5 Hz).

EXAMPLE 6

8-Bromo-5-(2-phenylethylcarbamoyl)-5,6-dihydro-1H-pyrrolo[1,2,3-de]quinoxaline-2,3-dione A procedure similar to that described in Example 5 was carried out with 8-bromo-5-carboxy-5,6-dihydro-1H-pyrrolo[1,2,3-de]quinoxaline-2,3-dione (300 mg, 0.96 mmol) and β-phenethylamine (133 μL, 1.061 mmol) to give 383 mg of the title compound (96%): mp 246°~249° C. (dec); $^1$H NMR (270 MHz, DMSO-$d_6$) δ12.01 (s, 1H), 8.41 (t, 1H, J=5.6 Hz), 7.25 (m, 5H), 7.22 (d, 1H, J=1 Hz), 7.07 (d, 1H, J=1 Hz), 5.07 (dd, 1H, J=10, 5 Hz), 3.65 (dd, 1H, J=17, 10 Hz), 3.30 (dt, 2H, J=5.6, 7 Hz), 3.04 (dd, 1H, J=17, 5 Hz), 2.71 (t, 2H, J=7 Hz).

EXAMPLE 7

8-Bromo-5-(phenylcarbamoyl)-5,6-dihydro-1H-pyrrolo[1,2,3-de]quinoxaline-2,3-dione A procedure similar to that described in Example 5 was carried out with 8-bromo-5-carboxy-5,6-dihydro-1H-pyrrolo[1,2,3-de]quinoxaline-2,3-dione (300 mg, 0.96 mmol) and aniline (97 μL, 1.061 mmol) to give 274 mg of the title compound (74%): mp>300° C.; $^1$H NMR (270 MHz, DMSO-$d_6$) δ12.09 (s, 1H), 10.45 (s, 1H), 7.59 (d, 2H, J=7.5 Hz), 7.34 (t, 2H, J=7.5 Hz), 7.23 (d, 1H, J=1 Hz), 7.10 (t, 1H, J=7.5 Hz), 7.07 (d, 1H, J=1 Hz), 5.31 (dd, 1H, J=10, 5 Hz), 4.32 (d, 2H, J=5.6 Hz), 3.78 (dd, 1H, J=17, 10 Hz), 3.35 (dd, 1H, J=17, 5 Hz),

EXAMPLE 8

8-Bromo-5-aminomethyl-5,6-dihydro-1H-pyrrolo[1,2,3-de]quinoxaline-2,3-dione hydrochloride A solution of 8-bromo-5-phthalimidomethyl-5,6-dihydro-1H-pyrrolo[1,2,3-de]quinoxaline-2,3-dione (100 mg)in a mixture of acetic acid (6 mL) and concentrated HCl (6 mL) was refluxed for 4.5 h and concentrated. The residue was triturated with methylenechloride containing a small amount of methanol. The precipitates were collected by filtration, rinsed with methylenechloride, and dried in vacuo to give 60 mg of the title compound (60%): mp 268° C. (dec); $^1$H NMR (270 MHz, DMSO-$d_6$) δ11.98 (s, 1H), 8.07 (br, 3H), 7.23 (d, 1H, J=1 Hz), 7.07 (d, 1H, J=1 Hz), 5.02~5.12 (m, 1H), 3.56 (dd, 1H, J=17, 10 Hz), 3.28~3.48 (m, 2H), 3.11 (dd, 1H, J=17, 3 Hz).

EXAMPLE 9

8-Bromo-5-methoxycarbonylmethyl-5,6-dihydro-1H-pyrrolo[1,2,3-de]quinoxaline-2,3-dione 1) 2-Hydroxymethylindoline To a suspension of LiAlH$_4$ (4.65 g, 0.122 mol) in THF (100 mL) was added dropwise 2-methoxycarbonylindoline (10.85 g, 0.0613 mol) in THF 260 mL at room temperature. The mixture was refluxed for 3.5 h and then excess reagent was decomposed by addition of aqueous THF. To the mixture was added 1N aqueous NaOH (50 mL), water (100 mL), and diethyl ether (100 mL), successively. The organic layer was separated, washed with brine, dried over magnesium sulfate, and concentrated to give 8.77 g of 2-hydroxymethylindoline (96%): $^1$H NMR (270 MHz, CDCl$_3$) δ7.08 (d, 1H, J=7 Hz), 7.02 (t, 1H, J=7 Hz), 6.71 (t, 1H, J=7 Hz), 6.64 (d, 1H, J=7 Hz), 4.02 (m, 1H), 3.70 (dd, 1H, J=11, 4 Hz), 3.56 (dd, 1H, J=11, 7 Hz), 3.09 (dd, 1H, J=16, 9 Hz), 2.81 (dd, 1H, J=16, 8 Hz).

2) 2-Cyanomethylindoline

To a mixture of 2-hydroxymethylindoline (7.77 g, 52.08 mmol), imidazole (8.86g, 130.2 mmol), triphenylphosphine (34.15 g, 130.2 mmol)in toluene (500 mL) was added iodine (26.44 g, 104.16 mmol) in acetonitrile (100 mL) at 0° C. The mixture was stirred for 10 min and water was added. The organic layer was separated, washed with brine, dried over magnesium sulfate, and concentrated. The residue was triturated with diethyl ether and insoluble solids were removed by filtration. The filtrate was concentrated to give crude 2-iodomethylindoline. The crude 2-iodomethylindoline was dissolved in DMF (130 mL) and KCN (4.07 g, 62.5 mmol) was added. The mixture was heated at 80° C. for 12 h and after addition of KCN (4.07 g), the heating was further continued for 5 h. The mixture was poured into saturated aqueous sodium bicarbonate and extracted with ethyl acetate. The organic layer was washed with brine, dried over magnesium sulfate, and concentrated. The residue was purified by silica gel column chromatography with 3:1 to 2:1 hexane/ethyl acetate to give 3.04 g of 2-cyanomethylindoline (37%): $^1$H NMR (270 MHz, CDCl$_3$) δ7.03 (m, 2 H), 6.77 (t, 1H, J=7 Hz), 6.54 (t, 1H, J=7 Hz), 4.42 (m, 1H), 4.13 (bs, 1H), 3.07 (m, 1H), 2.81 (dt, 1H, J=16, 4 Hz), 2.22 (m, 2H).

3) 2-Methoxycarbonylmethylindoline

A solution of 2-cyanomethylindoline (2.95 g, 18.65 mmol) in concentrated HCl (15 mL) was refluxed for 1 h and the mixture was concentrated in vacuo. The residue was dissolved in methanol (50 mL) and thionyl chloride (2.5 mL, 33.99 mmol) was added slowly at 0° C. The mixture was heated at 50° C. for 2.5 h and the solvent was removed in vacuo. The residue was dispersed between ethyl acetate and saturated aqueous sodium bicarbonate and the organic layer was separated, washed with brine, dried over magnesium sulfate, and concentrated to give 2.22 g of 2-methoxycarbonylmethylindoline (62%): $^1$H NMR (270 MHz, CDCl$_3$) δ6.99 (t, 1H, J=7.6 Hz), 6.95 (d, 1H, J=7.6 Hz), 6.64 (td, 1H, J=7.6, 1 Hz), 6.58 (d, 1H, J=7.6 Hz), 4.35 (bs, 1H), 4.03 (dd, 1H, J=8.9, 4 Hz), 3.77 (s, 3H), 2.74~2.82 (m, 2H), 2.22~2.33 (m, 1H), 1.93~2.06 (m, 1H).

4) 8-Bromo-5-methoxycarbonylmethyl-5,6-dihydro-1H-pyrrolo[1,2,3-de]quinoxaline-2,3-dione The title compound was prepared by the route outlined in Example 1 starting with 2-methoxycarbonylmethylindoline: mp 244.5°~248° C. (dec); $^1$H NMR (270 MHz, DMSO-$d_6$) δ12.26 (s, 1H), 7.21 (s, 2H), 5.29~5.35 (m, 1H), 3.70 (s, 3H), 2.87 (dm, 1H, J=18 Hz), 2.60 (dm, 1H, J=14 Hz), 2.46 (m, 1H, J=14 Hz), 2.00~2.16 (m, 1H).

EXAMPLE 10

8-Bromo-5-carboxymethyl-5,6-dihydro-1H-pyrrolo[1,2,3-de]quinoxaline-2,3-dione Hydrolysis of 8-bromo-5-methoxycarbonylmethyl-5,6-dihydro-1H-pyrrolo[1,2,3-de]quinoxaline-2,3-dione (680 mg, 2.01 mmol) was carried out as described in Example 3 to give 640 mg of the title compound (98%): mp 265° C. (dec); $^1$H NMR (270 MHz, DMSO-$d_6$) δ13.38 (br, 1H), 12.23 (s, 1H), 7.20 (s, 2H), 5.19~5.25 (m, 1H), 2.88 (dm, 1H, J=18 Hz), 2.63 (dm, 1H, J=14 Hz), 2.43 (m, 1H, J=14 Hz), 1.96~2.12 (m, 1H).

EXAMPLE 11

8-Bromo-5-carbamoylmethyl-5,6-dihydro-1H-pyrrolo[1,2,3-de]quinoxaline-2,3-dione

To a solution of 8-bromo-5-carboxymethyl-5,6-dihydro-1H-pyrrolo[1,2,3-de]quinoxaline-2,3-dione (100 mg, 0.308 mmol) in DMF (2 mL) in the presence of triethylamine (64 µL, 0.461 mmol) was added isobutyl chloroformate (44 µL, 0.338 mmol) at −20° C. After being stirred for 10 min, aqueous 28% ammonia (94 µL, 1.538 mmol) was added at −20° C. The stirring was continued for 30 min at room temperature and 0.1N hydrochloric acid (20 mL) was added. The precipitates formed were collected by filtration, washed with water, and again suspended in aqueous sodium bicarbonate. The suspension was adjusted to pH 7.0 by addition of 1N hydrochloric acid and extracted with 2:1 ethyl acetate/THF. The organic layer was washed with brine, dried over magnesium chloride, and concentrated. The residual solids were rinsed with dichloromethane to give 14 mg of the title compound (14%): mp>300° C.; $^1$H NMR (270 MHz, DMSO-d$_6$) δ12.10 (bs, 1H), 7.66 (s, 1H), 7.29 (s, 1H), 7.17 (s, 2H), 5.04~5.10 (m, 1H), 2.80 (dm, 1H, J=18 Hz), 2.58 (dm, 1H, J=14 Hz), 2.41 (m, 1H, J=14 Hz), 1.85~2.00 (m, 1H).

EXAMPLE 12

8-Bromo-5-phenylcarbamoylmethyl-5,6-dihydro-1H-pyrrolo[1,2,3-de]quinoxaline-2,3-dione A procedure similar to that described in Example 5 was carried out with 8-bromo-5-carboxymethyl-5,6-dihydro-1H-pyrrolo[1,2,3-de]quinoxaline-2,3-dione (130 mg, 0.40 mmol) and aniline (40 µL, 0.44 mmol) to give 82 mg of the title compound (51%): mp 186° C. (dec); $^1$H NMR (270 MHz, DMSO-d$_6$) δ12.23 (s, 1H), 10.34 (s, 1H), 7.55 (d, 2H, J=8 Hz), 7.32 (t, 2H, J=8 Hz), 7.22 (s, 2H), 7.07 (t, 1H, J=8 Hz), 5.30~5.36 (m, 1H), 2.86 (dm, 1H, J=18 Hz), 2.75 (dm, 1H, J=14 Hz), 2.62 (m, 1H, J=14 Hz), 2.02~2.18 (m, 1H).

EXAMPLE 13

8-Bromo-5-benzylcarbamoylmethyl-5,6-dihydro-1H-pyrrolo[1,2,3-de]quinoxaline-2,3-dione A procedure similar to that described in Example 5 was carried out with 8-bromo-5-carboxymethyl-5,6-dihydro-1H-pyrrolo[1,2,3-de]quinoxaline-2,3-dione (130 mg, 0.40 mmol) and benzylamine (48 µL, 0.44 mmol) to give 82 mg of the title compound (51%): mp 252° C. (dec); $^1$H NMR (270 MHz, DMSO-d$_6$) δ12.13 (s, 1H), 8.69 (t, 1H, J=6 Hz), 7.18~7.34 (m, 5H), 7.20 (s, 2H), 5.16~5.22 (m, 1H), 4.27 (d, 2H, J=6 Hz), 2.80 (dm, 1H, J=18 Hz), 2.55 (dm, 1H, J=14 Hz), 2.46 (m, 1H, J=14 Hz), 1.87~2.03 (m, 1H).

EXAMPLE 14

8-Bromo-5-(N'-phenylureidomethyl)-5,6-dihydro-1H-pyrrolo[1,2,3-de]quinoxaline-2,3-dione A mixture of 8-bromo-5-aminomethyl-5,6-dihydro-1H-pyrrolo[1,2,3-de]quinoxaline- 2,3-dione hydrochloride (134 mg, 0.405 mmol), triethylamine (136 µL, 0.972 mmol), and phenyl isocyanate (53 mL, 0.486 mmol) in DMF (2 mL) was stirred for 3 h and 0.1N hydrochloric acid (20 mL) was added. The precipitates formed were collected by filtration, washed with distilled water, and dried in vacuo. The precipitates were rinsed with dichloromethane containing a small amount of methanol to give 79 mg of the title compound (47%): mp 175°~179° C. (dec); $^1$H NMR (270 MHz, DMSO-d$_6$) δ11.93 (bs, 1H), 8.31 (s, 1H), 7.31 (d, 2 H, J=8 Hz), 7.19 (s, 1H), 7.18 (t, 2H, J=8 Hz), 7.01 (s, 1H), 6.87 (t, 1H, J=8 Hz), 6.42 (t, 1H, J=6 Hz), 4.86~4.95 (m, 1H), 3.63~3.75 (m, 2H), 3.45 (dd, 1H, J=17, 10 Hz), 3.19 (dd, 1H, J=17, 4 Hz)

EXAMPLE 15

8-Bromo-5-benzoylaminomethyl-5,6-dihydro-1H-pyrrolo[1,2,3-de]quinoxaline-2,3-dione A mixture of 8-bromo-5-aminomethyl-5,6-dihydro-1H-pyrrolo[1,2,3-de]quinoxaline-2,3-dione hydrochloride (134 mg, 0.405 mmol), triethyl amine (124 µL, 0.892 mmol), benzoic acid (54 mg, 0.446 mmol), 1-ethyl-3-(3'-dimethylaminopropyl)carbodiimide (69 mg, 0.446 mmol) and N-hydroxybenzotriazole (68 mg, 0.446 mmol) in DMF (6 mL) was stirred for 20 h at room temperature and 0.1N hydrochloric acid (20 mL) was added. The precipitates formed were collected by filtration, washed with distilled water, and dried in vacuo to give 87 mg of the title compound (52%): mp 180.5°~182° C.; $^1$H NMR (270 MHz, DMSO-d$_6$) δ11.86 (s, 1H), 8.56 (t, 1H, J=6 Hz), 7.34~7.54 (m, 5H), 7.12 (s, 1H), 7.17 (s, 2H), 4.96~5.06 (m, 1H), 3.90~4.00 (m, 1H), 3.72~3.82 (m, 1H), 3.43 (dd, 1H, J=17, 10 Hz), 3.19 (dd, 1H, J=17, 3 Hz).

EXAMPLE 16

8-Bromo-5-(N-hydroxycarbamoylmethyl)-5,6-dihydro-1H-pyrrolo[1,2,3-de]quinoxaline-2,3-dione To a solution of 8-bromo-5-carboxymethyl-5,6-dihydro-1H-pyrrolo[1,2,3-de]quinoxaline-2,3-dione (100 mg, 0.308 mmol) in DMF (2 mL) in the presence of triethylamine (64 µL, 0.461 mmol) was added isobutyl chloroformate (44 µL, 0.338 mmol) at −20° C. After being stirred for 10 min, a mixture of hydroxylamine, hydrochloride (43 mg, 0.615 mmol) and triethylamine (107 µL, 0.769 mmol) in 10:1 DMF/water (1.1 mL) was added at −20° C. The stirring was continued for 30 min at room temperature and 0.1N hydrochloric acid (20 mL) was added. The precipitates formed were collected by filtration, washed with water, and again suspended in aqueous sodium bicarbonate. The suspension was adjusted to pH 7.0 by addition of 1N hydrochloric acid and extracted with 2:1 ethyl acetate/THF. The organic layer was washed with brine, dried over magnesium chloride, and concentrated. The residual solids was rinsed with dichloromethane to give 15 mg of the title compound (14%): mp 249.5° C. (dec); $^1$H NMR (270 MHz, DMSO-d$_6$) δ12.08 (bs, 1H), 10.78 (s, 1H), 8.96 (s, 1H), 7.17 (s, 2H), 5.04~5.10 (m, 1H), 2.80 (dm, 1H, J=18 Hz), 2.60 (dm, 1H, J=14 Hz), 2,39 (m, 1H, J=14 Hz), 1.83~1.98 (m, 1H).

EXAMPLE 17

9-Bromo-5-methoxycarbonyl-6,7-dihydro-1H,5H-pyrido[1,2,3-de]-quinoxaline-2,3-dione The title compound was prepared by the route outlined in Example 1 starting with 2-methoxycarbonyltetrahydroquinoline: mp 240° C.; $^1$H NMR (270 MHz, DMSO-d$_6$) δ12.24 (bs, 1H), 7.21 (bs, 2H), 5.30 (dd, 1H, J=4, 6 Hz), 3.72

(s, 3H), 2.88 (bd, 1H, J=16 Hz), 2.5~2.63 (m, 1H), 2.4~2.46 (m, 1H), 2.03~2.14 (m, 1H).

EXAMPLE 18

9-Bromo-5-carboxy-6,7-dihydro-1H, 5H-pyrido[1,2, 3-de]quinoxaline-2,3-dione

A procedure similar to that described in Example 3 was carried out with 9-bromo-5-methoxycarbonyl-6,7-dihydro-1H, 5H-pyrido[1,2,3-de]-quinoxaline-2,3-dione (1.5 g, 4.42 mmol) to give 1.45 g of the title compound (quant): mp>270° C.; $^1$H NMR (270 MHz, DMSO-d$_6$) δ12.23 (bs, 1H), 7.20 (bs, 2H), 5.21 (m, 1H), 2.89 (dm, 1H, J=16.8 Hz), 2.37~2.65 (m, 2H), 1.98~2.11 (m, 1H).

EXAMPLE 19

9-Bromo-5-phenylcarbamoyl-6,7-dihydro-1H, 5H-pyrido[1,2,3-de]quinoxaline-2,3-dione A procedure similar to that described in Example 5 was carried out with 9-bromo-5-carboxy-6,7-dihydro-1H, 5H-pyrido[1,2,3-de]quinoxaline-2,3-dione (300 mg, 0.92 mmol) and aniline (93 mg, 1.0 mmol) to give 31 0 mg of the title compound (84%): mp>250° C.; $^1$H NMR (270 MHz, DMSO-d$_6$) δ12.25 (s, 1H), 10.36 (s, 1H), 7.56 (d, 2H, J=8 Hz), 7.33 (t, 2H, J=8.0 Hz), 7.24 (bs, 1H), 7.22 (bs, 1H), 7.09 (t, 1H, J=8 Hz), 5.32~5.36 (m, 1H), 2.89 (dm, 1H, J=16.8 Hz), 2.58~2.81 (m, 2H), 2.05~2.22 (m, 1H).

EXAMPLE 20

9-Bromo-5-benzylcarbamoyl-6,7-dihydro-1H, 5H-pyrido[1,2,3-de]quinoxaline-2,3-dione A procedure similar to that described in Example 5 was carried out with 9-bromo-5-carboxy-6,7-dihydro-1H, 5H-pyrido[1,2,3-de]quinoxaline-2,3-dione (300 mg, 0.92 mmol) and benzylamine (107 mg, 1.0 mmol) to give 310 mg of the title compound (81%): mp>250° C.; $^1$H NMR (270 MHz, DMSO-d$_6$) δ12.12 (s, 1H), 8.68 (t, 1H, J=6.1 Hz), 7.12~7.31 (m, 7H), 5.13~5.19 (m, 1H), 4.26 (d, 2H, J=6.1 Hz), 2.78 (dm, 1H, J=16.8 Hz), 2.39~2.61 (m, 2H), 1.85~2.00 (m, 1H).

EXAMPLE 21

9-Bromo-5-phenethylcarbamoyl-6,7-dihydro-1H, 5H-pyrido[1,2,3-de]quinoxaline-2,3-dione A procedure similar to that described in Example 5 was carried out with 9-bromo-5-carboxy-6,7-dihydro-1H, 5H-pyrido[1,2,3-de]quinoxaline-2,3-dione (300 mg, 0.92 mmol) and phenethylamine (121 mg, 1.0 mmol) to give 330 mg of the title compound(84%): mp>250° C.; $^1$H NMR (270 MHz, DMSO-d$_6$) δ12.12 (s, 1H), 8.21 (t, 1H, J=5.6 Hz), 7.09~7.39 (m, 7H), 5.07 (m, 1H), 3.24~3.33 (m, 2H), 2.64~2.73 (m, 3H), 2.25~2.32 (m, 2H), 1.80~1.95 (m, 1H).

EXAMPLE 22

9-Bromo-5-methoxycarbonylmethyl-6,7-dihydro-1H, 5H-pyrido[1,2,3-de]quinoxaline-2,3-dione 1) 2-Hydroxymethyltetrahydroquinoline Reduction of 2-methoxycarbonyltetrahydroquinoline (34.15 g, 0.15 mol) was performed as described in Example 9-1 to give 28.1 g of 2-hydroxymethyltetrahydroquinoline (quant): $^1$H NMR (270 MHz, CDCl$_3$) δ6.95~7.00 (m, 2H), 6.63 (t, 1H, J=7.4 Hz), 6.54 (d, 1H, J=7.4 Hz), 3.74 (dd, 1H, J=10.2, 3.6 Hz), 3.56 (dd, 1H, J=10.2, 8.6 Hz), 3.41~3.49 (m, 1H), 2.70~2.85 (m, 2H), 1.85~1.90 (m, 1H), 1.68~1.77 (m, 1H).

2) 2-Cyanomethyltetrahydroquinoline

To a solution of 2-hydroxymethyltetrahydroquinoline (54 g, 0.33 mol), imidazole (56 g, 0.825 mol), and triphenylphosphine (216 g, 0.825 mol) in a mixed solvent of 10:1 toluene/acetonitrile (2.2 L) was added iodine (167 g, 0.66 mol) at room temperature. The mixture was stirred for 30 min at the same temperature and aqueous sodium thiosulfate solution (300 mL) was added. The organic layer was separated, washed with brine, dried over magnesium sulfate, and concentrated. The residue was triturated with diethyl ether and the insoluble materials were removed by filtration. The filtrate was concentrated and the residual oil was dissolved in DMF (600 mL). To the solution was added sodium cyanide (33 g, 0.67 mol) and the mixture was heated at 80° C. for 4 h. The resulting mixture was poured into ice-water and extracted with ether. The organic layer was washed with brine, dried over magnesium sulfate, and concentrated to give 140 g of a crude product which was used for the next step without purification. The specimen for characterization was obtained by silica gel column chromatography of the crude product with 1:1 hexane/dichloromethane to 100% dichloromethane as eluent: $^1$H NMR (270 MHz, CDCl$_3$) δ6.97~7.04 (m, 2H), 6.68 (t, 1H, J=7.4 Hz), 6.54 (d, 1H, J=7.4 Hz), 4.03 (br, 1H), 3.70 (m, 1H), 2.70~2.86 (m, 2H), 2.54 (d, 1H, J=6.6 Hz), 2.02~2.13 (m, 1H), 1.78~1.91 (m, 1H).

3) 2-Methoxycarbonylmethyltetrahydroquinoline hydrochloride

The crude 2-cyanomethyltetrahydroquinoline (140 g) obtained above was dissolved in concentrated hydrochloric acid (280 mL) and the mixture was refluxed for 5 h. Concentrated hydrochloric acid (80 mL) was added further and the reflux was continued for 1 h. The mixture was diluted with water (500 mL) and extracted with ethyl acetate (500 mL×2). The organic layers were discarded after being washed with 3N hydrochloric acid solution. The combined aqueous layers were adjusted to pH 3 by using aqueous sodium hydroxide and extracted with dichloromethane (500 and 300 mL). The organic layers was washed with brine, dried over magnesium sulfate, and concentrated. The residue (80 g) was dissolved in methanol (500 mL) and thionyl chloride (48 mL) was added slowly at 0° C. The mixture was stirred overnight at room temperature and concentrated. The precipitates formed were rinsed with acetone and dried in vacuo to give 43 g of the title compound (54%): $^1$H NMR (270 MHz, CDCl$_3$) δ7.69~7.72 (m, 1H), 7.23~7.38 (m, 3H), 3.96~4.05 (m, 1H), 3.75 (s, 3H), 3.48~3.55 (m, 1H), 2.96~3.12 (m, 3H), 2.19~2.41 (m, 1H).

4) 6-Bromo-2-methoxycarbonylmethyltetrahydroquinoline

In a mixture of aqueous solution of potassium carbonate (30 g) and ethyl acetate was dispersed 2-methoxycarbonylmethyltetrahydroquinoline hydrochloride (24.8 g, 0.1 mol). The organic layer was separated, dried over magnesium sulfate, and concentrated. The residue was dissolved in DMF (400 mL) and a solution of N-bromosuccinimide (21.36 g, 0.12 mol)in DMF (400 mL) was added dropwise at 0° C. The mixture was stirred for 5 h at room temperature, poured into water (250 mL), and extracted with ether (250 mL). The organic layer was washed with water, dried over magnesium sulfate, and concentrated to give 36 g of the crude title compound (quant) which was used for the next step without purification. The specimen for characterization was obtained by silica gel column chromatography of the crude compound with 1:1 dichloromethane/hexane to 100% dichloromethane: $^1$H NMR (270 MHz, CDCl$_3$) δ7.02~7.06 (m, 2H), 6.38 (dd, 1H, J=1.7, 7.3 Hz), 4.53 (br, 1H), 3.75 (s, 3H), 3.72~3.75 (m, 4H), 2.70~2.85 (m, 2H), 2.49~2.53 (m, 1H), 1.89~1.99 (m, 1H), 1.61~1.75 (m, 1H).

5) 6-Bromo-2-methoxycarbonylmethyl-N-ethoxalyltetrahydroquinoline

A procedure similar to that described in Example 1-1 was carried out with 6-bromo-2-methoxycarbonylmethyltetrahydroquinoline obtained above (36 g) to give 40 g of the title compound (quant): $^1$H NMR (270 MHz, CDCl$_3$) δ7.36 (s, 1H), 7.30 (d, 1H, J=8.3 Hz), 6.92 (d, 1H, J=8.3 Hz), 4.94~5.01 (m, 1H), 4.13~4.16 (m, 2H), 3.64 (s, 3H), 2.43~2.75 (m, 6H), 1.11~1.26 (m, 3H).

6) 6-Bromo-2-methoxycarbonylmethyl-8-nitro-N-ethoxalyltetrahydroquinoline

To a refluxed solution of 6-bromo-2-methoxycarbonylmethyl-N-ethoxalyltetrahydroquinoline (40 g) and ammonium nitrate (8 g, 0.1 mol) in chloroform (100 mL) was added dropwise trifluoroacetic anhydride (56.5 mL, 0.4 mol) over 40 min. The reflux was continued for 90 min and crashed ice was added. The organic layer was separated, washed with saturated aqueous sodium bicarbonate and brine, dried over magnesium sulfate, and concentrated to give 46 g of the title compound (quant): $^1$H NMR (270 MHz, CDCl$_3$) δ8.11 and 7.99 (d and d, 1H, J=2 Hz), 7.66 and 7.61 (d and d, 1H, J=2 Hz), 5.03~5.16 and 4.74~4.85 (m and m, 1H), 4.37~4.49 and 4.13 (m and q, 2H, J=7.2 Hz), 3.72 and 3.62 (s and s, 3H), 2.44~3.02 (m, 5H), 1.65~1.80 and 1.50~1.60 (m and m, 1H), 1.42 and 1.23 (t and t, 3H, J=7.2 and 7.2 Hz).

7) 9-Bromo-5-methoxycarbonylmethyl-6,7-dihydro-1H, 5H-pyrido[1,2,3-de]quinoxaline-2,3-dione To a mixture of 20% aqueous titanium trichloride (540 g, 0.7 mol), water (500 mL), and acetone (500 mL) was added dropwise 6-bromo-2-methoxycarbonylmethyl-8-nitro-N-ethoxalyltetrahydroquinoline (46 g, obtained above) in acetone (500 mL) over 1 h at 0° C. The mixture was stirred for 3 h at 0° C., diluted with water (1 L) and extracted with dichloromethane (1 L and 500 mL). The organic layers were washed successively with 1N hydrochloric acid, water, and brine, dried over magnesium sulfate, and concentrated. The residual solid was rinsed with a 1:1 mixture of hexane and toluene (400 mL) to give 17.4 g of the title compound (49% from 2-methoxycarbonylmethyltetrahydroquinoline hydrochloride): mp 185°~187° C.; $^1$H NMR (270 MHz, DMSO-d$_6$) δ12.04 (bs, 1H), 7.20 (d, 1H, J=2 Hz), 7.15 (d, 1H, J=2 Hz), 5.04~5.13 (m, 1H), 3.62 (s, 3H), 2.94 (ddd, 1H, J=17.1, 13.5, 4.5 Hz), 2.78 (dm, 1H, J=17.1 Hz), 2.63 (dd, 1H, J=18, 7.2 Hz), 2.57 (dd, 1H, J=18, 3.6 Hz), 2.09 (dm, 1H, J=13.5 Hz), 1.80~1.95 (m, 1H).

EXAMPLE 23

9-Bromo-5-carboxymethyl-6,7-dihydro-1H, 5H-pyrido[1,2,3-de]quinoxaline-2,3-dione Hydrolysis of 9-bromo-5-methoxycarbonylmethyl-6,7-dihydro-1H, 5H-pyrido[1,2,3-de]quinoxaline-2,3-dione (10.4 g, 0.03 mol) was carried out as described in Example 3 to give 9 g of the title compound (90%): mp>270° C.; $^1$H NMR (270 MHz, DMSO-d$_6$) δ12.06 (bs, 1H), 7.20 (d, 1H, J=2 Hz), 7.15 (m, 1H, J, =2 Hz), 5.02~5.12 (m, 1H), 2.95 (ddd, 1H, J=17.1, 13.5, 4.5 Hz), 2.79 (dm, 1H, J=17.1 Hz), 2.43~2.61 (m, 2H), 2.12 (dm, 1H, J=13.5 Hz), 1.78~1.96 (m, 1H).

EXAMPLE 24

9-bromo-5-carbamoyl-6,7-dihydro-1H, 5H-pyrido[1,2,3-de]quinoxaline-2,3-dione;

The title compound was obtained by a method similar to that described in Example 11 with 9-bromo-5-carboxy-6,7-dihydro-1H, 5H-pyrido[1,2,3-de]quinoxaline-2,3-dione: mp>250° C.; $^1$H NMR (270 MHz, DMSO-d$_6$) δ7.67 (bs, 1H), 7.30 (bs, 1H), 7.13 (bs, 2H), 5.02~5.10 (m, 1H), 2.80 (dm, 1H, J=16.8 Hz), 2.37~2.65 (m, 2H), 1.83~2.00 (m, 1H).

EXAMPLE 25

9-bromo-5-(N-hydroxycarbamoyl)-6,7-dihydro-1H, 5H-pyrido[1,2,3-de]quinoxaline-2,3-dione The title compound was obtained by a method similar to that described in Example 16 with 9-bromo-5-carboxy-6,7-dihydro-1H, 5H-pyrido[1,2,3-de]quinoxaline-2,3-dione: mp 143~146° C.; $^1$H NMR (270 MHz, DMSO-d$_6$) δ12.09 (s, 1H), 10.78 (s, 1H), 8.96 (s, 1H), 7.17 (bs, 2H), 5.04~5.10 (m, 1H), 2.80 (dm, 1H, J=16.8 Hz), 2.35~2.67 (m, 2H), 1.83~2.00 (m, 1H).

EXAMPLE 26

9-Bromo-5-phenylcarbamoylmethyl-6,7-dihydro-1H, 5H-pyrido[1,2,3-de]quinoxaline-2,3-dione The title compound was obtained by a method similar to that described in Example 5 with 9-bromo-5-carboxymethyl-6,7-dihydro-1H, 5H-pyrido[1,2,3-de]quinoxaline-2,3-dione: mp>270° C.; $^1$H NMR (270 MHz, DMSO-d$_6$) δ12.07 (bs, 1H), 10.01 (s, 1H), 7.56 (d, 2H, J=7.4 Hz), 7.30 (t, 2H, J=7.9 Hz), 7.24 (d, 1H, J=2 Hz), 7.17 (d, 1H, J=2 Hz), 7.05 (t, 1H, J=7.5 Hz), 5.16~5.26 (m, 1H), 3.07 (ddd, 1H, J=17.1, 13.5, 4.5 Hz), 2.83 (dm, 1H, J=17.1 Hz), 2.63 (dd, 1H, J=13.5, 3.6 Hz), 2.57 (dd, 1H, J=13.5, 4.5 Hz), 2.12 (dm, 1H, J=13.5 Hz), 1.78~1.96 (m, 1H).

EXAMPLE 27

9-Bromo-5-phthalimidomethyl-6,7-dihydro-1H, 5H-pyrido[1,2,3-de]-quinoxaline-2,3-dione 1) 2-Phthalimidomethyltetrahydroquinoline To a solution of 2-hydroxymethyltetrahydroquinoline (10 g, 61 mmol), imidazole (10.0 g, 147 mmol), and triphenylphosphine (19.0 g, 72.4 mmol) in a mixed solvent of 5:1 toluene/acetonitrile (360 mL) was added iodine (16.85 g, 66.4 mmol) at 0° C. The mixture was stirred for 2 h at 0° C. and aqueous sodium thiosulfate was added. The organic layer was separated, washed with water and brine, dried over magnesium sulfate, and concentrated. The residue was triturated with diethyl ether and insoluble materials were removed by filtration. The filtrate was concentrated and the residue was dissolved in DMF (60 mL) and potassium phthalimide (13.6 g, 73.48 mmol) was added. The mixture was heated at 60° C. for 2 h and diluted with water (200 mL). The mixture was extracted with 1:1 toluene/ethyl acetate (200 mL×2). The organic layers were washed with brine, dried over magnesium sulfate, and concentrated. The residue was purified with silica gel column chromatography with 10:1 to 6:1 hexane/ethyl acetate to give 10.25 g of 2-Phthalimidomethyltetrahydroquinoline (75%): $^1$H NMR (270 MHz, CDCl$_3$) δ7.86 (m, 2H), 7.74 (m, 2H), 6.95 (m, 2H), 6.59 (t, 1H, J=8 Hz), 6.49 (d, 1H, J=8 Hz), 3.91 (dd, 1H, J=14, 5 Hz), 3.78 (dd, 1H, J=14, 5 Hz), 3.68 (m, 1H), 2.78 (m, 2H), 2.00 (m, 1H), 1.69 (m, 1H).

2) 9-Bromo-5-phthalimidomethyl-6,7-dihydro-1H, 5H-pyrido[1,2,3-de]quinoxaline-2,3-dione The title compound was prepared by the route outlined in Example 22-4 to 7 starting with 2-phthalimidomethyltetrahydroquinoline: mp>300° C.; $^1$H NMR (270 MHz, DMSO-$d_6$) δ12.02 (bs, 1H), 7.84 (bs, 4H), 7.26 (s, 1H), 7.18 (s, 1H), 5.21~5.32 (m, 1H), 3.86 (dd, 1H, J=14, 9 Hz), 3.75 (dd, 1H, J=14, 5 Hz), 3.10 (ddd, 1H, J=17.1, 13.5, 4.5 Hz), 2.86 (dm, 1H, J=17.1 Hz), 2.25 (dm, 1H, J=13.5 Hz), 1.77~1.95 (m, 1H).

EXAMPLE 28

9-Bromo-5-aminomethyl-6,7-dihydro-1H, 5H-pyrido[1,2,3-de]quinoxaline-2,3-dione hydrochloride Hydrolysis of 9-bromo-5-phthalimidomethyl-6,7-dihydro-1H, 5H-pyrido [1,2,3-de]-quinoxaline-2,3-dione (1.64 g, 3.8 mmol) was carried out as described in Example 8 to give 1.27 g of the title compound (96%): mp 246~255° C. (dec); $^1$H NMR (270 MHz, DMSO-$d_6$) δ12.10 (bs, 1H), 8.12 (bs, 3H), 7.23 (s, 2H), 5.05~5.17 (m, 1H), 2.85~3.10 (m, 3H), 2.78 (dm, 1H, J=17.1 Hz), 2.25 (dm, 1H, J=13.5 Hz), 1.77~1.95 (m, 1H).

EXAMPLE 29

9-Bromo-5-benzoylaminomethyl-6,7-dihydro-1H, 5H-pyrido[1,2,3-de]quinoxaline-2,3-dione A procedure similar to that described in Example 15 was carried out with 9-bromo-5-aminomethyl-6,7-dihydro-1H, 5H-pyrido[1,2,3-de]quinoxaline-2,3-dione hydrochloride (800 mg, 2.31 mmol) and benzoic acid (312 mg, 2.56 mmol) to give 564 mg of the title compound (59%): mp 169~175° C. (dec); $^1$H NMR (270 MHz, DMSO-$d_6$) δ12.03 (s, 1H), 8.66 (t, 1H, J=5.4 Hz), 7.77 (d, 2H, J=8.6 Hz), 7.41~7.56 (m, 3H), 7.24 (s, 1H), 7.19 (s, 1H), 5.03~5.13 (m, 1H), 3.62 (dt, 1H, J=11, 6.5 Hz), 3.28~3.40 (m, 1H), 3.10 (ddd, 1H, J=17.1, 13.5, 4.5 Hz), 2.78 (dm, 1H, J=17.1 Hz), 2.14 (dm, 1H, J=13.5 Hz), 1.73~1.89 (m, 1H).

EXAMPLE 30

9-Bromo-5-(N'-phenylureidomethyl)-6,7-dihydro-1H, 5H-pyrido[1,2,3-de]quinoxaline-2,3-dione A procedure similar to that described in Example 14 was carried out with 9-bromo-5-aminomethyl-6,7-dihydro-1H, 5H-pyrido[1,2,3-de]quinoxaline-2,3-dione hydrochloride (25 mg, 0.08 mmol) and phenyl isocyanate (13.4 μL, 0.096 mmol) to give 10 mg of the title compound after silica gel column chromatography with 20:1 ethyl acetate/acetic acid (29%): mp>270° C.; $^1$H NMR (270 MHz, DMSO-$d_6$) δ12.03 (s, 1H), 8.89 (bs, 1H), 7.39 (d, 1H, J=8.6 Hz), 7.21 (t, 1H, J=8.6 Hz), 7.19 (s, 1H), 7.14 (s, 1H), 6.89 (t, 1H, J=8.6 Hz), 6.89 (bs, 1H), 4.84~4.94 (m, 1H), 3.10~3.30 (m, 2H), 3.06 (ddd, 1H, J=17.1, 13.5, 4.5 Hz), 2.76 (dm, 1H, J=17.1 Hz), 2.18 (dm, 1H, J=13.5 Hz), 1.72~1.88 (m, 1H).

EXAMPLE 31

9-Bromo-5-ethoxycarbonylethyl-6,7-dihydro-1H, 5H-pyrido[1,2,3-de]quinoxaline-2,3-dione 1) N-Ethoxalyl-2-trimethylsilyloxymethyltetrahydroquinoline To a solution of 2-hydroxymethyltetrahydroquinoline (7.86 g, 48.16 mmol) in dichloromethane (80 mL) containing triethylamine (10 mL, 72.23 mmol) was added trimethylsilyl chloride (6.7 mL, 52.97 mmol) at 0° C. The mixture was stirred for 10 min at 0° C. followed by addition of triethylamine (10 mL) and ethyl chlorooxalate (5.9 mL, 52.97 mmol). The mixture was stirred for 30 min at 0° C. and water was added. The organic layer was separated, washed with water, dried over magnesium sulfate, and concentrated to give 15.6 g of N-ethoxalyl-2-trimethylsilyloxymethyltetrahydroquinoline (106%): $^1$H NMR (270 MHz, CDCl$_3$) δ6.97~7.16 (m, 4H), 4.68 (m, 1H), 4.09 (q, 2H, J=7 Hz), 3.72 (m, 1H), 3.54 (m, 1H), 2.65 (m, 2H), 2.37 (m, 1H), 1.69 (m, 1H), 1.06 (t, 3H, J=7 Hz), 0.03 (s, 9H).

2) N-Ethoxalyl-2-formyltetrahydroquinoline

A mixture of N-ethoxalyl-2-trimethylsilyloxymethyltetrahydroquinoline (15.55 g, 50.92 mmol) and Dess-Martin reagent (32.4 g, 76.37 mmol) in dichloromethane (160 mL) in the presence of trifluoroacetic acid (0.8 mL) was stirred for 1 h at room temperature. Aqueous sodium thiosulfate solution and saturated aqueous sodium bicarbonate were added successively and the mixture was extracted with ethyl acetate. The organic layer was washed with brine, dried over magnesium sulfate, and concentrated to give 11.23 g of N-ethoxalyl-2-formyltetrahydroquinoline (84%): $^1$H NMR (270 MHz, CDCl$_3$) δ9.57 (s, 1H), 7.19 (m, 4H), 5.07 (t, 1H, J=8 Hz), 4.19 (q, 2H, J=7 Hz), 2.76 (m, 2H), 2.45 (m, 1H), 1.96 (m, 1H), 1.15 (t, 3H, J=7 Hz).

3) N-Ethoxalyl-2-ethoxycarbonylethenyltetrahydroquinoline

To a solution of diethylphosphonoacetic acid diethyl ester (10.6 g, 47.1 mmol) in THF (100 mL) was added potassium tert-butoxide (5.04 g, 44.9 mmol) at 0° C. The mixture was stirred for 20 min at room temperature. To the solution was added dropwise N-ethoxalyl-2-formyltetrahydroquinoline (11.18 g, 42.8 mmol) in THF (120 mL) at 0° C. After the complete addition, the mixture was stirred for 15 min at room temperature and water and a small amount of diluted hydrochloric acid were added. The mixture was extracted with ethyl acetate. The organic layer was washed three times with brine, dried over magnesium sulfate, and concentrated. The residue was purified by silica gel column chromatography with 4:1 to 3:1 hexane/ethyl acetate to give 7.63 g of N-ethoxalyl-2-ethoxycarbonylethenyltetrahydroquinoline (54%): $^1$H NMR (270 MHz, CDCl$_3$) δ7.15 (m, 4H), 6.79 (dd, 1H, J=16, 5 Hz), 5.89 (dd, 1H, J=16, 2 Hz), 5.31 (m, 1H), 4.12 (q, 2H, J=7 Hz), 2.73 (t, 2H, J=6 Hz), 2.47 (m, 1H), 1.69 (m, 1H), 1.25 (t, 3H, J=7 Hz), 1.11 (t, 3H, J=7 Hz).

4) N-Ethoxalyl-2-ethoxycarbonylethyltetrahydroquinoline

N-Ethoxalyl-2-ethoxycarbonylethenyltetrahydroquinoline (4 g, 12.1 mmol) in ethanol (100 mL) was hydrogenated over 10% palladium on carbon (500 mL) under atmospheric pressure of hydrogen for 1.5 h at room temperature. The mixture was filtered through celite and the filtrate was concentrated to give 3.83 g of N-ethoxalyl-2-ethoxycarbonylethyltetrahydroquinoline (95%): $^1$H NMR (270 MHz, CDCl$_3$) δ7.03~7.19 (m, 4H), 4.78 (m, 1H), 4.11(q, 4H, J 7 Hz), 2.73 (t, 2H, J=6 Hz), 2.47 (m, 1H), 1.69 (m, 1H), 1.25 (t, 3H, J=7 Hz), 1.11 (t, 3H, J=7Hz).

5) 9-Bromo-5-ethoxycarbonylethyl-6,7-dihydro-1H, 5H-pyrido[1,2,3-de]quinoxaline-2,3-dione The title compound was prepared by the route outlined in Example 1-2 to 1-4 starting with N-ethoxalyl-2-ethoxycarbonylethyltetrahydroquinolie instead of N-ethoxalylindoline: mp 185° C.; $^1$H NMR (270 MHz, CD$_3$OD) δ7.23 (s, 1H), 7.19 (s, 1H), 5.00~5.09 (m, 1H), 4.09 (q, 2H, J=7.5 Hz), 3.04 (ddd, 1H, J=17.1, 13.5, 4.5 Hz), 2.88 (dm, 1H, J=17.1 Hz), 2.45 (t, 2H, J=7.5 Hz), 2.18 (dm, 1H, J =13.5 Hz), 1.80~2.08 (m, 3H).

EXAMPLE 32

9-Bromo-5-carboxyethyl-6,7-dihydro-1H, 5H-pyrido[1,2,3-de]quinoxaline-2,3-dione The title compound was obtained by hydrolysis of 9-bromo-5-ethoxycarbonylethyl-6,7-dihydro-1H, 5H-pyrido[1,2,3-de]quinoxaline-2,3-dione as described in Example 3: mp 275°~276° C.; $^1$H NMR (270 MHz, DMSO-$d_6$) δ12.03 (bs, 1H), 7.19 (s, 1H), 7.14 (s, 1H), 4.80~4.92 (m, 1H), 2.93 (ddd, 1H, J=17.1, 13.5, 4.5 Hz), 2.77 (dm, 1H, J=17.1 Hz), 2.20~2.44 (m, 2H), 2.10 (dm, 1H, J=13.5 Hz), 1.62~1.88 (m, 3H).

EXAMPLE 33

9-Bromo-5-cyclohexylcarbamoyl-6,7-dihydro-1H, 5H-pyrido[1,2,3-de]quinoxaline- 2,3-dione A procedure similar to that described in Example 5 was carried out with 9-bromo-5-carboxy-6,7-dihydro-1H, 5H-pyrido[1,2,3-de]quinoxaline-2,3-dione (300 mg, 0.92 mmol) and cyclohexylamine (100 mg, 1.0 mmol) to give 340 mg of the title compound (91%): mp>270° C.; $^1$H NMR (270 MHz, DMSO-$d_6$) δ12.14 (s, 1H), 8.03 (d, 1H, J=7.9 Hz), 7.16 (bs, 1H), 7.14 (bs, 1H), 5.08~5.13 (m, 1H), 3.42~3.59 (m, 1H), 2.79 (dm, 1H, J=16.8 Hz), 2.45~2.63 (m, 1H), 2.36 (dm, 1H, J=13.5 Hz), 1.85~2.02 (m, 1H), 1.63~1.74 (m, 4H), 1.05~1.33 (m, 6H).

EXAMPLE 34

9-Bromo-5-hydroxymethyl-6,7-dihydro-1H, 5H-pyrido[1,2,3-de]quinoxaline-2,3-dione To a solution of 9-bromo-5-carboxy-6,7-dihydro-1H, 5H-pyrido[1,2,3-de]quinoxaline-2,3-dione (9.8 g, 30.14 mmol) in DMF (65 mL) in the presence of triethylamine (4.8 mL, 34.5 mmol) was added isobutyl chloroformate (2.11 mL, 35.49 mmol) at −15° C. The mixture was stirred for 4 h at the same temperature and N-hydroxysuccinimide (13.46 g, 116.95 mmol) and dimethylaminopyridine (900 mg) was added. The stirring was continued for 4 h at 0° C. and acetic acid (6 mL) was added. The mixture was poured into water (1.2 L) and the precipitates formed were collected by filtration. The precipitate was washed with water and dried in vacuo to give 10.65 g of the activated ester (84%). The activated ester (10 g, 23.69 mmol) was suspended in THF (200 mL) and sodium borohydride (total 1.8 g, 47.45 mmol) was occasionally added during the period of 3 h to the stirred mixture at −15° C. The mixture was allowed to warm at 0° C. and after being stirred for 30 min, poured into water (500 mL). The mixture was acidified with 3N hydrochloric acid and extracted with ethyl acetate (500 mL×3). The organic layers were washed with brine, dried over magnesium sulfate, and concentrated to give 7.96 g of the title compound (quant). The pure compound was obtained by silica gel column chromatography with 1 to 3% acetic acid/ethyl acetate as eluents (64%): mp 202~206° C. (dec); $^1$H NMR (270 MHz, DMSO-$d_6$) δ12.03 (bs, 1H), 7.19 (s, 1H), 7.16 (s, 1H), 4.98 (t, 1H, J=6.5 Hz), 4.68~4.77 (m, 1H), 3.40~3.55 (m, 2H), 2.98 (ddd, 1H, J=17.1, 13.5, 4.5 Hz), 2.76 (dm, 1H, J=17.1 Hz), 2,32 (dm, 1H, J=13.5 Hz), 1.66~1.83 (m, 1H).

EXAMPLE 35

9-Bromo-5-methylsulfonyloxymethyl-6,7-dihydro-1H, 5H-pyrido[1,2,3-de]quinoxaline-2,3-dione To a solution of 9-bromo-5-hydroxymethyl-6,7-dihydro-1H, 5H-pyrido[1,2,3-de]quinoxaline-2,3-dione (3 g, 9.65 mmol) and triethylamine (1,28 g, 12.67 mmol) in THF (200 mL) was added methanesulfonyl chloride (1.44 g, 12.57 mmol) at −20° C. The mixture was stirred for 1.5 h at the same temperature and triethylamine (0.6 mL) and methanesulfonylchloride (0.4 mL) were added. The mixture was further stirred for 1 h at −20° C. and for 30 min at 0° C. and poured into water (500 mL). The mixture was acidified with 3N hydrochloric acid and extracted with ethyl acetate (500 mL×3). The organic layers were washed with brine, dried over magnesium sulfate, and concentrated. The residue was purified by silica gel column chromatography with 1 to 5% acetic acid/ethyl acetate to give 2.42 g of the title compound (64%): mp 125°~130° C. (dec); $^1$H NMR (270 MHz, DMSO-$d_6$) δ12.05 (bs, 1H), 7.20 (s, 1H), 7.15 (s, 1H), 4.97~5.06 (m, 1H), 4.28 (d, 2H, J=7.5 Hz), 3.20 (s, 3H), 2.97 (ddd, 1H, J=17.1, 13.5, 4.5 Hz), 2.83 (dm, 1H, J=17.1 Hz), 2.27 (dm, 1H, J=13.5 Hz), 1.81~1.97 (m, 1H).

EXAMPLE 36

9-Bromo-5-iodomethyl-6,7-dihydro-1H, 5H-pyrido[1,2,3-de]quinoxaline-2,3-dione A mixture of 9-bromo-5-methylsulfonyloxymethyl-6,7-dihydro-1H, 5H-pyrido[1,2,3-de]quinoxaline-2,3-dione (2.3 g, 5.91 mmol) and sodium iodide (7.9 g, 52.7 mmol) in DMF (30 mL) was heated at 60° C. for 22 h and poured into water (400 mL). The precipitates formed was collected by filtration, washed with water, and dried in vacuo to give 1.95 g of the title compound (78%): mp 260°~270.5° C.; $^1$H NMR (270 MHz, CD$_3$OD) δ7.22 (s, 1H), 7.19 (s, 1H), 4.95~5.07 (m, 1H), 3.50 (dd, 1H, J=10.2, 4 Hz), 3.24 (d, 1H, J=10.2 Hz), 2.97 (ddd, 1H, J=17.1, 13.5, 4.5 Hz), 2.84 (dm, 1H, J=17.1 Hz), 2.70 (dm, 1H, J=13.5 Hz), 1.90~2.07 (m, 1H).

EXAMPLE 37

9-Bromo-5-(O-2-tetrahydropyranyl-N-hydroxycarbamoylmethyl)-6,7-dihydro-1H, 5H-pyrido[1,2,3-de]quinoxaline-2,3-dione A procedure similar to that described in Example 5 was carried out with 9-bromo-5-carboxymethyl-6,7-dihydro-1H, 5H-pyrido[1,2,3-de]quinoxaline-2,3-dione (300 mg, 0.92 mmol) and O-tetrahydropyranyl-hydroxylamine (120 mg, 1.03 mmol) to give 110 mg of the title compound: mp 149°~151° C.; $^1$H NMR (270 MHz, CD$_3$OD) δ7.22 (s, 1H), 7.19 (s, 1H), 5.25~5.39 (m, 1H), 4.92 (bs, 1H), 3.91~4.03 (m, 1H), 3.54~3.64 (m, 1H), 3.02~3.18 (m, 1H), 2.86 (dm, 1H, J=17.1 Hz), 2.52~2.61 (m, 1H), 2.25 (dm, 1H, J=13.5 Hz), 1.92~2.07 (m, 1H), 1.50~1.85 (m, 6H).

EXAMPLE 38

9-Bromo-5-[(1 S)-1-methoxycarbonyl-2-phenylethylcarbamoyl]-6,7-dihydro-1H, 5H-pyrido[1,2,3-de]quinoxaline-2,3-dione A procedure similar to that described in Example 5 was carried out with 9-bromo-5-carboxy-6,7-dihydro-1H, 5H-pyrido[1,2,3-de]quinoxaline-2,3-dione (300 mg, 0.92 mmol) and (L)-phenylalanine methyl ester hydrochloride (215 mg, 1.0 mmol) to give 390 mg of a diastereomeric mixture of the title compound (87%): mp 170°~174° C. The mixture (300 mg) was separated by preparative thin layer silica gel chromatography with 1% acetic acid/ethyl acetate to give 110 mg of the less polar product and 120 mg of the more polar product. Less polar product: $^1$H NMR (270 MHz, DMSO-d$_6$) δ12.12 (s, 1H), 8.59 (d, 1H, J=7.6 Hz), 7.06~7.26 (m, 7H), 5.14~5.22 (m, 1H), 4.40~4.51 (m, 1H), 3.58 (s, 3H), 3.03 (dd, 1H, J=13.5, 4.5 Hz), 2.89 (dd, 1H, J=13.5, 9 Hz), 2.64 (dm, 1H, J=16.8 Hz), 2.37 (dm, 1H, J=12.6 Hz), 2.14~2.28 (m, 1H), 1.78~1.93 (m, 1H). More polar product: $^1$H NMR (270 MHz, DMSO-d$_6$) δ12.14 (s, 1H), 8.77 (d, 1H, J=7.6 Hz), 7.19~ 7.34 (m, 5H), 7.15 (d, 1H, J=2 Hz), 7.06 (d, 1H, J=2Hz), 5.13~5.18 (m, 1H), 4.47~4.58 (m, 1H), 3.63 (s, 3H), 3.10 (dd, 1H, J=13.5, 5.4 Hz), 2.85 (dd, 1H, J =13.5, 9.9 Hz), 2.44~2.56 (m, 1H), 2.10 (dm, 1H, J=12.6 Hz), 1.75~2.02 (m, 2H).

EXAMPLE 39

9-Bromo-5-[(1 R)-1-methoxycarbonyl-2-phenylethylcarbamoyl]-6,7-dihydro-1H, 5H-pyrido[1,2,3-de]quinoxaline-2,3-dione The same procedure as described in Example 38 was carried out with (D)-phenylalanine methyl ester hydrochloride to give the less polar product and the more polar product.

EXAMPLE 40

9-Bromo-5-ethoxalylaminomethyl-6,7-dihydro-1H, 5H-pyrido[1,2,3-de]quinoxaline-2,3-dione To a solution of 9-bromo-5-aminomethyl-6,7-dihydro-1H, 5H-pyrido[1,2,3-de]quinoxaline-2,3-dione hydrochloride (300 mg, 0.866 mmol)in a 1:1 mixture of dichloromethane and DMF (10 mL)in the presence of triethylamine (0.3 mL, 2.16 mmol) was added ethyl chlorooxalate (0.102 mL, 0.909 mmol) at 0° C. The mixture was stirred for 15 min at 0° C. and for 10 h at room temperature and then water was added. The mixture was extracted with ethyl acetate. The aqueous layer was acidified with 1N hydrochloric acid to pH 1 and extracted with ethyl acetate. The combined organic layers were washed with brine, dried over magnesium sulfate, and concentrated. The residual solid was recrystallized from ethanol-ether to give 75 mg of the title compound (21%): mp 214.5~220.5° C.; $^1$H NMR (270 MHz, DMSO-d$_6$) δ12.01 (s, 1H), 9.11 and 9.04 (two triplet, 1H, J=6 Hz), 7.19 (s, 1H), 7.14 (s, 1H), 4.98~5.07 (m, 1H), 4.21 (q, 2H, J=7.5 Hz), 3.17~3.57 (m, 2H), 3.01 (ddd, 1H, J=17.1, 13.5, 4.5 Hz), 2.79, (dm, 1H, J=17.1 Hz), 2.10 (dm, 1H, 13.5 Hz), 1.70~1.85 (m, 1H), 1.26 (t, 3H, J=7.5 Hz).

EXAMPLE 41

9-Bromo-5-oxaloaminomethyl-6,7-dihydro-1H, 5H-pyrido[1,2,3-de]quinoxaline- 2,3-dione Hydrolysis of 9-bromo-5-ethoxalylaminomethyl-6,7-dihydro-1H, 5H-pyrido[1,2,3-de]quinoxaline-2,3-dione (40 mg, 0.0098 mmol) was carried out as described in Example 3 to give 21 mg of the title compound (56%): mp 198°~217° C.; $^1$H NMR (270 MHz, DMSO-d$_6$) δ12.02 (s, 1H), 9.04 (t, 1H, J=6 Hz), 7.19 (s, 1H), 7.14 (s, 1H), 4.98~5.07 (m, 1H), 3.17~3.57 (m, 2H), 3.00 (ddd, 1H, J=17.1, 13.5, 4.5 Hz), 2.74 (dm, 1H, J=17.1 Hz), 2.10 (dm, 1H, 13.5 Hz), 1.70~1.84 (m, 1H).

EXAMPLE 42

9-Bromo-5-cyclopropylcarbamoyl-6,7-dihydro-1H, 5H-pyrido[1,2,3-de]quinoxaline-2,3-dione A procedure similar to that described in Example 5 was carried out with 9-bromo-5-carboxy-6,7-dihydro-1H, 5H-pyrido[1,2,3-de]quinoxaline-2,3-dione (300 mg, 0.92 mmol) and cyclopropylamine (100 μL, 1.0 mmol) to give 310 mg of the title compound (93%): mp 222°~225° C.; $^1$H NMR (270 MHz, DMSO-d$_6$) δ12.13 (s, 1H), 8.22 (d, 1H, J=4.0 Hz), 7.18 (bs, 1H), 7.16 (bs, 1H), 5.02~5.06 (m, 1H), 2.79 (dm, 1H, J=16.8 Hz), 2.45~2.62 (m, 2H), 2.36 (dm, 1H, J=13.5 Hz), 1.81~1.97 (m, 1H), 0.62 (dm, 2H, J=7.2 Hz), 1.33~1.41 (m, 2H).

EXAMPLE 43

9-bromo-5-(m-ethoxycarbonylphenylcarbamoyl)-6, 7-dihydro-1H, 5H-pyrido[1,2,3-de]quinoxaline-2,3-dione A procedure similar to that described in Example 5 was carried out with 9-bromo-5-carboxy-6,7-dihydro-1H, 5H-pyrido[1,2,3-de]quinoxaline-2,3-dione (300 mg, 0.92 mmol) and m-ethoxycarbonylaniline (200 mg, 1.2 mmol) to give 410 mg of the title compound (94%): mp 262°~265° C.; $^1$H NMR (270 MHz, DMSO-d$_6$) δ12.2 (br, 1H), 10.60 (s, 1H), 8.23 (bs, 1H), 7.81 (d, 1H, J=8.0 Hz), 7.67 (d, 1H, J=8.0 Hz), 7.47 (t, 2H, J=8.0 Hz), 7.22 (bs, 1H), 7.19 (bs, 1H), 5.29~5.34 (m, 1H), 4.30 (q, 2H, J=7.1 Hz), 2.85 (dm, 1H, J=16.8 Hz), 2.50~2.82 (m, 2H), 2.03~2.20 (m, 1H), 1.30 (t, 3H, J=7.1 Hz).

EXAMPLE 44

9-Bromo-5-(m-carboxyphenylcarbamoyl)-6,7-dihydro-1H, 5H-pyrido[1,2,3-de]quinoxaline-2,3-dione Hydrolysis of 9-bromo-5-(m-ethoxycarbonylphenylcarbamoyl)-6,7-dihydro-1H, 5H-pyrido[1,2,3-de]quinoxaline-2,3-dione (280 mg, 0.59 mmol) was carried out as described in Example 3 to give 210 mg of the title compound (80%): mp 245°~247° C.; $^1$H NMR (270 MHz, DMSO-d$_6$) δ12.23 (s, 1H), 10.51 (s, 1H), 8.19 (bs, 1H), 7.78 (d, 1H, J=8.0 Hz), 7.65 (d, 1H, J=8.0 Hz), 7.45 (t, 2H, J=8.0 Hz), 7.22 (bs, 2H), 7.19 (bs, 1H), 5.29~5.34 (m, 1H), 2.85 (dm, 1H, J=16.8 Hz), 2.35~2.73 (m, 2H), 2.03~2.20 (m, 1H).

EXAMPLE 45

9-Bromo-5-[(1 S)-1-carboxy-2-phenylethylcarbamoyl]-6,7-dihydro-1H, 5H-pyrido[1,2,3-de]quinoxaline-2,3-dione Hydrolysis of each of diasteromers of 9-bromo-5-[(1S)-1-methoxycarbonyl-2-phenylethylcarbamoyl]-6,7-dihydro-1H, 5H-pyrido[1,2,3-de]quinoxaline-2,3-dione was carried out as described in Example 3 to give each of the diasteromerically pure title compounds, respectively. The carboxylic acid from less polar methyl ester: $^1$H NMR (270 MHz, DMSO-d$_6$) δ12.74 (br, 1H), 12.12 (s, 1H), 8.46 (d, 1H, J=7.9 Hz), 7.06~7.26 (m, 7 H), 5.13~5.20 (m, 1H), 4.34~4.45 (m, 1H), 3.03 (dd, 1H, J=13.5, 4.5 Hz), 2.84 (dd, 1H, J=13.5, 9 Hz), 2.61 (dm, 1H, J=16.8 Hz), 2,38 (dm, 1H, J=12.6 Hz), 2.12~2.27 (m, 1H), 1.76~1.91 (m, 1H). The carboxylic acid from polar methyl ester: $^1$H NMR (270 MHz, DMSO-d$_6$) δ12.13 (s, 1H), 8.66 (d, 1H, J=7.6 Hz), 7.18~7.32 (m, 5H), 7.14 (d, 1H, J=2 Hz), 7.03 (d, 1H, J=2 Hz), 5.12~5.17 (m, 1H), 4.42~4.53 (m, 1H), 3.10 (dd, 1H, J=13.5, 5.4 Hz), 2.82 (dd, 1H, J=13.5, 9.9 Hz), 2.43~2.56 (m, 1H), 2.09 (dm, 1H, J=12.6 Hz), 1.75~2.02 (m, 2H).

EXAMPLE 46

9-Bromo-5-[(1R)-1-carboxy-2-phenylethylcarbamoyl]-6,7-dihydro-1H, 5H-pyrido[1,2,3-de]quinoxaline-2,3-dione The same hydrolysis as described in Example 45 was carried out with each of diastereomers of 9-bromo-5-[(1R)-1-methoxycarbonyl-2-phenylethylcarbamoyl]-6,7-dihydro-1H, 5H-pyrido[1,2,3-de]quinoxaline-2,3-dione to give each of the diastereomerically pure title compounds.

EXAMPLE 47

9-Bromo-5-benzylcarbamoylmethyl-6,7-dihydro-1H, 5H-pyrido[1,2,3-de]quinoxaline-2,3-dione A procedure similar to that described in Example 5 was carried out with 9-bromo-5-carboxymethyl-6,7-dihydro-1H, 5H-pyrido[1,2,3-de]quinoxaline-2,3-dione (150 mg, 0.44 mmol) and benzylamine (54 µL, 0.5 mmol) to give 170 mg of the title compound (89%): mp 220°~223° C.; $^1$H NMR (270 MHz, DMSO-$d_6$) δ12.04 (bs, 1H), 8.46~8.55 (m, 1H), 7.19~7.37 (m, 6H), 7.14 (d, 1H, J=2 Hz), 5.09~5.19 (m, 1H), 4.21~4.35 (m, 2H), 3.04 (ddd, 1H, J=17.1, 13.5, 4.5 Hz), 2.77 (dm, 1H, J=17.1 Hz), 2.41~2.54 (m, 2H), 2.00 (dm, 1H, J=13.5 Hz), 1.72~1.90 (m, 1H).

EXAMPLE 48

9-Bromo-5-benzylmethylcarbamoylmethyl-6,7-dihydro-1H, 5H-pyrido[1,2,3-de]quinoxaline-2,3-dione A procedure similar to that described in Example 5 was carried out with 9-bromo-5-carboxymethyl-6,7-dihydro-1H, 5H-pyrido[1,2,3-de]quinoxaline-2,3-dione (150 mg, 0.44 mmol) and benzylmethylamine (65 µL, 0.5 mmol) to give 170 mg of the title compound (87%): mp 120°~125° C.; $^1$H NMR (270 MHz, DMSO-$d_6$) δ12.09 and 12.04 (two s, 1H), 7.10~7.41 (m, 7H), 5.09~5.21 (m, 1H), total 2H of 4.63 (s), 4.58 (d, J=16.2 Hz), and 4.47 (d, J=16.2 Hz), 2.95~3.12 (m, 1H), J=2.92 and 2.82 (two s, 3H), 2.78 (dm, 1H, J=17.1 Hz), 2.61~2.73 (m, 2H), 2.22 (dm, 1H, J=13.5 Hz), 1.79~1.94 (m, 1H).

EXAMPLE 49

9-Bromo-5-cyclopropylcarbamoylmethyl-6,7-dihydro-1H, 5H-pyrido[1,2,3-de]quinoxaline-2,3-dione A procedure similar to that described in Example 5 was carried out with 9-bromo-5-carboxymethyl-6,7-dihydro-1H, 5H-pyrido[1,2,3-de]quinoxaline-2,3-dione (150 mg, 0.44 mmol) and cyclopropylamine (50 µL, 0.5 mmol) to give 143 mg of the title compound (86%): mp 265°~268° C.; $^1$H NMR (270 MHz, DMSO-$d_6$) δ12.04 bs, 1H), 8.04 (d, 1H, J=4 Hz), 7.20 (d, 1H, J=2 Hz), 7.14 (d, 1H, J=2 Hz), 5.05~5.14 (m, 1H), 2.97 (ddd, 1H, J=17.1, 13.5, 4.5 Hz), 2.77 (dm, 1H, J=17.1 Hz), 2.54~2.64 (m, 2H), 2.35 (dd, 1H, J=16.2, 4.5 Hz), 2.25 (dd, 1H, J=16.2, 11.7 Hz), 2.00 (dm, 1H, J=13.5 Hz), 1.73~1.87 (m, 1H), 0.56~0.64 (m, 2H), 0.32~0.41 (m, 2H).

EXAMPLE 50

9-Bromo-5-(m-ethoxycarbonylphenylcarbamoylmethyl)-6,7-dihydro-1H, 5H-pyrido[1,2,3-de]quinoxaline-2,3-dione A procedure similar to that described in Example 5 was carried out with 9-bromo-5-carboxymethyl-6,7-dihydro-1H, 5H-pyrido[1,2,3-de]quinoxaline-2,3-dione (400 mg, 1.18 mmol) and m-ethoxycarbonylaniline (250 µL, 1.5 mmol) to give 510 mg of the title compound (89%): mp>270° C.; $^1$H NMR (270 MHz, DMSO-$d_6$) δ12.07 (bs, 1H), 10.25 (s, 1H), 8.20 (bs, 1H), 7.85 (d, 1H, J=8.1 Hz), 7.65 (d, 1H, J=8.1 Hz), 7.30 (t, 1H, J=8.1 Hz), 7.24 (d, 1H, J=2Hz), 7.17 (d, 1H, J=2 Hz), 5.16~5.27 (m, 1H), 4.32 (q, 2H, J=7.2 Hz), 3.05 (ddd, 1H, J=17.1, 13.5, 4.5 Hz), 2.83 (dm, 1H, J=17.1 Hz), 2.55~2.68 (m, 2H), 2.12 (dm, 1H, J=13.5 Hz), 1.81~1.97 (m, 1H), 1.33 (t, 3H, J=7.1 Hz).

EXAMPLE 51

9-Bromo-5-(p-ethoxycarbonylphenylcarbamoylmethyl)-6,7-dihydro-1H, 5H-pyrido[1,2,3-de]quinoxaline-2,3-dione To a solution of 9-bromo-5-carboxymethyl-6,7-dihydro-1H, 5H-pyrido[1,2,3-de]quinoxaline-2,3-dione (340 mg, 1 mmol) and triethylamine (140 µL, 1 mmol) in DMF (5 mL) was added isobutyl chloroformate (130 µL, 0.9 mmol) at −10° C. After being stirred for 15 min, p-ethoxycarbonylaniline (200 mg, 1.2 mmol) was added. The mixture was stirred overnight at room temperature and 0.2N hydrochloric acid was added. The precipitates formed were collected by filtration, washed with water, and dried in vacuo. The crude product was rinsed with methanol-water, and dried in vacuo to give 230 mg of the title compound (46%): mp>270° C.; $^1$H NMR (270 MHz, DMSO-$d_6$) δ12.07 (s, 1H), 10.35 (s, 1H), 7.92 (d, 2H, J=9 Hz), 7.70 (d, 1H, J=9 Hz), 7.24 (d, 1H, J=2 Hz), 7.17 (d, 2H, J=9 Hz), 5.16~5.28 (m, 1H), 4.28 (q, 2H, J=7.2 Hz), 3.04 (ddd, 1H, J=17.1, 13.5, 4.5 Hz), 2.83 (dm, 1H, J=16.8 Hz), 2.65 (d, 2H, J=7.6 Hz), 2.10 (dm, 1H, J=13.5 Hz), 1.80~1.97 (m, 1H), 1.31 (t, 3H, J=7.2 Hz).

EXAMPLE 52

9-Bromo-5-(o-ethoxycarbonylphenylcarbamoylmethyl)-6,7-dihydro-1H, 5H-pyrido[1,2,3-de]quinoxaline-2,3-dione To a solution of 9-bromo-5-carboxymethyl-6,7-dihydro-1H, 5H-pyrido[1,2,3-de]quinoxaline-2,3-dione (340 mg, 1 mmol), o-ethoxycarbonylaniline (150 µL, 1 mmol), and triethylamine (280 µL, 2 mmol) in dichloromethane (3 mL) was added N,N-bis(2-oxo-3-oxazolydinyl)phosphinic chloride (254 mg, 1 mmol) at 0° C. The mixture was stirred overnight at room temperature and 0.2N hydrochloric acid was added. The organic layer was separated and the aqueous layer was extracted with dichloromethane. The combined organic layers were washed with brine, dried over magnesium sulfate, and concentrated. The residual solid was rinsed with diethyl ether and dried in vacuo to give 290 mg of the title compound (58%): mp>265°~267° C.; $^1$H NMR (270 MHz, DMSO-$d_6$) δ12.05 (bs, 1H), 10.55 (s, 1H), 8.14 (d, 1H, J=8.1 Hz), 7.89 (d, 2H, J=8.1 Hz), 7.60 (t, 1H, J=8.1 Hz), 7.23 (d, 1H, J=2 Hz), 7.22 (t, 1H, J=8.1 Hz), 7.16 (d, 1H, J=2 Hz), 5.14~5.26 (m, 1H), 4.29 (q, 2H, J=7.2 Hz), 3.06 (ddd, 1H, J=17.1, 13.5, 4.5 Hz), 2.82 (dm, 1H, J=17.1 Hz), 2.62~2.76 (m, 2H), 2.18 (dm, 1H, J=13.5 Hz), 1.81~1.97 (m, 1H), 1.32 (t, 3H, J=7.2 Hz).

EXAMPLE 53

9-Bromo-5-(o-carboxyphenylcarbamoylmethyl)-6,7-dihydro-1H, 5H-pyrido-1,2,3-de]quinoxaline-2,3-dione Hydrolysis of 9-bromo-5-(o-ethoxycarbonylphenylcarbamoylmethyl)-6,7-dihydro-1H, 5H-pyrido[1,2,3-de]quinoxaline-2,3-dione (150 mg, 0.3 mmol) was carried out as described in Example 3 to give 110 mg of the title compound (80%): mp 197°~200° C.; $^1$H NMR (270 MHz, DMSO-d$_6$) δ12.05 (bs, 1H), 11.03 (s, 1H), 8.37 (d, 1H, J=8.1 Hz), 7.96 (d, 2H, J=8.1 Hz), 7.60 (t, 1H, J=8.1 Hz), 7.16~7.21 (m, 3H), 5.16~5.21 (m, 1H), 3.08 (ddd, 1H, J=17.1, 13.5, 4.5 Hz), 2.82 (dm, 1H, J=17.1 Hz), 2.62~2.77 (m, 2H), 2.18 (dm, 1H, J=13.5 Hz), 1.82~1.96 (m, 1H).

EXAMPLE 54

9-Bromo-5-(m-carboxyphenylcarbamoylmethyl)-6,7-dihydro-1H, 5H-pyrido[1,2,3-de]quinoxaline-2,3-dione Hydrolysis of 9-bromo-5-(m-ethoxycarbonylphenylcarbamoylmethyl)-6,7-dihydro-1H, 5H-pyrido[1,2,3-de]quinoxaline-2,3-dione (250 mg, 0.514 mmol) was carried out as described in Example 3 to give 210 mg of the title compound (89%): mp>270° C.; $^1$H NMR (270 MHz, DMSO-d$_6$) δ12.07 (s, 1H), 10.21 (s, 1H), 8.20 (bs, 1H), 7.81 (d, 1H, J=8.0 Hz), 7.63 (d, 1H, J=8.0 Hz), 7.43 (t, 2H, J=8.0 Hz), 7.24 (bs, 1H), 7.19 (bs, 1H), 5.17~5.28 (m, 1H), 3.06 (ddd, 1H, J=17.1, 13.5, 4.5 Hz), 2.83 (dm, 1H, J=16.8 Hz), 2.55~2.70 (m, 2H), 2.12 (dm, 1H, J=13.5 Hz), 1.80~1.97 (m, 1H).

EXAMPLE 55

9-Bromo-5-(p-carboxyphenylcarbamoylmethyl)-6,7-dihydro-1H, 5H-pyrido[1,2,3-de]quinoxaline-2,3-dione Hydrolysis of 9-bromo-5-(p-ethoxycarbonylphenylcarbamoylmethyl)-6,7-dihydro-1H, 5H-pyrido[1,2,3-de]quinoxaline-2,3-dione (130 mg, 0.26 mmol) was carried out as described in Example 3 to give 115 mg of the title compound (96%): mp>270° C.; $^1$H NMR (270 MHz, DMSO-d$_6$) δ12.71 (bs, 1H), 12.07 (s, 1H), 10.31 (s, 1H), 7.89 (d, 2H, J=9 Hz), 7.68 (d, 1H, J=9 Hz), 7.24 (d, 1H, J=2 Hz), 7.17 (d, 2H, J=9 Hz), 5.17~5.27 (m, 1H), 3.05 (ddd, 1H, J=17.1, 13.5, 4.5 Hz), 2.83 (dm, 1H, J=16.8 Hz), 2.64 (d, 2H, J=7.2 Hz), 2.53 (s, 3H), 2.11 (dm, 1H, J =13.5 Hz), 1.82~1.97 (m, 1H).

EXAMPLE 56

9-Bromo-5-carbamoylmethyl-6,7-dihydro-1H, 5H-pyrido[1,2,3-de]quinoxaline-2,3-dione A procedure similar to that described in Example 11 was carried out with 9-bromo-5-carboxymethyl-6,7-dihydro-1H, 5H-pyrido[1,2,3-de]quinoxaline-2,3-dione (170 mg, 0.5 mmol) to give 130 mg of the title compound (77%): mp>270° C.; $^1$H NMR (270 MHz, DMSO-d$_6$) δ11.95 (bs, 1H), 7.45 (bs, 1H), 7.21 (d, 1H, J =2 Hz), 7.15 (d, 1H, J=2 Hz), 6.99 (bs, 1H), 5.03~5.14 (m, 1H), 3.00 (ddd, 1H, J=17.1, 13.5, 4.5 Hz), 2.78 (dm, 1H, J=17.1 Hz), 2.26~2.44 (m, 2H), 2.07 (dm, 1H, J=13.5 Hz), 1.74~1.90 (m, 1H).

EXAMPLE 57

9-Bromo-5-methylphenylcarbamoylmethyl-6,7-dihydro-1H, 5H-pyrido[1,2,3-de]quinoxaline-2,3-dione A procedure similar to that described in Example 51 was carried out with 9-bromo-5-carboxymethyl-6,7-dihydro-1H, 5H-pyrido[1,2,3-de]quinoxaline-2,3-dione (170 mg, 0.5 mmol) and N-methylaniline (60 µL, 0.55 mmol) to give 120 mg of the title compound (56%): mp 136°~139° C.; $^1$H NMR (270 MHz, DMSO-d$_6$) δ11.97 (bs, 1H), 7.33~7.44 (m, 5H), 7.11 (s, 1H), 7.07 (s, 1H), 5.05~5.15 (m, 1H), 3.17 (s, 3H), 2.60~2.84 (m, 2H), 2.18~2.38 (m, 2H), 2.13 (dm, 1H, J=13.5 Hz), 1.71~1.89 (m, 1H).

EXAMPLE 58

9-Bromo-5-cyclohexylcarbamoylmethyl-6,7-dihydro-1H, 5H-pyrido[1,2,3-de]quinoxaline-2,3-dione A procedure similar to that described in Example 5 was carried out with 9-bromo-5-carboxymethyl-6,7-dihydro-1H, 5H-pyrido[1,2,3-de]quinoxaline-2,3-dione (150 mg, 0.442 mmol) and cyclohexylamine (50 mg, 0.51 mmol) to give 160 mg of the title compound (86%): mp>270° C.; $^1$H NMR (270 MHz, DMSO-d$_6$) δ12.04 bs, 1H), 7.86 (d, 1H, J=7.6 Hz), 7.21 (s, 1H), 7.15 (s, 1H), 5.03~5.18 (m, 1H), 3.43~3.60 (m, 1H), 3.03 (ddd, 1H, J=17.1, 13.5, 4.5 Hz), 2.76 (dm, 1H, J=17.1 Hz), 2.36 (dd, 1H, J=16.2, 4.5 Hz), 2.28 (dd, 1H, J=16.2, 11.7 Hz), 1.98 (dm, 1H, J=13.5 Hz), 1.50~1.86 (m, 5H), 1.03~1.36 (m, 6H).

EXAMPLE 59

9-Bromo-5-(o-sulfamoylphenylcarbamoylmethyl)-6,7-dihydro- 1H, 5H-pyrido[1,2,3-de]quinoxaline-2,3-dione A procedure similar to that described in Example 51 was carried out with 9-bromo-5-carboxymethyl-6,7-dihydro-1H, 5H-pyrido[1,2,3-de]quinoxaline-2,3-dione (340 mg, 1 mmol) and o-sulfamoylaniline (180 mg, 1.05 mmol) to give 85 mg of the title compound (17%) after silica gel column chromatography of the crude product with 1% acetic acid/ethyl acetate as an eluent: mp>270° C.; $^1$H NMR (270 MHz, DMSO-d$_6$) δ12.06 (bs, 1H), 9.36 (s, 1H), 8.01 (d, 1H, J=8.1 Hz), 7.85 (d, 2H, J=8.1 Hz), 7.60 (t, 1H, J=8.1 Hz), 7.58 (s, 2H), 7.32 (t, 1H, J=8.1 Hz), 7.23 (d, 1H, J=2 Hz), 7.16 (d, 1H, J=2 Hz), 5.17~5.27 (m, 1H), 3.07 (ddd, 1H, J=17.1, 13.5, 4.5 Hz), 2.82 (dm, 1H, J=17.1 Hz), 2.71~2.76 (m, 2H), 2.12 (dm, 1H, J=13.5 Hz), 1.78~1.96 (m, 1H).

EXAMPLE 60

9-Bromo-5-(m-sulfamoylphenylcarbamoylmethyl)-6,7-dihydro-1H, 5H-pyrido[1,2,3-de]quinoxaline-2,3-dione A procedure similar to that described in Example 51 was carried out with 9-bromo-5-carboxymethyl-6,7-dihydro-1H, 5H-pyrido[1,2,3-de]quinoxaline-2,3-dione (170 mg, 0.5 mmol) and m-sulfamoylaniline (100 mg, 0.58 mmol) to give 209 mg of the title compound (85%): mp>270° C.; $^1$H NMR (270 MHz, DMSO-d$_6$) δ12.07 (s, 1H), 10.33 (s, 1H), 8.13 (s, 1H), 7.70~7.78 (m, 1H), 7.45~7.55 (m,2H), 7.24 (bs, 1H), 7.15 (bs, 1H), 5.15~5.28 (m, 1H), 3.06 (ddd, 1H, J=17.1, 13.5, 4.5 Hz), 2.83 (dm, 1H, J=16.8 Hz), 2.65 (dd, 1H, J=18, 13.5 Hz), 2.58 (dd, 1H, J=18, 5.4 Hz), 2.12 (dm, 1H, J=13.5 Hz), 1.80~1.97 (m, 1H).

EXAMPLE 61

9-Bromo-5-(p-sulfamoylphenylcarbamoylmethyl)-6,7-dihydro-1H, 5H-pyrido[1,2,3-de]quinoxaline-2,3-dione A procedure similar to that described in Example 51 was carried out with 9-bromo-5-carboxymethyl-6,7-dihydro-1H, 5H-pyrido[1,2,3-de]quinoxaline-2,3-dione (170 mg, 0.5 mmol) and p-sulfamoylaniline (87 mg, 0.506 mmol) to give 190 mg of the title compound (77%): mp 263°~267° C.; $^1$H NMR (270 MHz, DMSO-$d_6$) δ12.07 (s, 1H), 10.21 (s, 1H), 8.20 (bs, 1H), 7.81 (d, 1H, J=8.0 Hz), 7.63 (d, 1H, J=8.0 Hz), 7.24 (bs, 2H), 7.19 (bs, 2H), 5.17~5.28 (m, 1H), 3.06 (ddd, 1H, J=17.1, 13.5, 4.5 Hz), 2.83 (dm, 1H, J=16.8 Hz), 2.55~2.70 (m, 2H), 2.12 (dm, 1H, J=13.5 Hz), 1.80~1.97 (m, 1H).

EXAMPLE 62

9-Bromo-5-(o-methoxyphenylcarbamoylmethyl)-6,7-dihydro-1H, 5H-pyrido[1,2,3-de]quinoxaline-2,3-dione A procedure similar to that described in Example 5 was carried out with 9-bromo-5-carboxymethyl-6,7-dihydro-1H, 5H-pyrido[1,2,3-de]quinoxaline-2,3-dione (150 mg, 0.442 mmol) and o-methoxyaniline (76 mg, 0.62 mmol) to give 170 mg of the title compound (86%): mp>270° C.; $^1$H NMR (270 MHz, DMSO-$d_6$) δ12.06 (bs, 1H), 9.27 (s, 1H), 7.88 (d, 1H, J=8.1 Hz), 7.24 (s, 1H), 7.17 (s, 1H), 7.08 (t, 1H, J=8.1 Hz), 7.03 (d, 1H, J=8.1 Hz), 6.90 (t, 1H, J=8.1 Hz), 5.16~5.27 (m, 1H), 3.81 (s, 3H), 3.12 (ddd, 1H, J=17.1, 13.5, 4.5 Hz), 2.81 (dm, 1H, J =17.1 Hz), 2.77 (dd, 1H, J=13.5, 10.8 Hz), 2.62 (dd, 1H, J=13.5, 5.4 Hz), 2.11 (dm, 1H, J=13.5 Hz), 1.77~1.95 (m, 1H).

EXAMPLE 63

9-Bromo-5-(m-methoxyphenylcarbamoylmethyl)-6,7-dihydro-1H, 5H-pyrido[1,2,3-de]quinoxaline-2,3-dione A procedure similar to that described in Example 5 was carried out with 9-bromo-5-carboxymethyl-6,7-dihydro-1H, 5H-pyrido[1,2,3-de]quinoxaline-2,3-dione (150 mg, 0.442 mmol) and m-methoxyaniline (76 mg, 0.62 mmol) to give 190 mg of the title compound (95%): mp 151°~154° C.; $^1$H NMR (270 MHz, DMSO-$d_6$) δ12.07 (s, 1H), 10.00 (s, 1H), 7.27 (d, 1H, J=2 Hz), 7.24 (bs, 1H), 7.20 (t, 1H, J=8.1 Hz), 7.16 (bs, 1H), 6.64 (dd, 1H, J=8.1, 2 Hz), 6.88 (d, 2H, J =9 Hz), 5.16~5.17 (m, 1H), 3.72 (s, 3H), 3.05 (ddd, 1H, J=17.1, 13.5, 4.5 Hz), 2.82 (dm, 1H, J=16.8 Hz), 2.55~2.65 (m, 2H), 2.09 (dm, 1H, J=13.5 Hz), 1.80~1.96 (m, 1H).

EXAMPLE 64

9-Bromo-5-(p-methoxyphenylcarbamoylmethyl)-6,7-dihydro-1H, 5H-pyrido[1,2,3-de]quinoxaline-2,3-dione A procedure similar to that described in Example 5 was carried out with 9-bromo-5-carboxymethyl-6,7-dihydro-1H, 5H-pyrido[1,2,3-de]quinoxaline-2,3-dione (150 mg, 0.442 mmol) and p-methoxyaniline (70 mg, 0.57 mmol) to give 179 mg of the title compound (91%): mp>270° C.; $^1$H NMR (270 MHz, DMSO-$d_6$) δ12.06 (s, 1H), 9.86 (s, 1H), 7.46 (d, 2H, J=9 Hz), 7.24 (d, 1H, J=2 Hz), 7.16 (d, 1H, J=2 Hz), 6.88 (d, 2H, J=9 Hz), 5.15~5.25 (m, 1H), 3.72 (s, 3H), 3.05 (ddd, 1H, J=17.1, 13.5, 4.5 Hz), 2.83 (dm, 1H, J=16.8 Hz), 2.50~2.64 (m, 2H), 2.09 (dm, 1H, J=13.5 Hz), 1.78~1.94 (m, 1H).

EXAMPLE 65

9-Bromo-5-(o-acetylphenylcarbamoylmethyl)-6,7-dihydro-1H, 5H-pyrido[1,2,3-de]quinoxaline-2,3-dione A procedure similar to that described in Example 51 was carried out with 9-bromo-5-carboxymethyl-6,7-dihydro-1H, 5H-pyrido[1,2,3-de]quinoxaline-2,3-dione (170 mg, 1 mmol) and o-acetylaniline (90 mg, 0.67 mmol) to give 50 mg of the title compound (21%) after chromatography of the crude product on a silica gel column with 1% acetic acid/ethyl acetate as an eluent: mp>270° C.; $^1$H NMR (270 MHz, DMSO-$d_6$) δ12.06 (bs, 1H), 11.12 (s, 1H), 8.20 (bd, 1H, J=8.1 Hz), 7.96 (d, 2H, J=8.1 Hz), 7.60 (t, 1H, J=8.1 Hz), 7.23 (t, 1H, J=8.1 Hz), 7.23 (d, 1H, J =2 Hz), 7.17 (d, 1H, J=2 Hz), 5.14~5.26 (m, 1H), 3.04 (ddd, 1H, J=17.1, 13.5, 4.5 Hz), 2.83 (dm, 1H, J=17.1 Hz), 2.64~2.76 (m, 2H), 2.60 (s, 3H), 2.16 (dm, 1H, J=13.5 Hz), 1.82~1.97 (m, 1H).

EXAMPLE 66

9-Bromo-5-(m-acetylphenylcarbamoylmethyl)-6,7-dihydro-1H, 5H-pyrido[1,2,3-de]quinoxaline-2,3-dione A procedure similar to that described in Example 51 was carried out with 9-bromo-5-carboxymethyl-6,7-dihydro-1H, 5H-pyrido[1,2,3-de]quinoxaline-2,3-dione (170 mg, 0.5 mmol) and m-acetylaniline (80 mg, 0.59 mmol) to give 200 mg of the title compound (85%): mp>270° C.; $^1$H NMR (270 MHz, DMSO-$d_6$) δ12.07 (bs, 1H), 10.23 (s, 1H), 8.12 (bs, 1H), 7.85 (d, 1H, J=8.1 Hz), 7.68 (d, 1H, J=8.1 Hz), 7.47 (t, 1H, J=8.1 Hz), 7.24 (d, 1H, J=2 Hz), 7.17 (d, 1H, J=2 Hz), 5.18~5.28 (m, 1H), 3.06 (ddd, 1H, J=17.1, 13.5, 4.5 Hz), 2.83 (dm, 1H, J=17.1 Hz), 2.55~2.70 (m, 2H), 2.56 (s, 3H), 2.12 (dm, 1H, J=13.5 Hz), 1.81~1.96 (m, 1H).

EXAMPLE 67

9-Bromo-5-(p-acetylphenylcarbamoylmethyl)-6,7-dihydro-1H, 5H-pyrido[1,2,3-de]quinoxaline-2,3-dione A procedure similar to that described in Example 51 was carried out with 9-bromo-5-carboxymethyl-6,7-dihydro-1H, 5H-pyrido[1,2,3-de]quinoxaline-2,3-dione (170 mg, 0.5 mmol) and p-acetylaniline (80 mg, 0.59 retool) to give 90 mg of the title compound (38%): mp>270° C.; $^1$H NMR (270 MHz, DMSO-$d_6$) δ12.07 (s, 1H), 10.35 (s, 1H), 7.93 (d, 2H, J=9 Hz), 7.70 (d, 1H, J=9 Hz), 7.24 (d, 1H, J=2 Hz), 7.17 (d, 2H, J=9 Hz), 5.17~5.27 (m, 1H), 3.05 (ddd, 1H, J=17.1, 13.5, 4.5 Hz), 2.83 (dm, 1H, J=16.8 Hz), 2.65 (d, 2H, J=6.9 Hz), 2.53 (s, 3H), 2.12 (dm, 1H, J=13.5 Hz), 1.80~1.97 (m, 1H).

EXAMPLE 68

9-Bromo-5-(N-hydroxycarbamoylmethyl)-6,7-dihydro-1H, 5H-pyrido[1,2,3-de]quinoxaline-2,3-dione 9-Bromo-5-(O-tetrahydropyranyl-N-hydroxycarbamoylmethyl)-6,7-dihydro-1H, 5H-pyrido[1,2,3-de]quinoxaline-2,3-dione (Example 37, 60 mg, 0.136 mmol) in methanol (5 mL) was treated with a few drops of concentrated hydrochloric acid and the solution was concentrated in vacuo to give 46 mg of the title compound (96%): mp 124°~126° C. (dec); $^1$H NMR (270 MHz, DMSO-d$_6$) δ12.08 (bs, 1H), 10.20 (bs, 1H), 10.00 (bs, 1H), 7.20 (d, 1H, J=2 Hz), 7.16 (d, 1H, J=2 Hz), 5.03~5.14 (m, 1H), 2.95 (ddd, 1H, J=17.1, 13.5, 4.5 Hz), 2.77 (dm, 1H, J=17.1 Hz), 2.40~2.63 (m, 2H), 2.10 (dm, 1H, J=13.5 Hz), 1.78~1.96 (m, 1H).

EXAMPLE 69

9-Bromo-5-(O-methyl-N-hydroxycarbamoylmethyl)-6,7-dihydro-1H, 5H-pyrido[1,2,3-de]quinoxaline-2,3-dione A procedure similar to that described in Example 51 was carried out with 9-Bromo-5-carboxymethyl-6,7-dihydro-1H, 5H-pyrido[1,2,3-de]quinoxaline-2,3-dione (340 mg, 1.0 mmol) and N,O-dimethylhydroxylamine hydrochloride (120 mg, 1.23 mmol) to give 210 mg of the title compound (55%): mp 147°~151° C.; $^1$H NMR (270 MHz, DMSO-d$_6$) δ12.25 (bs, 1H), 7.21 (bs, 1H), 7.19 (bs, 1H), 5.54~5.60 (m, 1H), 3.88 (s, 3H), 2.89 (s, 3H), 2.84 (dm, 1H, J=16.8 Hz), 2.50~2.70 (m, 1H), 2.34 (dm, 1H, J=13.5 Hz), 2.00~2.16 (m, 1H).

EXAMPLE 70 trans-9-Bromo-5-methoxycarbonylmethyl-6-methyl-6,7-dihydro-1H, 5H-pyrido[1,2,3-de]quinoxaline-2,3-dione;

1) N-Benzoyl-2-cyano-3-methyl-1,2-dihydroquinoline

To a mixture of potassium cyanide (68.22 g, 1.048 mol), and 3-methylquinoline (50 g, 0.349 mol) in water (200 mL) and dichloromethane (500 mL) was added dropwise benzoyl chloride (81 mL, 0.698 mol) over 2 h at room temperature. The mixture was stirred for 4.5 h at room temperature and then the organic layer was separated. The layer was washed successively with water (300 mL), 1N aqueous hydrochloric acid, and water (200 mL×2), dried over magnesium sulfate, and concentrated to give 103.05 g of N-benzoyl-2-cyano-3-methyl-1,2-dihydroquinoline (108%): $^1$H NMR (270 MHz, CDCl$_3$) δ7.34 (m, 6H), 7.16 (dd, 1H, J=7.6, 1.3 Hz), 7.07 (dt, 1H, J=1.3, 7.6 Hz), 6.87 (dt, 1H, J=1.3, 7.6 Hz), 6.53 (dd, 1H, J=7.6, 1.3 Hz), 2.12 (d, 3H, J=1.3 Hz).

2) 2-Methoxycarbonyl-3-methylquinoline

A solution of N-benzoyl-2-cyano-3-methyl-1,2-dihydroquinoline (103.05 g) in concentrated hydrochloric acid (300 mL) was refluxed for 19 h during which time 400 mL of concentrated hydrochloric acid was occasionally added by portions. The mixture was concentrated in vacuo and the trace amount of water and volatile impurities were removed by azeotropic distillation with toluene. The residue was rinsed with acetone (500 mL), dried in vacuo, and dissolved in methanol (800 mL). Thionyl chloride (88.33 g, 0.743 mol) was added dropwise over 30 min at 0° C. and the mixture was refluxed for 6 h. After the solvent was evaporated off, the residue was dissolved in water and adjusted to pH 8 by using saturated aqueous sodium bicarbonate. The mixture was extracted with ethyl acetate. The organic layer was washed with brine, dried over magnesium sulfate, and concentrated to give 36.85 g of 2-methoxycarbonyl-3-methylquinoline (52% from 3-methylquinoline): $^1$H NMR (270 MHz, CD$_3$OD) δ9.27 (s, 1H), 8.54 (dd, 1H, J=8.9, 1 Hz), 8.34 (d, 1H, J=8.9 Hz), 8.19 (dt, 1H, J=1, 8.9 Hz), 5.11 (dt, 1H, J=1, 8.9 Hz), 4.22 (s, 3H), 2.93 (d, 3H, J=1Hz).

3) cis-2-Methoxycarbonyl-3-methyltetrahydroquinoline

2-Methoxycarbonyl-3-methylquinoline (30 g, 0.149 mol) in acetic acid (300 mL) was hydrogenated over platinum oxide (1 g) under atmospheric pressure of hydrogen at room temperature until the theoretical amount of hydrogen was consumed. The mixture was passed through celite and concentrated in vacuo. The residue was purified by silica gel column chromatography with 20:1 to 10:1 hexane/ethyl acetate to give 23.93 g of cis-2-methoxycarbonyl-3-methyltetrahydroquinoline (78%): $^1$H NMR (270 MHz, CDCl$_3$) d 6.99 (m, 2H), 6.64 (t, 1H, J=7.9 Hz), 6.58 (d, 1H, J=7.9 Hz), 4.34 (s, 1H), 4.09 (t, 1H, J=2.5 Hz), 3.06 (dd, 1H, J=16.9, 5.8 Hz), 2.55 (m, 1H), 2.50 (dd, 1H, J=16.9, 3.3 Hz), 0.88 (d, 3H, J=6.9 Hz).

4) trans-2-Methoxycarbonyl-3-methyltetrahydroquinoline

To a solution of cis-2-methoxycarbonyl-3-methyltetrahydroquinoline (8.36 g, 40.7 mmol) in methanol (65 mL) was added sodium methoxide (14.8 mmol) in methanol (20 mL) at room temperature. The mixture was refluxed for 3 h and allowed to cool to room temperature. Thionyl chloride (7.23 mL, 99.2 mmol) was added and the resulting mixture was refluxed for 3 h. After the solvent was evaporated, the residue was dissolved in water and adjusted to pH 8 by using saturated aqueous sodium bicarbonate. The mixture was extracted with ethyl acetate. The organic layer was washed with: water and brine, dried over magnesium sulfate, and concentrated. The residue was purified by column chromatography with 15:1 hexane/ethyl acetate to give 3.94 g of cis-2-methoxycarbonyl-3-methyltetrahydroquinoline (47%) and 3.17 g of trans-2-methoxycarbonyl-3-methyltetrahydroquinoline (38%): $^1$H NMR (270 MHz, CDCl$_3$) δ7.00 (td, 1H, J=7.3, 1 Hz), 6.93 (dd, 1H, J=7.3, 1Hz), 6.65 (td, 1H, J=7.3, 1 Hz), 6.58 (dd, 1H, J=7.3, 1 Hz), 4.22 (s, 1H), 3.74 (s, 3H), 3.70 (dd, 1H, J=5.9, 2.1 Hz), 2.79 (dd, 1H, J=15.8, 4.6 Hz), 2.44 (dd, 1H, J=15.8, 6.3 Hz), 2.35 (qddd, 1H, J=6.6, 6.3, 5.9, 4.6 Hz), 1.11 (d, 3H, J=6.6 Hz).

5) trans-9-Bromo-5-methoxycarbonylmethyl-6-methyl-6,7-dihydro-1H, 5H-pyrido[1,2,3-de]quinoxaline-2,3-dione The title compound was prepared by the route outlined in Example 22 starting with trans-2-methoxycarbonyl-3-methyltetrahydroquinoline. In nitration step of Example 22-5, conditions of nitronium tetrafluoroborate in dichloromethane at room temperature were employed instead of those of refluxing ammonium nitrate-trifluoroacetic anhydride in chloroform: mp 193°~195° C.; $^1$H NMR (270 MHz, DMSO-d$_6$) δ12.07 (bs, 1H), 7.18 (s, 1H), 7.15 (s, 1H), 4.78~4.88 (m, 1H), 3.61 (s, 3H), 3.11 (dd, 1H, J=17.5, 4.6 Hz), 2.40~2.65 (m, 3H), 2.30~2.40 (m, 1H), 0.86 (d, 3H, J=6.9 Hz).

EXAMPLE 71 trans-9-Bromo-5-carboxymethyl-6-methyl-6,7-dihydro-1H, 5H-pyrido[1,2,3-de]quinoxaline-2,3-dione Hydrolysis of trans-9-Bromo-5-methoxycarbonylmethyl-6-methyl-6,7-dihydro- 1H, 5H-pyrido[1,2,3-de]quinoxaline-2,3-dione (360 mg, 0.98 mmol) was carried out as described in Example 3 to give 335 mg of the title compound (97%): mp 262.5°~265.5° C.; $^1$H NMR (270 MHz, CD$_3$OD) δ7.21 (s, 2H), 4.98~5.08 (m, 1H), 3.24 (dd, 1H, J=17.3, 5.4 Hz), 2.70 (dd, 1H, J=15.3, 4.8 Hz), 2.63 (dd, 1H, J=17.3, 1.6 Hz), 2.53 (dd, 1H, J=15.3, 4.8 Hz), 2.45~2.57 (m, 1H), 0.86 (d, 3H, J=6.9 Hz).

EXAMPLE 72 trans-9-Bromo-6-methyl-5-phenylcarbamoylmethyl-6,7-dihydro-1H, 5H-pyrido[ 1,2,3-de]quinoxaline-2,3-dione A procedure similar to that described in Example 5 was carried out with trans-9-bromo-5-carboxymethyl-6-methyl- 6,7-dihydro-1H, 5H-pyrido[1,2,3-de]quinoxaline-2,3-dione (100 mg, 0.283 mmol) and aniline (28 mL, 0.311 mmol) to give 112 mg of the title compound (92%): mp>300° C.; $^1$H NMR (270 MHz, DMSO-d$_6$) δ12.08 (s, 1H), 9.99 (s, 1H), 7.55 (d, 2H, J=7.6 Hz), 7.30 (t, 2H, J=7.6 Hz), 7.21 (s, 1H), 7.17 (s, 1H), 7.05 (t, 1H, J=7.6 Hz), 4.92~5.02 (m, 1H), 3.25 (dd, 1H, J=17.8, 5.9 Hz), 2.50~2.66 (m, 3H), 2.28~2.42 (m, 1H), 0.86 (d, 3H, J=6.9 Hz).

EXAMPLE 73 cis-9-Bromo-5-methoxycarbonylmethyl-6-methyl-6,7-dihydro-1H, 5H-pyrido[1,2,3-de]quinoxaline-2,3-dione The title compound was prepared by the route outlined in Example 22 starting with trans-2-methoxycarbonyl-3-methyltetrahydroquinoline. In nitration step of Example 22-6, conditions of nitronium tetrafluoroborate in dichloromethane at room temperature were employed instead of those of refluxing ammonium nitrate-trifluoroacetic anhydride in chloroform: mp 190°~198° C. (dec); $^1$H NMR (270 MHz, CDCl$_3$) δ11.40 (bs, 1H), 7.34 (s, 1H), 7.15 (s, 1H), 5.33~5.43 (m, 1H), 3.66 (s, 3H), 2.79 (dd, 1H, J=17.5, 5.6 Hz), 2.62~2.76 (m, 2H), 2.29 (dd, 1H, J=13.9, 7,9 Hz), 2.20~2.38 (m, 1H), 1.24 (d, 3H, J=6.9 Hz).

EXAMPLE 74 cis-9-Bromo-5-carboxymethyl-6-methyl-6,7-dihydro-1H, 5H-pyrido[1,2,3-de]quinoxaline-2,3-dione Hydrolysis of cis-9-bromo-5-methoxycarbonylmethyl-6-methyl-6,7-dihydro-1H, 5H-pyrido[1,2,3-de]quinoxaline-2,3-dione (2.29 g, 6.24 mmol) was carried out as described in Example 3 to give 2.24 g of the title compound (100%): mp 258.5°~266.5° C.; $^1$H NMR (270 MHz, CD$_3$OD) δ7.19 (s, 2H), 5.33 (ddd, 1H, J=6.6, 6.3, 4.3 Hz), 2.81 (dd, 1H, J=17.2, 6.1 Hz), 2.74 (dd, 1H, J=17.2, 11.3 Hz), 2.63 (dd, 1H, J=14.8, 6.3 Hz), 2.30 (dd, 1H, J=14.8, 6.6 Hz), 2.22~2.32 (m, 1H), 1.21 (d, 3H, J=6.9 Hz).

EXAMPLE 75 cis-9-Bromo-6-methyl-5-phenylcarbamoylmethyl-6,7-dihydro-1H, 5H-pyrido[1,2,3-de]quinoxaline-2,3-dione A procedure similar to that described in Example 5 was carried out with cis-9-bromo-5-carboxymethyl-6-methyl-6,7-dihydro-1H, 5H-pyrido[1,2,3-de]quinoxaline-2,3-dione (100 mg, 0.283 mmol) and aniline (28 μL, 0.311 mmol) to give 108 mg of the title compound (89%): mp>300° C.; $^1$H NMR (270 MHz, DMSO-d$_6$) δ12.03 (s, 1H), 9.89 (s, 1H), 7.45 (d, 2H, J=7.6 Hz), 7.27 (t, 2H, J=7.6 Hz), 7.19 (d, 1H, J=2 Hz), 7.17 (d, 1H, J=2 Hz), 7.02 (t, 1H, J=7.6 Hz), 5.16~5.26 (m, 1H), 2.70~2.85 (m, 2H), 2.63 (dd, 1H, J=14.2, 5.9 Hz), 2.24 (dd, 1H, J=14.2, 6.6 Hz), 2.10~2.26 (m, 1H), 1.13 (d, 3H, J=6.9 Hz).

EXAMPLE 76 trans-9-Bromo-5-methoxycarbonylmethyl-7-methyl-6,7-dihydro-1H, 5H-pyrido[1,2,3-de]quinoxaline-2,3-dione 1) cis-2-methoxycarbonyl-4-methyltetrahydroquinoline To a solution of 2-methoxycarbonyl-4-methylquinoline[a] (17.19 g, 85.43 mmol) in methanol (200 mL)in the presence of NiCl$_2$-6H$_2$O (3.66 g, 15.38 mmol) was added sodium borohydride (9.70 g, 256.29 mmol) at 0° C. by portions. The mixture was stirred for 2 h and the unreacted reagent was destroyed by addition of 1N hydrochloric acid. The mixture was adjusted to pH 11 by using aqueous ammonia and extracted with ethyl acetate. The organic layer was washed with water and brine, dried over magnesium sulfate, and concentrated. The residue was purified by silica gel column chromatography with 20:1 to 1:1 hexane/ethyl acetate to give 7.27 g of cis-2-methoxycarbonyl-4-methyltetrahydroquinoline together with the starting material (2.41 g): $^1$H NMR (270 MHz, CDCl$_3$) δ7.12 (dd, 1H, J=7, 1 Hz), 7.01 (dt, 1H, J=1, 7 Hz), 6.69 (dt, 1H, J=1, 7 Hz), 6.58 (dd, 1H, J=7, 1 Hz), 4.38 (bs, 1H), 4.11 (dd, 1H, J=11, 4 Hz), 3.79 (s, 3H), 2.98 (ddq, 1H, J=11, 5, 6 Hz), 2.35 (ddd, 1H, J=13, 5, 4 Hz), 1.66 (q, 1H, J=11 Hz), 1.34 (d, 3H, J=6 Hz). [a]F. D. Popp et al., J. Org. Chem., 26, 4930 (1961).

2) trans-2-Methoxycarbonyl-4-methyltetrahydroquinoline

Epimerization of cis-2-methoxycarbonyl-4-methyltetrahydroquinoline (14.16 g, 0.069 mol) was carried out as described in Example 70-4 to give a 1:1 mixture of cis and trans-2-methoxycarbonyl-4-methyltetrahydroquinoline (14.75 g). Pure trans-2-methoxycarbonyl-4-methyltetrahydroquinoline (2.02 g) was obtained by silica gel column chromatography of the mixture: $^1$H NMR (270 MHz, CDCl$_3$) δ7.03 (dd, 1H, J=1, 7 Hz), 7.01 (dt, 1H, J=1, 7 Hz), 6.67 (dt, 1H, J=1, 7 Hz), 7.61 (dd, 1H, J=1, 7 Hz), 4.41 (bs, 1H), 4.08 (t, 1H, J=7 Hz), 3.78 (s, 3H), 2.94 (ddq, 1H, J=12, 5, 7 Hz), 2.02 (m, 2H), 1.30 (d, 3H, J=7 Hz).

3) trans-9-Bromo-5-methoxycarbonylmethyl-7-methyl-6,7-dihydro-1H, 5H-pyrido[1,2,3-de]quinoxaline-2,3-dione The title compound was prepared by the route outlined in Example 22 starting with trans-2-methoxycarbonyl-4-methyltetrahydroquinoline. In nitration step of Example 22-6, conditions of nitronium tetrafluoroborate in dichloromethane at room temperature were employed instead of those of refluxing ammonium nitrate-trifluoroacetic anhydride in chloroform: mp 194°~195° C.; $^1$H NMR (270 MHz, DMSO-d$_6$) δ11.20 (bs, 1H), 7.34 (s, 1H), 7.31 (s, 1H), 5.34~5.44 (m, 1H), 3.70 (s, 3H), 3.07 (ddq, 1H, J=12.5, 4.6, 6.6 Hz), 2.83 (dd, 1H, J=14.8, 5.0 Hz), 2.58 (dd, 1H, J=14.8, 9.5 Hz), 2.30 (ddd, 1H, J=14.2, 4.6, 2,3 Hz), 1.78 (ddd, 1H, J=14.2, 12.5, 4.9 Hz), 1.43 (d, 3H, J=6.6 Hz).

EXAMPLE 77 trans-9-Bromo-5-carboxymethyl-7-methyl-6,7-dihydro-1H, 5H-pyrido[1,2,3-de]quinoxaline-2,3-dione Hydrolysis of trans-9-bromo-5-methoxycarbonylmethyl-7-methyl-6,7-dihydro-1H, 5H-pyrido[1,2,3-de]quinoxaline-2,3-dione (200 mg, 0.545 mmol) was carried out as described in Example 3 to give 192 mg of the title compound (100%): mp 287°~291° C. (dec); $^1$H NMR (270 MHz, DMSO-d$_6$) δ11.20 (bs, 1H), 7.34 (s, 1H), 7.22 (s, 1H), 5.21~5.31 (m, 1H), 3.15 (ddq, 1H, J=12.2, 4.6, 6.6 Hz), 2.75 (dd, 1H, J=15.5, 4.3 Hz), 2.61 (dd, 1H, J=15.5, 9.9 Hz), 2.31 (ddd, 1H, J=14.2, 4.6, 2.3 Hz), 1.77 (ddd, 1H, J=14.2, 12.2, 4.9 Hz), 1.41 (d, 3H, J=6.6 Hz).

EXAMPLE 78 trans-9-Bromo-7-methyl-5-phenylcarbamoylmethyl-6,7-dihydro-1H, 5H-pyrido[1,2,3-de]quinoxaline-2,3-dione A procedure similar to that described in Example 5 was carried out with trans-9-bromo-5-carboxymethyl-7-methyl-6,7-dihydro-1H, 5H-pyrido[1,2,3-de]quinoxaline-2,3-dione (90 mg, 0.255 mmol) and aniline (25 μL, 0.28 mmol) to give 96 mg of the title compound (88%): mp>300° C.; $^1$H NMR (270 MHz, DMSO-d$_6$) δ12.09 (bs, 1H), 7.56 (d, 2H, J=7.3 Hz), 7.32 (d, 1H, J=2 Hz), 7.30 (t, 2H, J=7.3 Hz), 7.21 (d, 1H, J=2 Hz), 7.05 (t, 1H, J=7.3 Hz), 5.15~5.25 (m, 1H), 3.19 (ddq, 1H, J=12.5, 4.6, 6.6 Hz), 2.55~2.70 (m, 2H), 2.13 (ddd, 1H, J=14.2, 4.6, 2.3 Hz), 1.67 (ddd, 1H, J=14.2, 12.5, 4.9 Hz), 1.33 (d, 3H, J=6.3 Hz).

EXAMPLE 79 cis-9-Bromo-5-methoxycarbonylmethyl-7-methyl-6,7-dihydro-1H, 5H-pyrido[1,2,3-de]quinoxaline-2,3-dione The title compound was prepared by the route outlined in Example 70-5 starting with cis-2-methoxycarbonyl-4-methyltetrahydroquinoline: mp 174°~175° C.; $^1$H NMR (270 MHz, DMSO-d$_6$) δ11.90 (bs, 1H), 7.37 (d, 1H, J=2 Hz), 7.20 (d, 1H, J=2 Hz), 5.22~5.32 (m, 1H), 3.73 (s, 3H), 3.00~3.16 (m, 1H), 3.00 (dd, 1H, J=15.7, 5.3 Hz), 2.70 (dd, 1H, J=15.7, 9.2 Hz), 2.30 (dt, 1H, J=14.0, 5.3 Hz), 2.15 (dt, 1H, J=14.0, 2.0 Hz), 1.47 (d, 3H, J=7.6 Hz).

EXAMPLE 80 cis-9-Bromo-5-carboxymethyl-7-methyl-6,7-dihydro-1H, 5H-pyrido[1,2,3-de]quinoxaline-2,3-dione Hydrolysis of cis-9-bromo-5-methoxycarbonylmethyl-7-methyl-6,7-dihydro-1H, 5H-pyrido[1,2,3-de]quinoxaline-2,3-dione (400 mg, 1.09 mmol) was carried out as described in Example 3 to give 397 mg of the title compound (100%): mp 287.5°~288° C. (dec); $^1$H NMR (270 MHz, DMSO-d$_6$) δ12.46 (bs, 1H), 12.06 (bs, 1H), 7.27 (d, 1H, J=2.3 Hz), 7.15 (d, 1H, J=2.3 Hz), 4.92~5.02 (m, 1H), 3.00~3.16 (m, 1H), 2.75 (dd, 1H, J=16.2, 4.6 Hz), 2.51 (dd, 1H, J=16.2, 9.9 Hz), 2.18 (dt, 1H, J=14.7, 5.6 Hz), 2.03 (dt, 1H, J=14.7, 2 Hz), 1.40 (d, 3H, J=7.3 Hz).

EXAMPLE 81 cis-9-Bromo-7-methyl-5-phenylcarbamoylmethyl-6,7-dihydro-1H, 5H-pyrido-1,2,3-de]quinoxaline-2,3-dione A procedure similar to that described in Example 5 was carried out with cis-9-bromo-5-carboxymethyl-7-methyl-6,7-dihydro-1H, 5H-pyrido[1,2,3-de]quinoxaline-2,3-dione (150 mg, 0.425 mmol) and aniline (42 μL, 047 mmol) to give 170 mg of the title compound (93%): mp 276.5° C. (dec); $^1$H NMR (270 MHz, DMSO-d$_6$) δ12.11 (bs, 1H), 7.55 (d, 2H, J=7.6 Hz), 7.30 (t, 2H, j+7.6 Hz), 7.29 (d, 1H, J=2.3 Hz), 7.20 (d, 1H, J=2.3 Hz), 7.04 (t, 1H, J=7.6 Hz), 5.11~5.21 (m, 1H), 2.99~3.15 (m, 1H), 2.80 (dd, 1H, J=15.2, 5.6 Hz), 2.67 (dd, 1H, J=15.2, 8.9 Hz), 2.20 (dt, 1H, J=14.5, 6.0 Hz), 2.04 (dt, 1H, J=14.5, 2 Hz), 1.45 (d, 3H, J=7.3 Hz).

EXAMPLE 82

9-Bromo-5-(O-benzyl-N-hydroxycarbamoylmethyl)-6,7-dihydro-1H, 5H-pyrido-[1,2,3-de]quinoxaline-2,3-dione A procedure similar to that described in Example 5 was carried out with 9-bromo-5-carboxymethyl-6,7-dihydro-1H, 5H-pyrido[1,2,3-de]quinoxaline-2,3-dione (150 mg, 0.425 mmol) and O-benzylhydroxylamine (100 mg, 0.627 mmol) to give 120 mg of the title compound (61%): mp 144°~146° C.; $^1$H NMR (270 MHz, DMSO-d$_6$) δ12.05 (bs, 1H), 11.10 (s, 1H) 7.28~7.48 (m, 5H), 7.20 (bs, 1H), 7.15 (bs, 1H), 5.04~5.16 (m, 1H), 4.80 (d, 1H, J=10.8 Hz), 4.77 (d, 1H, J=10.8 Hz), 2.90 (ddd, 1H, J=17.1, 13.5, 4.5 Hz), 2.76 (dm, 1H, J=17.1 Hz), 2.33 (d, 1H, J=5.4 Hz), 2.16 (d, 1H, 14.4 Hz), 1.96 (dm, 1H, J=13.5 Hz), 1.73~1.89 (m, 1H).

EXAMPLE 83

9-Bromo-5-(2-pyridylcarbamoylmethyl)-6,7-dihydro-1H, 5H-pyrido[1,2,3-de]quinoxaline-2,3-dione A procedure similar to that described in Example 52 was carried out with 9-bromo-5-carboxymethyl-6,7-dihydro-1H, 5H-pyrido[1,2,3-de]quinoxaline-2,3-dione (680 mg, 2 mmol) and 2-aminopyridine (200 mg, 2 mmol) to give 460 mg of the title compound (55%): mp>270° C.; $^1$H NMR (270 MHz, DMSO-d$_6$) δ12.08 (bs, 1H), 10.58 (s, 1H), 8.31 (d, 1H, J=4.6 Hz), 8.07 (t, 2H, J=8.1 Hz), 7.79 t, 1H, J=8.1 Hz), 7.24 (d, 1H, J=2 Hz), 7.17 (d, 1H, J=2 Hz), 7.10 (dd, 1H, J=4.6, 8.1 Hz), 5.17~5.27 (m, 1H), 3.06 (ddd, 1H, J=17.1, 13.5, 4.5 Hz), 2.81 (dm, 1H, J=17.1 Hz), 2.76 (dd, 1H, J=13.5, 7.2 Hz), 2.57 (dd, 1H, J=13.5, 5.4 Hz), 2.07 (dm, 1H, J=13.5 Hz), 1.80~1.94 (m, 1H).

EXAMPLE 84

9-Bromo-5-(3-pyridylcarbamoylmethyl)-6,7-dihydro-1H, 5H-pyrido[1,2,3-de]quinoxaline-2,3-dione A procedure similar to that described in Example 51 was carried out with 9-bromo-5-carboxymethyl-6,7-dihydro-1H, 5H-pyrido[1,2,3-de]quinoxaline-2,3-dione (170 mg, 0.5 mmol) and 3-aminopyridine (60 mg, 0.64 mmol) to give 170 mg of the title compound (80%): mp>270° C.; $^1$H NMR (270 MHz, DMSO-d$_6$) δ12.08 (bs, 1H), 10.58 (s, 1H), 8.31 (d, 1H, J=4.6 Hz), 8.07 (t, 2H, J=8.1 Hz), 7.79 (t, 1H, J=8.1 Hz), 7.24 (d, 1H, J=2 Hz), 7.17 (d, 1H, J=2 Hz), 7.10 (dd, 1H, J=4.6, 8.1 Hz), 5.17~5.27 (m, 1H), 3.06 (ddd, 1H, J=17.1, 13.5, 4.5 Hz), 2.81 (dm, 1H, J=17.1 Hz), 2.76 (dd, 1H, J=13.5, 7.2 Hz), 2.57 (dd, 1H, J=13.5, 5.4 Hz), 2.07 (dm, 1H, J=13.5 Hz), 1.80~1.94 (m, 1H).

EXAMPLE 85

9-Bromo-5-(4-pyridylcarbamoylmethyl)-6,7-dihydro-1H, 5H-pyrido[1,2,3-de]quinoxaline-2,3-dione A procedure similar to that described in Example 51 was carried out with 9-bromo-5-carboxymethyl-6,7-dihydro-1H, 5H-pyrido[1,2,3-de]quinoxaline-2,3-dione (170 mg, 0.5 mmol) and 4-aminopyridine (60 mg, 0.64 mmol) to give 144 mg of the title compound (69%): mp>270° C.; $^1$H NMR (270 MHz, DMSO-d$_6$) δ12.10 (bs, 1H), 10.90 (s, 1H), 9.04 (d, 1H, J=2 Hz), 8.50 (d, 2H, J=5.4 Hz), 8.31 (d, 1H, J=9 Hz), 7.78 (dd, 1H, J=5.4, 9 Hz), 7.24 (d, 1H, J=2 Hz), 7.19 (d, 1H, J=2 Hz), 5.17~5.28 (m, 1H), 3.05 (ddd, 1H, J=17.1, 13.5, 4.5 Hz), 2.83 (dm, 1H, J=17.1 Hz), 2.69 (d, 2H, J=7.2 Hz), 2.13 (dm, 1H, J=13.5 Hz), 1.80~1.96 (m, 1H).

EXAMPLE 86

9-Bromo-5-(O-methyl-N-hydroxycarbamoylmethyl)-6,7-dihydro-1H, 5H-pyrido[1,2,3-de]quinoxaline-2,3-dione A procedure similar to that described in Example 5 was carried out with 9-bromo-5-carboxymethyl-6,7-dihydro-1H, 5H-pyrido[1,2,3-de]quinoxaline-2,3-dione (170 mg, 0.5 mmol) and O-methyl-hydroxylamine hydrochloride (50 mg, 0.60 mmol) to give 170 mg of the title compound (80%): mp 147°~151° C.; ¹H NMR (270 MHz, DMSO-$d_6$) δ12.05 (s, 1H), 11.12 (s, 1H), 7.21 (d, 1H, J=2 Hz), 7.15 (d, 1H, J=2 Hz), 5.03~5.14 (m, 1H), 3.60 (s, 3H), 2.96 (ddd, 1H, J=17.1, 13.5, 4.5 Hz), 2.79 (dm, 1H, J=17.1 Hz), 2.32 (dd, 1H, J=13.5, 5.4 Hz), 2.16 (dd, 1H, J=13.5, 9.9 Hz), 2.03 (dm, 1H, J=13.5 Hz), 1.74~1.93 (m, 1H).

EXAMPLE 87

9-Bromo-5-(2-thiazolylcarbamoylmethyl)-6,7-dihydro-1H, 5H-pyrido[1,2,3-de]quinoxaline- 2,3-dione A procedure similar to that described in Example 51 was carried out with 9-bromo-5-carboxymethyl-6,7-dihydro-1H, 5H-pyrido[1,2,3-de]quinoxaline-2,3-dione (170 mg, 0.5 mmol) and 2-aminothiazole (60 mg, 0.60 mmol) to give 185 mg of the title compound (88%): mp>270° C.; ¹H NMR (270 MHz, DMSO-$d_6$) δ12.20 (s, 1H), 12.07 (s, 1H), 7.47 (d, 2H, J=3.6 Hz), 7.23 (d, 1H, J=3.6 Hz), 7.22 (bs, 1H), 7.17 (bs, 1H), 5.17~5.28 (m, 1H), 3.04 (ddd, 1H, J=17.1, 13.5, 4.5 Hz), 2.64~2.89 (m, 3H), 2.06 (dm, 1H, J=13.5 Hz), 1.81~1.97 (m, 1H).

EXAMPLE 88

9-Bromo-5-(2-cyanoethylcarbamoylmethyl)-6,7-dihydro- 1H, 5H-pyrido[1,2,3-de]quinoxaline-2,3-dione A procedure similar to that described in Example 51 was carried out with 9-bromo-5-carboxymethyl-6,7-dihydro-1H, 5H-pyrido[1,2,3-de]quinoxaline-2,3-dione (300 mg, 0.882 mmol) and 2-aminopropionitrile (80 mg, 1.14 mmol) to give 275 mg of the title compound (80%): mp>270° C.; ¹H NMR (270 MHz, DMSO-$d_6$) δ12.05 (s, 1H), 8.42 (bt, 1H, J=5.6 Hz), 7.21 (d, 1H, J=2 Hz), 7.15 (d, 1H, J=2 Hz), 5.07~5.13 (m, 1H), 3.20~3.29 (m, 2H), 3.01 (ddd, 1H, J=17.1, 13.5, 4.5 Hz), 2.80 (dm, 1H, J=17.1 Hz), 2.55~2.71 (m, 2H), 2.43 (dd, 1H, J=14.4, 5.4 Hz), 2.35 (dd, 1H, J=14.4, 10.8 Hz), 2.04 (dm, 1H, J=13.5 Hz), 1.74~1.89 (m, 1H).

EXAMPLE 89

9-Bromo-5-(5-tetrazolylcarbamoylmethyl)-6,7-dihydro-1H, 5H-pyrido[1,2,3-de]quinoxaline-2,3-dione A procedure similar to that described in Example 51 was carried out with 9-bromo-5-carboxymethyl-6,7-dihydro-1H, 5H-pyrido[1,2,3-de]quinoxaline-2,3-dione (170 mg, 0.5 mmol) and aminotetrazole (50 mg, 0.59 mmol) to give 170 mg of the title compound (84%): mp 246°~247° C.; ¹H NMR (270 MHz, DMSO-$d_6$) δ12.12 (bs, 1H), 12.08 (s, 1H), 7.24 (d, 1H, J=2 Hz), 7.17 (d, 1H, J=2 Hz), 5.19~ 5.28 (m, 1H), 3.01 (ddd, 1H, J=17.1, 13.5, 4.5 Hz), 2.84 (dm, 1H, J=17.1 Hz), 2.66~2.75 (m, 2H), 2.12 (dm, 1H, J=13.5 Hz), 1.83~1.97 (m, 1H).

EXAMPLE 90

9-Bromo-5-(N-hydroxy-phenylcarbamoylmethyl)-6, 7-dihydro-1H, 5H-pyrido[1,2,3-de]quinoxaline-2,3-dione A procedure similar to that described in Example 5 was carried out with 9-bromo-5-carboxymethyl-6,7-dihydro-1H, 5H-pyrido[1,2,3-de]quinoxaline-2,3-dione (150 mg, 0.44 mmol) and N-phenylhydroxylamine (80 mg, 0.73 mmol) to give 50 mg of the title compound (26%) after silica gel column chromatography with 2% acetic acid/ethyl acetate: mp>270° C.; ¹H NMR (270 MHz, DMSO-$d_6$) δ12.04 (s, 1H), 10.01 (s, 1H), 7.56 (d, 2H, J=7.9 Hz), 7.30 (t, 2H, J=7.9 Hz), 7.24 (d, 1H, J=2 Hz), 7.17 (d, 1H, J=2 Hz), 7.05 (t, 1H, J=7.4 Hz), 5.17~5.26 (m, 1H), 3.06 (ddd, 1H, J=17.1, 13.5, 4.5 Hz), 2.83 (dm, 1H, J=17.1 Hz), 2.58~2.62 (m, 2H), 2.09 (dm, 1H, J=13.5 Hz), 1.81~1.95 (m, 1H).

EXAMPLE 91

9-Bromo-5-(p-cyanophenylcarbamoylmethyl)-6,7-dihydro-1H, 5H-pyrido[1,2,3-de]quinoxaline-2,3-dione A procedure similar to that described in Example 52 was carried out with 9-bromo-5-carboxymethyl-6,7-dihydro-1H, 5H-pyrido[1,2,3-de]quinoxaline-2,3-dione (170 mg, 0.5 mmol) and p-cyanoaniline (60 mg, 0.51 mmol) to give 90 mg of the title compound (41%): mp>270° C.; ¹H NMR (270 MHz, DMSO-$d_6$) δ12.06 (s, 1H), 10.44 (s, 1H), 7.77 (d, 2H, J=9.2 Hz), 7.74 (d, 2H, J=9.2 Hz), 7.23 (bs, 1H), 7.17 (bs, 1H), 5.18~5.26 (m, 1H), 3.03 (ddd, 1H, J=17.1, 13.5, 4.5 Hz), 2.83 (dm, 1H, J=17.1Hz), 2.65(d, 2H, J=7.6Hz),2.11 (dm, 1H, J=13.5Hz), 1.83~1.96 (m, 1H).

EXAMPLE 92

9-Bromo-5-(p-carbamoylphenylcarbamoylmethyl)-6, 7-dihydro-1H, 5H-pyrido[1,2,3-de]quinoxaline-2,3-dione A procedure similar to that described in Example 52 was carried out with 9-bromo-5-carboxymethyl-6,7-dihydro-1H, 5H-pyrido[1,2,3-de]quinoxaline-2,3-dione (170 mg, 0.5 mmol) and p-carbamoylaniline (70 mg, 0.51 mmol) to give 130 mg of the title compound (57%): mp>270° C.; ¹H NMR (270 MHz, DMSO-$d_6$) δ12.05 (s, 1H), 10.23 (s, 1H), 7.85 (bs, 1H), 7.83 (d, 2H, J=8.6 Hz), 7.62 (d, 2H, J=8.6 Hz), 7.23 (bm, 2H), 7.17 (bs, 1H), 5.20~5.27 (m, 1H), 3.06 (ddd, 1H, J=17.1, 13.5, 4.5 Hz), 2.84 (dm, 1H, J=17.1 Hz), 2.63 (d, 2H, J=6.9 Hz), 2.12 (dm, 1H, J=13.5 Hz), 1.82~1.96 (m, 1H).

EXAMPLE 93

9-Bromo-5-(p-trifluoromethylphenylcarbamoylmethyl)-6,7-dihydro-1H, 5H-pyrido[1,2,3-de]quinoxaline-2,3-dione A procedure similar to that described in Example 52 was carried out with 9-bromo-5-carboxymethyl-6,7-dihydro-1H, 5H-pyrido[1,2,3-de]quinoxaline-2,3-dione (170 mg, 0.5 mmol) and p-trifluoromethylaniline (83 mg, 0.51 mmol) to give 175 mg of the title compound (73%): mp>270° C.; ¹H NMR (270 MHz, DMSO-$d_6$) δ12.07 (s, 1H), 10.38 (s, 1H), 7.77 (d, 2H, J=8.6 Hz), 7.74 (d, 2H, J=8.6 Hz), 7.24 (bs, 1H), 7.17 (bs, 1H), 5.18~5.27 (m, 1H), 3.06 (ddd, 1H, J=17.1, 13.5, 4.5 Hz), 2.85 (dm, 1H, J=17.1 Hz), 2.65 (d, 2H, J=7.6 Hz), 2.11 (dm, 1H, J=13.5 Hz), 1.82~1.96 (m, 1H).

EXAMPLE 94

9-Bromo-5-(p-acetylaminophenylcarbamoylmethyl)-6,7-dihydro-1H, 5H-pyrido[1,2,3-de]quinoxaline-2,3-dione A procedure similar to that described in Example 5 was carried out with 9-bromo-5-carboxymethyl-6,7-dihydro-1H, 5H-pyrido[1,2,3-de]quinoxaline-2,3-dione (150 mg, 0.44 mmol) and p-acetylaminoaniline (75 mg, 0.5 mmol) to give 190 mg of the title compound (91%): mp>270° C.; $^1$H NMR (270 MHz, DMSO-d$_6$) δ12.06 (s, 1H), 9.94 (s, 1H), 9.87 (s, 1H), 7.44~7.52 (m, 4H), 7.23 (bs, 1H), 7.17 (bs, 1H), 5.18~5.26 (m, 1H), 3.07 (ddd, 1H, J=17.1, 13.5, 4.5 Hz), 2.83 (dm, 1H, J=17.1 Hz), 2.55~2.64 (m, 2H), 2.10 (dm, 1H, J=13.5 Hz), 2.02 (s, 3H), 1.80~1.96 (m, 1H).

EXAMPLE 95

9-Bromo-5-(p-methoxycarbonyl-m-chlorophenylcarbamoylmethyl)-6,7-dihydro-1H, 5H-pyrido[1,2,3-de]quinoxaline-2,3-dione A procedure similar to that described in Example 52 was carried out with 9-bromo-5-carboxymethyl-6,7-dihydro-1H, 5H-pyrido[1,2,3-de]quinoxaline-2,3-dione (340 mg, 1 mmol) and m-chloro-p-methoxycarbonylaniline (200 mg, 1.08 mmol) to give 230 mg of the title compound (45%): mp 167° C. (dec); $^1$H NMR (270 MHz, DMSO-d$_6$) δ12.04 (bs, 1H), 10.48 (s, 1H), 7.89 (d, 1H, J=2 Hz), 7.86 (d, 2H, J=8.6 Hz), 7.53 (dd, 1H, J=8.6, 2 Hz), 7.24 (d, 1H, J=2 Hz), 7.17 (d, 1H, J=2 Hz), 5.17~5.26 (m, 1H), 3.83 (s, 3H), 3.04 (ddd, 1H, J=17.1, 13.5, 4.5 Hz), 2.84 (dm, 1H, J=17.1 Hz), 2.57~2.69 (m, 2H), 2.12 (dm, 1H, J=13.5 Hz), 1.83~1.97 (m, 1H).

EXAMPLE 96

9-Bromo-5-(p-carboxy-m-chlorophenylcarbamoylmethyl)-6,7-dihydro-1H, 5H-pyrido[1,2,3-de]quinoxaline-2,3-dione Hydrolysis of 9-bromo-5-(p-methoxycarbonyl-m-chlorophenylcarbamoylmethyl)-6,7-dihydro-1H, 5H-pyrido[1,2,3-de]quinoxaline-2,3-dione (155 mg, 0.3 retool) was carried out as described in Example 3 to give 145 mg of the title compound (98%): mp 262°~263° C. (dec); $^1$H NMR (270 MHz, DMSO-d$_6$) δ12.08 (s, 1H), 10.42 (s, 1H), 7.86 (d, 1H, J=2 Hz), 7.83 (d, 2H, J=8.6 Hz), 7.50 (dd, 1H, J=8.6, 2 Hz), 7.23 (d, 1H, J=2 Hz), 7.17 (d, 1H, J=2 Hz), 5.17~5.26 (m, 1H), 3.04 (ddd, 1H, J=17.1, 13.5, 4.5 Hz), 2.83 (dm, 1H, J=17.1 Hz), 2.57~2.69 (m, 2H), 2.12 (dm, 1H, J=13.5 Hz), 1.81~1.96 (m, 1H).

EXAMPLE 97

9-Bromo-5-(p-nitrophenylcarbamoylmethyl)-6,7-dihydro-1H, 5H-pyrido[1,2,3-de]quinoxaline-2,3-dione A procedure similar to that described in Example 52 was carried out with 9-bromo-5-carboxymethyl-6,7-dihydro-1H, 5H-pyrido[1,2,3-de]quinoxaline-2,3-dione (170 mg, 0.5 mmol) and p-nitroaniline (70 mg, 0.51 mmol) to give 80 mg of the title compound (35%): mp>270° C.; $^1$H NMR (270 MHz, DMSO-d$_6$) δ12.07 (s, 1H), 10.65 (s, 1H), 8.23 (d, 2H, J=9.2 Hz), 7.30 (d, 2H, J=9.2 Hz), 7.24 (bs, 1H), 7.18 (bs, 1H), 5.20~5.29 (m, 1H), 3.04 (ddd, 1H, J=17.1, 13.5, 4.5 Hz), 2.83 (dm, 1H, J=17.1 Hz), 2.68 (d, 2H, J=7.3 Hz), 2.11 (dm, 1H, J=13.5 Hz), 1.82~1.97 (m, 1H).

EXAMPLE 98

9-Bromo-5-(o-hydroxyphenylcarbamoylmethyl)-6,7-dihydro-1H, 5H-pyrido[1,2,3-de]quinoxaline-2,3-dione A procedure similar to that described in Example 5 was carried out with 9-bromo-5-carboxymethyl-6,7-dihydro-1H, 5H-pyrido[1,2,3-de]quinoxaline-2,3-dione (300 mg, 0.88 mmol) and o-aminophenol (110 mg, 1 mmol) to give 375 mg of the title compound (98%): mp 155° C. (dec); $^1$H NMR (270 MHz, DMSO-d$_6$) δ12.07 (s, 1H), 9.71 (bs, 1H), 9.36 (s, 1H), 7.72 (d, 1H, J=7.2 Hz), 7.24 (bs, 1H), 7.17 (bs, 1H), 6.95 (dt, 1H, J=2, 7.2 Hz), 6.85 (dd, 1H, J=2, 7.2 Hz), 6.76 (dt, 1H, J=7.2, 2 Hz), 5.17~5.26 (m, 1H), 3.14 (ddd, 1H, J=17.1, 13.5, 4.5 Hz), 2.80 (dm, 1H, J=17.1 Hz), 2.78 (dd, 1H, J=14.4, 9 Hz), 2.64 (dd, 1H, J=14.4, 4.5 Hz), 2.10 (dm, 1H, J=13.5 Hz), 1.78~1.92 (m, 1H).

EXAMPLE 99

9-Bromo-5-(o-aminophenylcarbamoylmethyl)-6,7-dihydro-1H, 5H-pyrido[1,2,3-de]quinoxaline-2,3-dione A procedure similar to that described in Example 5 was carried out with 9-bromo-5-carboxymethyl-6,7-dihydro-1H, 5H-pyrido[1,2,3-de]quinoxaline-2,3-dione (300 mg, 0.88 mmol) and o-phenylenediamine (110 mg, 1 mmol) to give 370 mg of the title compound (98%): mp>270° C.; $^1$H NMR (270 MHz, DMSO-d$_6$) δ12.07 (s, 1H), 9.23 (s, 1H), 7.25 (d, 1H, J=2 Hz), 7.17 (d, 1H, J=2 Hz), 7.13 (dd, 1H, J=8.1 Hz), 6.91 (dt, 1H, J=2, 8.1 Hz), 6.72 (dd, 1H, J=2, 8.1 Hz), 6.54 (dt, 1H, J=8.1, 2 Hz), 5.19~5.27 (m, 1H), 4.85 (br, 2H), 3.10 (ddd, 1H, J=17.1, 13.5, 4.5 Hz), 2.85 (dm, 1H, J=17.1 Hz), 2.61 (d, 2H, J=7.3 Hz), 2.12 (dm, 1H, J=13.5 Hz), 1.81~1.95 (m, 1H).

EXAMPLE 100

9-Bromo-5-(p-methoxycarbonylmethylphenylcarbamoylmethyl)-6,7-dihydro-1H, 5H-pyrido[1,2,3-de]quinoxaline-2,3-dione A procedure similar to that described in Example 52 was carried out with 9-bromo-5-carboxymethyl-6,7-dihydro-1H, 5H-pyrido[1,2,3-de]quinoxaline-2,3-dione (340 mg, 1 mmol) and p-methoxycarbonylmethylaniline (215 mg, 1.3 mmol) to give 395 mg of the title compound (81%): mp 262° C. (dec); $^1$H NMR (270 MHz, DMSO-d$_6$) δ10.02 (s, 1H), 7.50 (d, 2H, J=8.3 Hz), 7.23 (bs, 1H), 7.18 (d, 2H, J=8.3 Hz), 7.17 (bs, 1H), 5.17~5.26 (m, 1H), 3.61~3.62 (m, 5H), 3.06 (ddd, 1H, J=17.1, 13.5, 4.5 Hz), 2.84 (dm, 1H, J=17.1 Hz), 2.56~2.66 (m, 2H), 2.11 (dm, 1H, J=13.5 Hz), 1.76~1.94 (m, 1H).

EXAMPLE 101

9-Bromo-5-(p-carboxymethylphenylcarbamoylmethyl)-6,7-dihydro-1H, 5H-pyrido[1,2,3-de]quinoxaline-2,3-dione Hydrolysis of 9-bromo-5-(p-methoxycarbonylmethylphenylcarbamoylmethyl)-6,7-dihydro-1H, 5H-pyrido[1,2,3-de]quinoxaline-2,3-dione (250 mg, 0.5 mmol) was carried out as described in Example 3 to give 230 mg of the title compound (97%): mp>270° C.; $^1$H NMR (270 MHz, DMSO-d$_6$) δ12.27 (s, 1H), 12.06 (s, 1H), 9.99 (s, 1H), 7.49 (d, 2H, J=8.3 Hz), 7.24 (bs, 1H), 7.17 (bs, 1H), 7.16 (d, 2H, J=8.3 Hz), 5.17~5.27 (m, 1H), 3.51 (s, 2H), 3.07 (ddd, 1H, J=17.1, 13.5, 4.5 Hz), 2.83 (dm, 1H, J=17.1 Hz), 2.56~2.68 (m, 2H), 2.09 (dm, 1H, J=13.5 Hz), 1.80~1.94 (m, 1H).

EXAMPLE 102 trans-9-Bromo-6-methyl-5-(p-sulfamoylphenylcarbamoylmethyl)-6,7-dihydro-1H, 5H-pyrido[1,2,3-de]quinoxaline-2,3-dione A procedure similar to that described in Example 52 was carried out with trans-9-bromo-5-carboxymethyl-6-methyl-6,7-dihydro-1H, 5H-pyrido[1,2,3-de]quinoxaline-2,3-dione (50 mg, 0.14 mmol) and p-sulfamoylaniline (25 mg, 0.15 mmol) to give 42 mg of the title compound (58%) after recrystallization from acetone-methanol-water: mp 279.5°~295° C. (dec); $^1$H NMR (270 MHz, DMSO-$d_6$) δ12.09 (s, 1H), 10.32 (s, 1H), 7.76 (d, 2H, J=8.9 Hz), 7.70 (d, 2H, J=8.9 Hz), 7.23 (s, 2H), 7.21 (s, 1H), 7.18 (s, 1H), 4.95~5.05 (m, 1H), 3.21 (dd, 1H, J=17.8, 5.9 Hz), 2.52~2.66 (m, 3H), 2.28~2.42 (m, 1H), 0.87 (d, 3H, J=6.9 Hz).

EXAMPLE 103 trans-9-Bromo-5-(p-ethoxycarbonylphenylcarbamoylmethyl)-6-methyl-6,7-dihydro-1H, 5H-pyrido[1,2,3-de]quinoxaline-2,3-dione A procedure similar to that described in Example 52 was carried out with trans-9-bromo-5-carboxymethyl-6-methyl-6,7-dihydro-1H, 5H-pyrido[1,2,3-de]quinoxaline-2,3-dione (50 mg, 0.14 mmol) and p-ethoxycarbonylaniline (24 mg, 0.15 mmol) to give 58 mg of the title compound (82%): mp 282°~292° C.; $^1$H NMR (270 MHz, DMSO-$d_6$) δ12.09 (s, 1H), 10.33 (s, 1H), 7.90 (d, 2H, J=8.6 Hz), 7.70 (d, 2H, J=8.6 Hz), 7.21 (s, 1H), 7.18 (s, 1H), 4.92~5.02 (m, 1H), 4.28 (q, 2H, J =6.9 Hz), 3.20 (dd, 1H, J=17.8, 5.9 Hz), 2.52~2.66 (m, 3H), 2.28~2.42 (m, 1H), 1.32 (t, 3H, J=6.9 Hz), 0.87 (d, 3H, J=6.9 Hz).

EXAMPLE 104 trans-9-Bromo-5-(p-carboxyphenylcarbamoylmethyl)-6-methyl-6,7-dihydro-1H, 5H-pyrido[1,2,3-de]quinoxaline-2,3-dione Hydrolysis of trans-9-bromo-5-(p-ethoxycarbonylphenylcarbamoylmethyl)-6-methyl-6,7-dihydro-1H, 5H-pyrido[1,2,3-de]quinoxaline-2,3-dione (40 mg, 0.08 mmol) was carried out as described in Example 3 to give 30 mg of the title compound (79%): mp 280°~284° C.; $^1$H NMR (270 MHz, DMSO-$d_6$) δ12.08 (s, 1H), 10.29 (s, 1H), 7.88 (d, 2H, J=8.6 Hz), 7.67 (d, 2H, J=8.6 Hz), 7.22 (s, 1H), 7.18 (s, 1H), 4.92~5.02 (m, 1H), 4.28 (q, 2H, J=6.9 Hz), 3.24 (dd, 1H, J=17.8, 5.9 Hz), 2.65~2.70 (m, 3H), 2.28~2.42 (m, 1H), 1.32 (t, 3H, J=6.9 Hz), 0.87 (d, 3H, J=6.9 Hz).

EXAMPLE 105 trans-9-Bromo-5-(o-ethoxycarbonylphenylcarbamoylmethyl)-6-methyl-6,7-dihydro-1H, 5H-pyrido[1,2,3-de]quinoxaline-2,3-dione A procedure similar to that described in Example 52 was carried out with trans-9-bromo-5-carboxymethyl-6-methyl-6,7-dihydro- 1H, 5 H-pyrido[1,2,3-de]quinoxaline-2,3-dione (300 mg, 0,849 mmol) and o-ethoxycarbonylaniline (147 mg, 0.891 mmol) to give 153 mg of the title compound (36%): mp 238°~248° C.; $^1$H NMR (270 MHz, DMSO-$d_6$) δ11.39 (s, 1H), 11.31 (s, 1H), 8.66 (d, 2H, J=8.4 Hz), 8.04 (dd, 1H, J=8.4, 1.7 Hz), 7.55 (td, 1H, J=8.4, 1.7 Hz), 7.35 (d, 1H, J=1.9 Hz), 7.19 (d, 1H, J=1.9 Hz), 7.11 (td, 1H, J=8.4, 1.7 Hz), 5.19~5.29 (m, 1H), 4.37 (q, 2H, J=7.3 Hz), 3.29 (dd, 1H, J=17.0, 5.1 Hz), 2.97 (dd, 1H, J=14.5, 4.6 Hz), 2.55~2.70 (m, 3H), 1.40 (t, 3H, J=7.3 Hz), 0.88 (d, 3H, J=6.9 Hz).

EXAMPLE 106 trans-9-Bromo-5-(o-carboxyphenylcarbamoylmethyl)-6-methyl-6,7-dihydro-1H, 5H-pyrido[1,2,3-de]quinoxaline-2,3-dione Hydrolysis of trans-9-bromo-5-(o-ethoxycarbonylphenylcarbamoylmethyl)-6-methyl-6,7-dihydro-1H, 5H-pyrido[1,2,3-de]quinoxaline-2,3-dione (110 mg, 0.22 mmol) was carried out as described in Example 3 to give 86 mg of the title compound (83%): mp 274°~275° C. (dec); $^1$H NMR (270 MHz, DMSO-$d_6$) δ12.06 (s, 1H), 11.09 (s, 1H), 8.38 (d, 2H, J=8.4 Hz), 7.95 (dd, 1H, J=8.4, 1.7 Hz), 7.58 (td, 1H, J=8.4, 1.7 Hz), 7.19 (s, 1H), 7.17 (s, 1H), 7.16 (td, 1H, J=8.4, 1.7 Hz), 4.90~5.00 (m, 1H), 3.24 (dd, 1H, J=17.0, 5.1 Hz), 2.72 (dd, 1H, J=14.9, 5.3 Hz), 2.57~2.65 (m, 2H), 2.35~2.50 (m, 1H), 0.88 (d, 3H, J=6.9 Hz).

EXAMPLE 107

9-Bromo-5-methoxycarbonylmethyl-5-methyl-6,7-dihydro-1H, 5H-pyrido[1,2,3-de]quinoxaline-2,3-dione 1) N-Trifluoroacetyl-2-methoxycarbonyltetrahydroquinoline To a solution of 2-methoxycarbonyltetrahydroquinoline (7.3 g, 32.1 mmol) in dichloromethane (100 mL) in the presence of triethylamine (12 mL) and a small amount of 4-dimethylaminopyridine was added slowly trifluoroacetic anhydride (4.88 mL, 35.3 mmol) at 0° C. The mixture was stirred for 6 h at room temperature and the 1N aqueous hydrochloric acid was added. The organic layer was separated, washed with water, dried over magnesium sulfate, and concentrated. The residue was purified by silica gel column chromatography with 15:1 to 5:1 hexane/ethyl acetate to give 8.80 g of N-trifluoroacetyl-2-methoxycarbonyltetrahydroquinoline (96%): $^1$H NMR (270 MHz, CDCl$_3$) δ7.23 (m, 4H), 5.15 (m, 1H), 3.69 (s, 3H), 2.63~2.76 (m, 3H), 1.75 (m, 1H).

2) 2-Methyl-N-trifluoroacetyl-2-methoxycarbonyltetrahydroquinoline

To a solution of N-trifluoroacetyl-2-methoxycarbonyltetrahydroquinoline (8.7 g, 30.3 mmol)in THF (100 mL) was added slowly 0.5N potassium hexamethylsilazide in toluene (66.6 mL, 33.3 mmol) over 15 min at −78° C. The mixture was stirred for 10 min followed by addition of iodomethane (2.3 mL, 36.4 mmol) at the same temperature. The mixture was allowed to warm to room temperature, stirred 5 h, poured into water, and extracted with ethyl acetate. The extract was washed with water and brine, dried over magnesium sulfate, and concentrated to give 8.98 g of 2-methyl-N-trifluoroacetyl-2-methoxycarbonyltetrahydroquinoline (98%): $^1$H NMR (270 MHz, CDCl$_3$) δ7.18 (m, 3H), 7.07 (m, 1H), 3.71 (s, 3H), 2.90 (td, 1H, J=13.9, 3.3 Hz), 2.50 (dt, 1H, J=13.9, 3.3 Hz), 2.28 (dt, 1H, J=13.9, 3.3 Hz), 1.56 (s, 3H), 1.53 (td, 1H, J=13.9, 3.3 Hz).

2-Hydroxymethyl-2-methyltetrahydroquinoline

To a suspension of lithium aluminum hydride (1.12 g, 29.5 mmol) in THF (10 mL) was added dropwise 2-methyl-N-trifluoroacetyl-2-methoxycarbonyltetrahydroquinoline (8.88 g, 29.5 mmol) in THF (90 mL) over 25 min, while the reaction temperature was maintained at 40°–45° C. The mixture was heated at 60° C. for 1 h and the excess reagent was decomposed by slow addition of aqueous THF at 0° C. Aqueous sodium hydroxide was added and stirred for 30 min followed by addition of diethyl ether. The organic layer was separated, washed with brine three times, dried over magnesium sulfate, and concentrated. The residue was purified by silica gel column chromatography with 3:1 hexane/ethyl acetate to give 4.97 g of 2-hydroxymethyl-2-methyltetrahydroquinoline (95%): $^1$H NMR (270 MHz, CDCl$_3$) δ6.98 (m, 2H), 6.64 (td, 1H, J=7.3, 1 Hz), 3.73 (bs, 1H), 3.47 (s, 2H), 2.76 (m, 2H), 1.93 (bs, 1H), 1.86 (m, 1H), 1.61 (m, 1H), 1.19 (s, 3H).

4) 9-Bromo-5-methoxycarbonylmethyl-5-methyl-6,7-dihydro-1H, 5H-pyrido-1,2,3-de]quinoxaline-2,3-dione The title compound was prepared by the route outlined in Example 22-2 to 6 starting with 2-hydroxymethyl-2-methyltetrahydroquinoline. In nitration step of Example 22-6, conditions of nitronium tetrafluoroborate in dichloromethane at room temperature were employed instead of those of refluxing ammonium nitrate-trifluoroacetic anhydride in chloroform: mp 254.5°–257.5° C.; $^1$H NMR (270 MHz, DMSO-d$_6$) δ12.02 (bs, 1H), 7.15 (s, 2H), 3.64 (d, 1H, J=15.8 Hz), 3.50 (s, 3H), 2.94 (d, 1H, J=15.8 Hz), 2.77–2.87 (m, 2H), 2.03–2.19 (m, 1H), 1.84–200 (m, 1H), 1.62 (s, 3H).

EXAMPLE 108

9-Bromo-5-carboxymethyl-5-methyl-6,7-dihydro-1H, 5H-pyrido[1,2,3-de]quinoxaline-2,3-dione Hydrolysis of 9-bromo-5-methoxycarbonylmethyl-5-methyl-6,7-dihydro-1H, 5H-pyrido[1,2,3-de]quinoxaline-2,3-dione (800 mg, 2.26 mmol) was carried out as described in Example 3 to give 706 mg of the title compound (92%): mp 298° C. (dec); $^1$H NMR (270 MHz, DMSO-d$_6$) δ12.13 (bs, 1H), 12.01 (s, 1H), 7.14 (bs, 2H), 3.61 (d, 1H, J=16 Hz), 2.74–2.84 (m, 2H), 2.80 (d, 1H, J=16 Hz), 2.12–2.28 (m, 1H), 1.84–2.00 (m, 1H), 1.60 (s, 3H).

EXAMPLE 109

9-Bromo-5-methyl-5-phenylcarbamoylmethyl-6,7-dihydro-1H, 5H-pyrido[1,2,3-de]quinoxaline-2,3-dione A procedure similar to that described in Example 52 was carried out with 9-bromo-5-carboxymethyl-5-methyl-6,7-dihydro-1H, 5H-pyrido[1,2,3-de]quinoxaline-2,3-dione (100 mg, 0.28 mmol) and aniline (28 μL, 0.31 mmol) to give 89 mg of the title compound (73%): mp 155°–162° C. (dec); $^1$H NMR (270 MHz, DMSO-d$_6$) δ812.00 (s, 1H), 9.92 (s, 1H), 7.46 (d, 2H, J=8 Hz), 7.23 (t, 2H, J=8 Hz), 7.14 (bs, 2H), 6.99 (t, 1H, J=8 Hz), 3.63 (d, 1H, J=15 Hz), 2.90 (d, 1H, J=15 Hz), 2.80–2.90 (m, 2H), 2.25–2.40 (m, 1H), 1.85–2.00 (m, 1H), 1.68 (s, 3H).

EXAMPLE 110

9-Bromo-5-(p-aminophenylcarbamoylmethyl)-6,7-dihydro-1H, 5H-pyrido[1,2,3-de]quinoxaline-2,3-dione A procedure similar to that described in Example 5 was carried out with 9-bromo-5-carboxymethyl-6,7-dihydro-1H, 5H-pyrido[1,2,3-de]quinoxaline-2,3-dione (150 mg, 0.44 mmol) and p-phenylenediamine (540 mg, 5 mmol) to give 115 mg of the title compound (61%): mp>270° C.; $^1$H NMR (270 MHz, DMSO-d$_6$) δ12.11 (s, 1H), 10.32 (s, 1H), 9.93 (br, 2H), 7.67 (d, 1H, J=8.9 Hz), 7.29 (d, 2H, J=8.6 Hz), 7.50 (dd, 2H, J=8.6 Hz), 7.23 (bs, 1H), 7.20 (bs, 1H), 5.18–5.27 (m, 1H), 3.08 (ddd, 1H, J=17.1, 13.5, 4.5 Hz), 2.83 (dm, 1H, J=17.1 Hz), 2.56–2.70 (m, 2H), 2.08 (dm, 1H, J=13.5 Hz), 1.82–1.96 (m, 1H).

EXAMPLE 111

9-Bromo-5-(p-1-methoxycarbonylethylphenylcarbamoylmethyl)-6,7-dihydro-1H, 5H-pyrido[1,2,3-de]quinoxaline-2,3-dione A procedure similar to that described in Example 52 was carried out with 9-bromo-5-carboxymethyl-6,7-dihydro-1H, 5H-pyrido[1,2,3-de]quinoxaline-2,3-dione (340 mg, 1 mmol) and p-1-methoxycarbonylethylphenylaniline (200 mg, 1.1 mmol) to give 415 mg of the title compound (83%): mp 252°–253° C. (dec); $^1$H NMR (270 MHz, DMSO-d$_6$) δ12.06 (s, 1H), 10.02 (s, 1H), 7.51 (d, 2H, J=8.6 Hz), 7.24 (bs, 1H), 7.21 (d, 2H, J=8.6 Hz), 7.17 (bs, 1H), 5.17–5.26 (m, 1H), 3.75 (q, 1H, J=7 Hz), 3.58 (s, 3H), 3.06 (ddd, 1H, J=17.1, 13.5, 4.5 Hz), 2.83 (dm, 1H, J=17.1 Hz), 2.56–2.68 (m, 2H), 2.09 (dm, 1H, J=13.5 Hz), 1.81–1.94 (m, 1H), 1.37 (d, 3H, J=7 Hz).

EXAMPLE 112

9-Bromo-5-(p-1-carboxyethylphenylcarbamoylmethyl)-6,7-dihydro-1H, 5H-pyrido[1,2,3-de]quinoxaline-2,3-dione Hydrolysis of 9-bromo-5-(p-1-methoxycarbonylethylphenylcarbamoylmethyl)-6,7-dihydro-1H, 5H-pyrido[1,2,3-de]quinoxaline-2,3-dione (250 mg, 0.5 mmol) was carried out as described in Example 3 to give 245 mg of the title compound (quant): mp>270° C.; $^1$H NMR (270 MHz, DMSO-d$_6$) δ12.24 (bs, 1H), 12.06 (s, 1H), 10.00 (s, 1H), 7.50 (d, 2H, J=8.6 Hz), 7.17–7.23 (m, 4H), 5.17–5.26 (m, 1H), 3.61 (q, 1H, J=7 Hz), 3.06 (ddd, 1H, J=17.1, 13.5, 4.5 Hz), 2.83 (dm, 1H, J=17.1 Hz), 2.56–2.66 (m, 2H), 2.08 (dm, 1H, J=13.5 Hz), 1.82–1.96 (m, 1H), 1.34 (d, 3H, J=7 Hz).

EXAMPLE 113

9-Bromo-5-(1-methoxycarbonylethyl)-6,7-dihydro-1H, 5H-pyrido[1,2,3-de]quinoxaline-2,3-dione (less polar)

1) 2-Ethoxycarbonylmethylcarbonylquinoline

A mixture of ethyl quinaldinate (58.0 g, 0.288 mol), ethyl acetate (42.6 mL, 0.432 mol), and sodium ethoxide (29.4 g, 0.432 mol) in toluene (1 L) was heated at reflux temperature for 2 h. The mixture was neutralized by addition of diluted hydrochloric acid and extracted with ethyl acetate. The organic layer was washed with water and brine, dried over magnesium sulfate, and concentrated. The residue was purified with silica gel column chromatography with 15:1 to 3:1 hexane/ethyl acetate to give 32.34 g of 2-ethoxycarbonylmethylcarbonylquinoline (46%): $^1$H NMR (270 MHz, CDCl$_3$) δ8.28 (d, 1H, J=8.3 Hz), 8.17 (dd, 1H, J=8.2, 1 Hz), 8.14 (d, 1H, J=8.3 Hz), 7.84 (dd, 1H, J=8.2, 1 Hz), 7.79 (td, 1H, J=8.2, 1 Hz), 7.66 (td, 1H, J=8.2, 1 Hz), 4.36 (s, 2H), 4.22 (q, 2H, J=7.3 Hz), 1.24 (t, 3H, J=7.3 Hz).

2-Acetylquinoline

A solution of 2-ethoxalylmethylcarbonylquinoline (32.24 g, 0.132 mol) in concentrated hydrochloric acid (300 mL) was refluxed for 4 h and concentrated in vacuo. The residue was dissolved in aqueous sodium bicarbonate and extracted with ethyl acetate. The extract was washed with water and brine, dried over magnesium sulfate, and concentrated. The residue was purified by silica gel column chromatography with 20:1 to 7:1 hexane/ethyl acetate to give 21.72 g of 2-acetylquinoline (96%): $^1$H NMR (270 MHz, CDCl$_3$) δ8.25 (d, 1H, J=8.6 Hz), 8.19 (dd, 1H, J=8.3, 1 Hz), 8.13 (d, 1H, J=8.6 Hz), 7.86 (dd, 1H, J=8.3, 1 Hz), 7.78 (td, 1H, J=8.3, 1 Hz), 7.64 (td, 1H, J=8.3, 1 Hz), 2.87 (s, 3H).

3) 2-(1-Hydroxyethyl)tetrahydroquinoline

2-Acetylquinoline (21.0 g, 0.123 mol) in acetic acid (210 mL) was hydrogenated over platinum oxide (1.0 g) under atmospheric pressure of hydrogen at room temperature until the theoretical amount of hydrogen was consumed. The mixture was passed through celite and concentrated. The residue was purified by column chromatography with 5:1 to 1:1 hexane/ethyl acetate to give 16.85 g of 2-(1-hydroxyethyl)tetrahydroquinoline (78%): $^1$H NMR (270 MHz, CDCl$_3$) δ6.95 (m, 2H), 6.62 (td, 1H, J=7.3, 1 Hz), 6.51 (dd, 1H, J=7.3, 1 Hz), 3.81 (dq, 1H, J=10.2, 6.6 Hz), 1.87 (m, 1H), 1.76 (m, 1H), 1.20 (d, 3H, J=6.6 Hz).

4) 6-Bromo-N-ethoxalyl-2-(1-methoxycarbonylethyl)tetrahydroquinoline

The title compound was prepared by the route outlined in Example 22-2 to 5 starting with 2-(1-hydroxyethyl)tetrahydroquinoline. The diastereomixture (14.1 g) obtained was separated by silica gel column chromatography with 5:1 hexane/ethyl acetate to give 8.92 g of a less polar product (67%) and 3.29 g of a more polar product (25%); less polar: $^1$H NMR (270 MHz, CDCl$_3$) δ7.35 (s, 1H), 7.29 (d, 1H, J=8.3 hz), 6.89 (d, 1H, J=8.3 Hz), 4.87 (dd, 1H, J=14.9, 7.3 Hz), 4.14 (q, 2H, J=7.3 Hz), 3.57 (s, 3H), 2.71 (m, 3H), 3.34 (m, 1H), 1.73 (m, 1H), 1.16 (d, 3H, J=6.9 Hz), 1.14 (t, 3H, J=7.3 Hz); more polar: $^1$H NMR (270 MHz, CDCl$_3$) δ7.35 (s, 1H), 7.31 (d, 1H, J=8.3 Hz), 6.94 (d, 1H, J=8.3 Hz), 4.33 (dd, 1H, J=14.9, 7.3 Hz), 4.11 (q, 2H, J=7.3 Hz), 3.68 (s, 3H), 2.93 (m, 1H), 2.65 (m, 2H), 2.31 (m, 1H), 1.12 (t, 3H, J=7.3 Hz), 1.03 (d, 3H, J=7.3 Hz).

5) 9-Bromo-5-(1-methoxycarbonylethyl)-6,7-dihydro-1H, 5H-pyrido[1,2,3-de]quinoxaline-2,3-dione (less polar)

The title compound was prepared by the route outlined in Example 22-6 to 7 starting with 6-bromo-N-ethoxalyl-2-(1-methoxycarbonylethyl)tetrahydroquinoline (less polar). In nitration step of Example 22-6, conditions of nitronium tetrafluoroborate in dichloromethane at room temperature were employed instead of those of refluxing ammonium nitrate-trifluoroacetic anhydride in chloroform: mp 242° C.; $^1$H NMR (270 MHz, DMSO-d$_6$) δ12.08 (s, 1H), 7.21 (s, 1H), 7.17 (s, 1H), 4.93 (bd, 1H, J=10 Hz), 3.40 (s, 3H), 2.89 (ddd, 1H, J=17.1, 13.5, 4.5 Hz), 2.80 (dm, 1H, J=17.1 Hz), 2.60 (qd, 1H, J=7, 10 Hz), 2.23 (dm, 1H, J=13.5 Hz), 1.72~1.91 (m, 1H), 1.11 (d, 3H, J=7 Hz).

EXAMPLE 114

9-Bromo-5-(1-methoxycarbonylethyl)-6,7-dihydro-1H, 5H-pyrido[1,2,3-de]quinoxaline-2,3-dione (more polar)

The title compound was prepared by the route outlined in Example 22-6 to 7 starting with 6-bromo-N-ethoxalyl-2-(1-methoxycarbonylethyl)tetrahydroquinoline (more polar). In nitration step of Example 22-6, conditions of nitronium tetrafluoroborate in dichloromethane at room temperature were employed instead of those of refluxing ammonium nitrate-trifluoroacetic anhydride in chloroform: mp 256°~257° C.; $^1$H NMR (270 MHz, DMSO-d$_6$) δ12.12 (s, 1H), 7.19 (s, 1H), 7.16 (s, 1H), 5.11 (bd, 1H, J=9 Hz), 3.58 (s, 3H), 2.89 (ddd, 1H, J=17.1, 13.5, 4.5 Hz), 2.72~2.87 (m, 2H), 2.03 (dm, 1H, J=13.5 Hz), 1.76~1.94 (m, 1H), 0.97 (d, 3H, J=7 Hz).

EXAMPLE 115

9-Bromo-5-(1-carboxyethyl)-6,7-dihydro-1H, 5H-pyrido[1,2,3-de]quinoxaline-2,3-dione (less polar)

Hydrolysis of 9-bromo-5-(1-methoxycarbonylethyl)-6,7-dihydro-1H, 5H-pyrido[1,2,3-de]quinoxaline-2,3-dione (less polar) (2.0 g, 5.45 mmol) was carried out as described in Example 3 to give 1.96 g of the title compound (quant): mp>300° C.; $^1$H NMR (270 MHz, DMSO-d$_6$) δ12.59 (bs, 1H), 12.10 (s, 1H), 7.20 (s, 1H), 7.16 (s, 1H), 5.11 (bd, 1H, J=10 Hz), 2.97 (ddd, 1H, J=17.1, 13.5, 4.5 Hz), 2.80 (dm, 1H, J=17.1 Hz), 2.64 (qd, 1H, J=7, 10 Hz), 2.09 (dm, 1H, J=13.5 Hz), 1.76~1.96 (m, 1H), 0.95 (d, 3H, J=7 Hz).

EXAMPLE 116

9-Bromo-5-(1-carboxyethyl)-6,7-dihydro-1H, 5H-pyrido[1,2,3-de]quinoxaline-2,3-dione (more polar)

Hydrolysis of 9-bromo-5-(1-methoxycarbonylethyl)-6,7-dihydro-1H, 5H-pyrido[1,2,3-de]quinoxaline-2,3-dione (more polar) (0.7 g, 1.91 mmol) was carried out as described in Example 3 to give 588 mg of the title compound (87%): mp 281.5°~287° C.; $^1$H NMR (270 MHz, DMSO-d$_6$) δ12.25 (bs, 1H), 12.04 (s, 1H), 7.19 (s, 1H), 7.16 (s, 1H), 4.98 (bd, 1H, J=10 Hz), 2.90 (ddd, 1H, J=17.1, 13.5, 4.5 Hz), 2.88 (dm, 1H, J=17.1 Hz), 2.51 (qd, 1H, J=7, 10 Hz), 2.24 (dm, 1H, J=13.5 Hz), 1.73~1.93 (m, 1H), 1.07 (d, 3H, J=7 Hz).

EXAMPLE 117

9-Bromo-5-(1-phenylcarbamoylethyl)-6,7-dihydro-1H, 5H-pyrido[1,2,3-de]quinoxaline-2,3-dione (less polar)

A procedure similar to that described in Example 52 was carried out with 9-bromo-5-(1-carboxyethyl)-6,7-dihydro-1H, 5H-pyrido[1,2,3-de]quinoxaline-2,3-dione (less polar) (100 mg, 0.28 mmol) and aniline (28 µL, 0.31 mmol) to give 70 mg of the title compound (58%): mp>300° C.; $^1$H NMR (270 MHz, DMSO-d$_6$) δ12.07 (s, 1H), 10.00 (s, 1H), 7.52 (d, 2H, J=8 Hz), 7.29 (t, 1H, J=8 Hz), 7.19 (s, 1H), 7.17 (s, 1H), 7.05 (t, 1H, J=8 Hz), 5.19 (bd, 1H, J=9 Hz), 3.10 (ddd, 1H, J=17.1, 13.5, 4.5 Hz), 2.67~2.84 (m, 2H, J=17.1 Hz), 2.01 (dm, 1H, J=13.5 Hz), 1.72~1.92 (m, 1H), 1.02 (d, 3H, J=7 Hz).

EXAMPLE 118

9-Bromo-5-(1-phenylcarbamoylethyl)-6,7-dihydro-1H, 5H-pyrido[1,2,3-de]quinoxaline- 2,3-dione (more polar)

A procedure similar to that described in Example 52 was carried out with 9-bromo-5-(1-carboxyethyl)-6,7-dihydro-1H, 5H-pyrido[1,2,3-de]quinoxaline-2,3-dione (more polar) (100 mg, 0.28 mmol) and aniline (28 µL, 0.31 mmol) to give 50 mg of the title compound (41%): mp>300° C.; $^1$H NMR (270 MHz, DMSO-$d_6$) δ11.92 (s, 1H), 9.46 (s, 1H), 7.32 (d, 2H, J=8 Hz), 7.23 (t, 1H, J=8 Hz), 7.21 (s, 1H), 7.19 (s, 1H), 6.99 (t, 1H, J=8 Hz), 5.13 (bd, 1H, J=9 Hz), 2.73~2.99 (m, 2H), 2.59 (qd, 1H, J=9, 7 Hz), 2.28 (dm, 1H, J=13.5 Hz), 1.72~1.92 (m, 1H), 1.13 (d, 3H, J=7 Hz).

EXAMPLE 119

9-Bromo-5-(2-benzimidazolylmethyl)-6,7-dihydro-1H, 5H-pyrido[1,2,3-de]quinoxaline-2,3-dione hydrochloride A solution of 9-bromo-5-(o-aminophenylcarbamoylmethyl)-6,7-dihydro-1H, 5H-pyrido[1,2,3-de]quinoxaline-2,3-dione (Example 99) (250 mg, 0.5 mmol) in a mixture of acetonitrile (10 mL) and concentrated hydrochloric acid (2 mL) was heated at 50° C. for 5 h and concentrated. The residue was washed with distilled water and diethyl ether and dried in vacuo to give 150 mg of the title compound (73%): mp>270° C.; $^1$H NMR (270 MHz, DMSO-$d_6$) δ12.15 (s, 1H), 7.80 (dd, 2H, J=6.3, 3 Hz), 7.54 (dd, 2H, J=6.3, 3 Hz), 7.28 (bs, 1H), 7.25 (bs, 1H), 5.26~5.35 (m, 1H), 3.41~3.50 (m, 2H), 3.07 (ddd, 1H, J=17.1, 13.5, 4.5 Hz), 2.90 (dm, 1H, J=17.1 Hz), 2.19 (dm, 1H, J=13.5 Hz), 1.90~2.05 (m, 1H).

EXAMPLE 120

9-Bromo-5-(p-tolylcarbamoylmethyl)-6,7-dihydro-1H, 5H-pyrido[1,2,3-de]quinoxaline-2,3-dione A procedure similar to that described in Example 5 was carried out with 9-bromo-5-carboxymethyl-6,7-dihydro-1H, 5H-pyrido[1,2,3-de]quinoxaline-2,3-dione (150 mg, 0.44 mmol) and p-methylaniline (107 mg, 1 mmol) to give 180 mg of the title compound (95%): mp>270° C.; $^1$H NMR (270 MHz, DMSO-$d_6$) δ12.06 (s, 1H), 9.91 (s, 1H), 7.44 (d, 2H, J=8.6 Hz), 7.23 (bs, 1H), 7.17 (bs, 1H), 7.10 (d, 2H, J=8.6 Hz), 5.16~5.26 (m, 1H), 3.07 (ddd, 1H, J=17.1, 13.5, 4.5 Hz), 2.83 (dm, 1H, J=17.1 Hz), 2.55~2.66 (m, 2H), 2.26 (s, 3H), 2.09 (dm, 1H, J=13.5 Hz), 1.80~1.94 (m, 1H).

EXAMPLE 121

9-Bromo-5-[(o-methoxycarbonylmethylphenyl)carbamoylmethyl]-6,7-dihydro-1H, 5H-pyrido[1,2,3-de]quinoxaline-2,3-dione A procedure similar to that described in Example 52 was carried out with 9-bromo-5-carboxymethyl-6,7-dihydro-1H, 5 H-pyrido[1,2,3-de]quinoxaline-2,3-dione (340 mg, 1 mmol) and o-methoxycarbonylmethylaniline (180 mg, 1 mmol) to give 340 mg of the title compound (70%): mp 206°~207° C. (dec); $^1$H NMR (270 MHz, DMSO-$d_6$) δ12.06 (bs, 1H), 9.51 (s, 1H), 7.36 (bd, 1H, J=8.6 Hz), 7.26~7.29 (m, 3H), 7.16~7.19 (m, 2H), 5.16~5.25 (m, 1H), 3.70 (s, 2H), 3.59 (s, 3H), 3.07 (ddd, 1H, J=17.1, 13.5, 4.5 Hz), 2.83 (dm, 1H, J=17.1 Hz), 2.60 (d, 2H, J=7.6 Hz), 2.11 (dm, 1H, J=13.5 Hz), 1.80~1.96 (m, 1H).

EXAMPLE 122

9-Bromo-5-[(o-carboxymethylphenyl)carbamoylmethyl]-6,7-dihydro-1H, 5H-pyrido[1,2,3-de]quinoxaline-2,3-dione Hydrolysis of 9-bromo-5-[(o-methoxycarbonylmethylphenyl)carbamoylmethyl]-6,7-dihydro-1H, 5H-pyrido[1,2,3-de]quinoxaline-2,3-dione (245 mg, 0.5 mmol) was carried out as described in Example 3 to give 200 mg of the title compound (85%): mp 243°~244° C.; $^1$H NMR (270 MHz, DMSO-$d_6$) δ12.07 (bs, 1H), 9.50 (s, 1H), 7.40 (dd, 1H, J=6.8, 2.5 Hz), 7.23~7.28 (m, 3H), 7.13~7.18 (m, 2H), 5.17~5.26 (m, 1H), 3.61 (s, 2H), 3.10 (ddd, 1H, J=17.1, 13.5, 4.5 Hz), 2.83 (dm, 1H, J=17.1 Hz), 2.62 (d, 2H, J=7.3 Hz), 2.13 (dm, 1H, J=13.5 Hz), 1.81~1.94 (m, 1H).

EXAMPLE 123

9-Bromo-5-[(p-tert-butoxycarbonylaminomethylphenyl)carbamoylmethyl]-6,7-dihydro-1H, 5H-pyrido[1,2,3-de]quinoxaline-2,3-dione A procedure similar to that described in Example 5 was carried out with 9-bromo-5-carboxymethyl-6,7-dihydro-1H, 5H-pyrido[1,2,3-de]quinoxaline-2,3-dione (150 mg, 0.44 mmol) and p-tert-butoxycarbonylaminomethylaniline (130 mg, 0.5 mmol) to give 230 mg of the title compound (80%): mp 156°~157° C.; $^1$H NMR (270 MHz, DMSO-$d_6$) δ12.06 (s, 1H), 9.98 (s, 1H), 7.48 (d, 2H, J=8.6 Hz), 7.34 (t, 1H, J=5,7 Hz), 7.24 (bs, 1H), 7.17 (bs, 1H), 7.15 (d, 2H, J=8.6 Hz), 5.16~5.26 (m, 1H), 4.06 (d, 2H, J=5.7 Hz), 3.06 (ddd, 1H, J=17.1, 13.5, 4.5 Hz), 2.83 (dm, 1H, J=17.1 Hz), 2.56~2.65 (m, 2H), 2.10 (dm, 1H, J=13.5 Hz), 1.81~1.96 (m, 1H), 1.39 (s, 9H).

EXAMPLE 124

9-Bromo-5-[(p-aminomethylphenyl)carbamoylmethyl]-6,7-dihydro-1H, 5H-pyrido[1,2,3-de]quinoxaline-2,3-dione hydrochloride To a solution of 9-bromo-5-[(p-tert-butoxycarbonylaminomethylphenyl)carbamoylmethyl]-6,7-dihydro-1H, 5H-pyrido[1,2,3-de]quinoxaline-2,3-dione (180 mg, 0.3 mmol) in THF (6 mL) was added 4N HCl in dioxane (6 mL). The mixture was stirred for 3 h at room temperature and concentrated. The residue was collected by filtration, washed with diethyl ether, and dried in vacuo to give 140 mg of the title compound (97%): mp>270° C.; $^1$H NMR (270 MHz, DMSO-$d_6$) δ12.11 (s, 1H), 10.27 (s, 1H), 8.27 (bs, 2H), 7.61 (d, 2H, J=8.6 Hz), 7.40 (d, 2H, J=8.6 Hz), 7.23 (bs, 1H), 7.20 (bs, 1H), 5.17~5.26 (m, 1H), 3.96 (br, 2H), 3.10 (ddd, 1H, J=17.1, 13.5, 4.5 Hz), 2.83 (dm, 1H, J=17.1 Hz), 2.56~2.71 (m, 2H), 2.09 (dm, 1H, J=13.5 Hz), 1.82~1.96 (m, 1H).

EXAMPLE 125

9-Bromo-5-(1-naphthylcarbamoylmethyl)-6,7-dihydro-1H, 5H-pyrido[1,2,3-de]quinoxaline-2,3-dione A procedure similar to that described in Example 52 was carried out with 9-bromo-5-carboxymethyl-6,7-dihydro-1H, 5H-pyrido[1,2,3-de]quinoxaline-2,3-dione (170 mg, 0.5 mmol) and 1-naphthylamine (150 mg, 1.05 mmol) to give 170 mg of the title compound (73%): mp 171°~172° C. (dec); $^1$H NMR (270 MHz, DMSO-$d_6$) δ12.06 (bs, 1H), 10.02 (s, 1H), 8.01~8.05 (m, 1H), 7.92~7.97 (m, 1H), 7.78 (d, 1H, J=7.9 Hz), 7.70 (d, 1H, J=6.9 Hz), 7.52~7.61 (m, 2H), 7.49 (d, 1H, J=7.6 Hz), 7.28 (s, 1H), 7.20 (s, 1H), 5.26~5.36 (m, 1H), 3.18 (ddd, 1H, J=17.1, 13.5, 4.5 Hz), 2.91 (dm, 1H, J=17.1 Hz), 2.73~2.85 (m, 2H), 2.17~2.29 (m, 1H), 1.89~2.09 (m, 1H).

EXAMPLE 126

9-Bromo-5-(8-quinolylcarbamoylmethyl)-6,7-dihydro-1H, 5H-pyrido[1,2,3-de]quinoxaline-2,3-dione A procedure similar to that described in Example 52 was carried out with 9-bromo-5-carboxymethyl-6,7-dihydro-1H, 5H-pyrido[1,2,3-de]quinoxaline-2,3-dione (170 mg, 0.5 mmol) and 8-aminoquinoline (150 mg, 1.04 mmol) to give 180 mg of the title compound (77%): mp>270° C.; $^1$H NMR (270 MHz, DMSO-$d_6$) δ12.08 (bs, 1H), 10.25 (s, 1H), 8.90 (dd, 1H, J=1.8, 4.5 Hz), 8.61 (d, J=6.6 Hz), 8.41 (d, 8.3 Hz), 7.56 7.70 (m, 3H), 7.24 (s, 1H), 7.18 (s, 1H), 5.25~5.34 (m, 1H), 3.18 (ddd, 1H, J=17.1, 13.5, 4.5 Hz), 3.03 (dd, 1H, J=14.5, 8.9 Hz), 2.78~2.85 (m, 2H), 2.17 (dm, 1H, J=13.5 Hz), 1.85~1.99 (m, 1H).

EXAMPLE 127

9-Bromo-5-(o-carbamoylphenylcarbamoylmethyl)-6,7-dihydro-1H, 5H-pyrido[1,2,3-de]quinoxaline-2,3-dione A procedure similar to that described in Example 52 was carried out with 9-bromo-5-carboxymethyl-6,7-dihydro-1H, 5H-pyrido[1,2,3-de]quinoxaline-2,3-dione (170 mg, 0.5 mmol) and o-carbamoylaniline (75 mg, 0.55 mmol) to give 180 mg of the title compound (79%): mp 186° C. (dec); $^1$H NMR (270 MHz, DMSO-$d_6$) δ12.04 (bs, 1H), 11.64 (s, 1H), 8.38 (d, 1H, J=8.1 Hz), 7.77 (d, 2H, J=8.1 Hz), 7.50 (t, 1H, J=8.1 Hz), 7.21 (s, 1H), 7.14 (s, 1H), 7.12 (t, 1H, J=8.1 Hz), 5.15~5.24 (m, 1H), 3.04 (ddd, 1H, J=17.1, 13.5, 4.5 Hz), 2.83 (dm, 1H, J=17.1 Hz), 2.67 (dd, 1H, J=14.5, 5.0 Hz), 2.61 (dd, 1H, J=14.5, 9.0 Hz), 2.17 (dm, 1H, J=13.5 Hz), 1.81~1.96 (m, 1H).

EXAMPLE 128

9-Bromo-5-(2-benzothiazolylcarbamoylmethyl)-6,7-dihydro-1H, 5H-pyrido[1,2,3-de]quinoxaline-2,3-dione A procedure similar to that described in Example 52 was carried out with 9-bromo-5-carboxymethyl-6,7-dihydro-1H, 5H-pyrido[1,2,3-de]quinoxaline-2,3-dione (170 mg, 0.5 mmol) and 2-aminobenzothiazole (80 mg, 0.53 mmol) to give 180 mg of the title compound (76%): mp 264°~265° C.; $^1$H NMR (270 MHz, DMSO-$d_6$) δ12.46 (bs, 1H), 12.09 (s, 1H), 7.99 (d, 1H, J=7.9 Hz), 7.74 (d, 2H, J=7.9 Hz), 7.44 (dt, 1H, J=1.3, 7.9 Hz), 7.31 (dt, 1H, J=1.3, 7.9 Hz), 7.25 (s, 1H), 7.19 (s, 1H), 5.21~5.31 (m, 1H), 3.04 (ddd, 1H, J=17.1, 13.5, 4.5 Hz), 2.69~2.91 (m, 3H), 2.09 (dm, 1H, J=13.5 Hz), 1.85~1.99 (m, 1H).

EXAMPLE 129

9-Bromo-5-(N,O-dimethyl-N-hydroxycarbamoylmethyl)-6,7-dihydro-1H, 5H-pyrido-[1,2,3-de]quinoxaline-2,3-dione A procedure similar to that described in Example 5 was carried out with 9-bromo-5-carboxymethyl-6,7-dihydro-1H, 5H-pyrido[1,2,3-de]quinoxaline-2,3-dione (340 mg, 1 mmol) and N,O-dimethylhydroxylamine hydrochloride (120 mg, 1.23 mmol) to give 170 mg of the title compound (55%) after extractive work-up with ethyl acetate: mp 231° C.; $^1$H NMR (270 MHz, DMSO-$d_6$) δ12.05 (bs, 1H), 7.20 (s, 1H), 7.16 (s, 1H), 5.10~5.17 (m, 1H), 3.62 (s, 3H), 3.10 (s, 3H), 2.96 (ddd, 1H, J=17.1, 13.5, 4.5 Hz), 2.80 (dm, 1H, J=17.1 Hz), 2.60~2.74 (m, 2H), 2.15 (dm, 1H, J=13.5 Hz), 1.79~1.94 (m, 1H).

EXAMPLE 130

9-Bromo-5-{[p-2-methoxycarbonyl-(E)-ethenylphenyl]carbamoylmethyl}-6,7-dihydro-1H, 5H-pyrido[1,2,3-de]quinoxaline-2,3-dione A procedure similar to that described in Example 52 was carried out with 9-bromo-5-carboxymethyl-6,7-dihydro-1H, 5H-pyrido[1,2,3-de]quinoxaline-2,3-dione (340 mg, 1 mmol) and p-[2-methoxycarbonyl-(E)-ethenyl]aniline (185 mg, 1.05 mmol) to give 410 mg of the title compound (82%): 166°~167° C. (dec); $^1$H NMR (270 MHz, DMSO-$d_6$) δ12.08 (s, 1H), 10.25 (s, 1H), 7.69 (d, 2H, J=8.6 Hz), 7.64 (d, 2H, J=8.6 Hz), 7.62 (d, 1H, J=16.2 Hz), 7.24 (bs, 1H), 7.18 (bs, 1H), 6.54 (d, 1H, J=16.2 Hz), 5.18~5.27 (m, 1H), 3.72 (s, 3H), 3.06 (ddd, 1H, J=17.1, 13.5, 4.5 Hz), 2.83 (dm, 1H, J=17.1 Hz), 2.63 (d, 2H, J=7.3 Hz), 2.10 (dm, 1H, J=13.5 Hz), 1.82~1.96 (m, 1H).

EXAMPLE 131

9-Bromo-5-{[p-2-carboxy-(E)-ethenylphenyl]carbamoylmethyl}-6,7-dihydro-1H, 5H-pyrido[1,2,3-de]quinoxaline-2,3-dione Hydrolysis of 9-bromo-5-{[p-2-methoxycarbonyl-(E)-ethenylphenyl]carbamoylmethyl}-6,7-dihydro-1H, 5H-pyrido[1,2,3-de]quinoxaline-2,3-dione (280 mg, 0.56 mmol) was carried out as described in Example 3 to give 250 mg of the title compound (89%): mp 242°~243° C.; $^1$H NMR (270 MHz, DMSO-$d_6$) δ12.08 (s, 1H), 10.23 (s, 1H), 7.59~7.66 (m, 4H), 7.53 (d, 1H, J=15.8 Hz), 7.24 (d, 1H, J=2 Hz), 7.18 (d, 1H, J=2 Hz), 6.42 (d, 1H, J=15.8 Hz), 5.17~5.25 (m, 1H), 3.05 (ddd, 1H, J=17.1, 13.5, 4.5 Hz), 2.83 (dm, 1H, J=17.1 Hz), 2.63 (d, 2H, J=7.3 Hz), 2.10 (dm, 1H, J=13.5 Hz), 1.81~1.94 (m, 1H).

EXAMPLE 132

9-Chloro-5-methoxycarbonylmethyl-6,7-dihydro-1H, 5H-pyrido[1,2,3-de]quinoxaline-2,3-dione A mixture of 9-bromo-5-methoxycarbonylmethyl-6,7-dihydro-1H, 5H-pyrido[1,2,3-de]quinoxaline-2,3-dione (530 mg, 1.50 mmol) and cuprous chloride (1.0 g, 10.1 mmol) in dimethyl sulfoxide (5 mL) was heated at 160° C. for 4.5 h and poured into 1N aqueous ammonium chloride (200 mL). The mixture was extracted with a mixed solvent of THF and ethyl acetate (600 mL). The extract was washed with 1N aqueous ammonium chloride (200 mL×2) and brine (200 mL), dried over magnesium sulfate, and concentrated. The residue was recrystallized from ethanol to give 125 mg of the title compound (27%): mp 218°~220° C. (dec); $^1$H NMR (270 MHz, DMSO-$d_6$) δ12.08 (bs, 1H), 7.08 (d, 1H, J=2 Hz), 7.02 (d, 1H, J=2 Hz), 5.04~5.13 (m, 1H), 3.62 (s, 3H), 2.94 (ddd, 1H, J=17.1, 13.5, 4.5 Hz), 2.78 (dm, 1H, J=17.1 Hz), 2.63 (dd, 1H, J=18, 7.2 Hz), 2.57 (dd, 1H, J=18, 3.6 Hz), 2.09 (dm, 1H, J=13.5 Hz), 1.80~1.95 (m, 1H).

EXAMPLE 133

9-Chloro-5-carboxymethyl-6,7-dihydro-1H, 5H-pyrido[1,2,3-de]quinoxaline-2,3-dione Hydrolysis of 9-chloro-5-methoxycarbonylmethyl-6,7-dihydro-1H, 5H-pyrido[1,2,3-de]quinoxaline-2,3-dione (246 mg, 0.8 mmol) was carried out as described in Example 3 to give 210 mg of the title compound (89%): mp>280° C.; $^1$H NMR (270 MHz, DMSO-$d_6$) δ12.06 (bs, 1H), 7.08 (d, 1H, J=2 Hz), 7.02 (d, 1H, J=2 Hz), 5.02~5.13 (m, 1H), 2.95 (ddd, 1H, J=17.1, 13.5, 4.5 Hz), 2.78 (dm, 1H, J=17.1 Hz), 2.41~2.60 (m, 2H), 2.14 (dm, 1H, J=13.5 Hz), 1.88~1.95 (m, 1H).

EXAMPLE 134

9-Chloro-5-phenylcarbamoylmethyl-6,7-dihydro-1H, 5H-pyrido[1,2,3-de]quinoxaline-2,3-dione A procedure similar to that described in Example 5 was carried out with 9-chloro-5-carboxymethyl-6,7-dihydro-1H, 5H-pyrido[1,2,3-de]quinoxaline-2,3-dione (200 mg, 0.68 mmol) and aniline (200 mg, 2.15 mmol) to give 150 mg of the title compound (60%):mp >280° C.; $^1$H NMR (270 MHz, DMSO-$d_6$) δ12.09 (bs, 1H), 10.02 (s, 1H), 7.57 (d, 2H, J=7.8 Hz), 7.30 (t, 2H, J=7.8 Hz), 7.14 (s, 1H), 7.06 (t, 1H, J=7.8 Hz), 7.05 (s, 1H), 5.14~5.29 (m, 1H), 3.06 (ddd, 1H, J=17.1, 13.5, 4.5 Hz), 2.82 (dm, 1H, J=17.1 Hz), 2.55~2.70 (m, 2H), 2.10 (dm, 1H, J=13.5 Hz), 1.80~1.96 (m, 1H).

EXAMPLE 135

9-Cyano-5-methoxycarbonylmethyl-6,7-dihydro-1H, 5H-pyrido[1,2,3-de]quinoxaline-2,3-dione A mixture of 9-bromo-5-methoxycarbonylmethyl-6,7-dihydro-1H, 5H-pyrido[1,2,3-de]quinoxaline-2,3-dione (530 mg, 1.50 mmol) and cuprous cyanide (890 mg, 9.9 mmol) in dimethyl sulfoxide (5 mL) was heated at 180° C. for 8.5 h and poured into 1N aqueous ammonium chloride (200 mL). The mixture was extracted with a mixed solvent of THF and ethyl acetate (600 mL). The extract was washed with 1N aqueous ammonium chloride (200 mL×2) and brine (200 mL), dried over magnesium sulfate, and concentrated. The residue was rinsed with dichloromethane to give 176 mg of the title compound (39%): mp 255°~258° C. (dec); $^1$H NMR (270 MHz, DMSO-$d_6$) δ12.22 (bs, 1H), 7.47 (d, 1H, J=2 Hz), 7.31 (d, 1H, J=2 Hz), 5.02~5.16 (m, 1H), 3.63 (s, 3H), 2.95 (ddd, 1H, J=17.1, 13.5, 4.5 Hz), 2.85 (dm, 1H, J=17.1 Hz), 2.55~2.72 (m, 2H), 2.15 (dm, 1H, J=13.5 Hz), 1.80~1.98 (m, 1H).

EXAMPLE 136

9-Cyano-5-carboxymethyl-6,7-dihydro-1H, 5H-pyrido[1,2,3-de]quinoxaline-2,3-dione Hydrolysis of 9-cyano-5-methoxycarbonylmethyl-6,7-dihydro-1H, 5H-pyrido[1,2,3-de]quinoxaline-2,3-dione (150 mg, 0.5 mmol) was carried out as described in Example 3 to give 105 mg of the title compound (73%): mp 227°~229° C. (dec); $^1$H NMR (270 MHz, DMSO-$d_6$) δ12.48 (br, 1H), 12.20 (bs, 1H), 7.47 (s, 1H), 7.31 (s, 1H), 5.03~5.16 (m, 1H), 2.98 (ddd, 1H, J=17.1, 13.5, 4.5 Hz), 2.84 (dm, 1H, J=17.1 Hz), 2.43~2.63 (m, 2H), 2.16 (dm, 1H, J=13.5 Hz), 1.80~1.96 (m, 1H).

EXAMPLE 137

9-Cyano-5-phenylcarbamoylmethyl-6,7-dihydro-1H, 5H-pyrido[1,2,3-de]quinoxaline-2,3-dione A procedure similar to that described in Example 5 was carried out with 9-cyano-5-carboxymethyl-6,7-dihydro-1H, 5H-pyrido[1,2,3-de]quinoxaline-2,3-dione (70 mg, 0.245 mmol) and aniline (70 mg, 0.75 mmol) to give 60 mg of the title compound (68%): mp 171°~176° C. (dec); $^1$H NMR (270 MHz, DMSO-$d_6$)δ12.22 (bs, 1H), 10.02 (s, 1H), 7.56 (d, 2H, J=7.8 Hz), 7.52 (s, 1H), 7.33 (s, 1H), 7.30 (t, 2H, J=7.8 Hz), 7.05 (t, 1H, J=7.8 Hz), 5.18~5.29 (m, 1H), 3.08 (ddd, 1 H, J=17.1, 13.5, 4.5 Hz), 2.87 (dm, 1H, J=17.1 Hz), 2.54~2.70 (m, 2H), 2.12 (dm, 1H, J=13.5 Hz), 1.80~1.97 (m, 1H).

EXAMPLE 138

9-Iodo-5-methoxycarbonylmethyl-6,7-dihydro-1H, 5H-pyrido[1,2,3-de]quinoxaline-2,3-dione A mixture of 9-bromo-5-methoxycarbonylmethyl-6,7-dihydro-1H, 5H-pyrido[1,2,3-de]quinoxaline-2,3-dione (530 mg, 1.50 mmol), potassium iodide (4.98 g, 30 mmol) and cuprous iodide (2.0 g, 10.5 mmol) in hexamethylphosphoric triamide (5 mL) was heated at 160° C. for 6.5 h and poured into 1N aqueous ammonium chloride (200 mL). The mixture was extracted with a mixed solvent of THF and ethyl acetate (600 mL). The extract was washed with 1N aqueous ammonium chloride (200 mL×2) and brine (200 mL), dried over magnesium sulfate, and concentrated. The residue was purified by silica gel column chromatography with 0.7 to 1% acetic acid/ethyl acetate to give 465 mg of the title compound (78%): mp 241°~243° C.; $^1$H NMR (270 MHz, DMSO-$d_6$) δ12.01 (bs, 1H), 7.33 (s, 1H), 7.31 (s, 1H), 5.03~5.14 (m, 1H), 3.62 (s, 3H), 2.93 (ddd, 1H, J=17.1, 13.5, 4.5 Hz), 2.78 (dm, 1H, J=17.1 Hz), 2.54~2.69 (m, 2H), 2.09 (dm, 1H, J=13.5 Hz), 1.79~1.96 (m, 1H).

EXAMPLE 139

9-Iodo-5-carboxymethyl-6,7-dihydro-1H, 5H-pyrido[1,2,3-de]quinoxaline-2,3-dione

Hydrolysis of 9-iodo-5-methoxycarbonylmethyl-6,7-dihydro-1H, 5H-pyrido[1,2,3-de]quinoxaline-2,3-dione (35 mg, 0.087 mmol) was carried out as described in Example 3 to give 24 mg of the title compound (71%): mp 178°~181° C. (dec); $^1$H NMR (270 MHz, DMSO-$d_6$) δ11.99 (bs, 1H), 7.33 (s, 1H), 7.31 (s, 1H), 5.00~5.10 (m, 1H), 2.92 (ddd, 1H, J=17.1, 13.5, 4.5 Hz), 2.77 (dm, 1H, J=17.1 Hz), 2.40~2.60 (m, 2H), 2.11 (dm, 1H, J=13.5 Hz), 1.78~1.94 (m, 1H).

EXAMPLE 140

5-Methoxycarbonylmethyl-9-nitro-6,7-dihydro-1H, 5H-pyrido[1,2,3-de]quinoxaline- 2,3-dione 1) 5-Methoxycarbonylmethyl-6,7-dihydro-1H, 5H-pyrido [1,2,3-de]quinoxaline-2,3-dione 9-Bromo-5-methoxycarbonylmethyl-6,7-dihydro-1H, 5H-pyrido[1,2,3-de]quinoxaline-2,3-dione (1.15 g, 3.26 mmol) in a mixture of THF (5 mL), DMF (10 mL), and acetic acid (8 mL) was hydrogenated over palladium on carbon (300 mg) under atmospheric pressure of hydrogen at room temperature for 5 h. The mixture was passed through celite and concentrated. The residue was purified by silica gel column chromatography with ethyl acetate to give 700 mg of 5-methoxycarbamoylmethyl-6,7-dihydro-1H, 5H-pyrido[1,2,3-de]-quinoxaline-2,3-dione (79%): 227°–229° C. (dec); $^1$H NMR (270 MHz, DMSO-$d_6$) δ12.00 (bs, 1H), 6.97–7.12 (m, 2H), 5.06–5.16 (m, 1H), 3.63 (s, 3H), 2.97 (ddd, 1H, J=17.1, 13.5, 4.5 Hz), 2.79 (dm, 1H, J=17.1 Hz), 2.54–2.69 (m, 2H), 2.12 (dm, 1H, J=13.5 Hz), 1.82–2.00 (m, 1H).

2) 5-Methoxycarbonylmethyl-9-nitro-6,7-dihydro-1H, 5H-pyrido[1,2,3-de]quinoxaline-2,3-dione To a solution of 5-methoxycarbonylmethyl-6,7-dihydro-1H, 5H-pyrido[1,2,3-de]quinoxaline-2,3-dione (66 mg, 0.24 mmol) in concentrated sulfuric acid (1.5 mL) was added isopropyl nitrate (30 μL, 0.3 mmol) at 0° C. The mixture was stirred for 45 min at 0° C., poured into ice-water, and extracted with ethyl acetate (100 mL×2). The extracts were washed with brine, dried over magnesium sulfate, and concentrated. The residue was purified by silica gel column chromatography with 0.1% acetic acid/ethyl acetate to give 33 mg of the title compound (43%): mp 254°–256° C.; $^1$H NMR (270 MHz, DMSO-$d_6$) δ12.23 (bs, 1H), 7.91 (d, 1H, J=2.6 Hz), 7.85 (d, 1H, J=2.6 Hz), 5.05–5.21 (m, 1H), 3.64 (s, 3H), 2.85–3.10 (m, 2H), 2.56–2.72 (m, 2H), 2.17 (dm, 1H, J=13.5 Hz), 1.80–2.00 (m, 1H).

EXAMPLE 141

9-Bromo-6,7-dihydro-1H, 5H-pyrido[1,2,3-de]quinoxaline-2,3-dione

The title compound was prepared by the route outlined in Example 1 starting with tetrahydroquinoline: mp>280° C.; $^1$H NMR (270 MHz, DMSO-$d_6$) δ12.0 (bs, 1H), 7.17 (d, 1H, J=1Hz), 7.12 (d, 1H, J=1Hz), 3.91 (t, 2H, J=5 Hz), 2.84 (t, 2H, J=5 Hz), 1.96 (5 et, 2H, J=5 Hz).

EXAMPLE 142

9-Bromo-5-cyanomethyl-6,7-dihydro-1H, 5H-pyrido [1,2,3-de]quinoxaline-2,3-dione

A mixture of 9-bromo-5-iodomethyl-6,7-dihydro-1H, 5H-pyrido[1,2,3-de]quinoxaline-2,3-dione (Example 36) (632 mg, 1.5 mmol) and sodium cyanide (147 mg, 3 mmol) in DMF (5 mL) was heated at 40° C. for 14.5 h. The mixture was poured into water, acidified by addition of 1N aqueous hydrochloric acid, and extracted with ethyl acetate. The organic layer was washed with brine, dried over magnesium sulfate, and concentrated. The residue was purified by silica gel column chromatography with ethyl acetate to 1% acetic acid/ethyl acetate to give 117 mg of the title compound (24%): mp>280° C.; $^1$H NMR (270 MHz, DMSO-$d_6$) δ12.10 (bs, 1H), 7.23 (s, 1H), 7.16 (s, 1H), 4.97–5.07 (m, 1H), 2.74–3.10 (m, 4H), 2.20 (dm, 1H, J=13.5 Hz), 1.87–2.03 (m, 1H).

EXAMPLE 143

9-Bromo-5-formyl-6,7-dihydro-1H, 5H-pyrido[1,2,3-de]quinoxaline-2,3-dione

A mixture of 9-bromo-5-hydroxymethyl-6,7-dihydro-1H, 5H-pyrido[1,2,3-de]quinoxaline-2,3-dione (520 mg, 1.67 mmol) and Dess-Martin periodinane (945 mg, 2.27 mmol) in THF (140 mL) was stirred for 5 h at room temperature. The excess reagent was decomposed by addition of ethanol and the resulting mixture was concentrated. The residual solids were triturated with dichloromethane and the insoluble materials were removed by filtration. The filtrate was concentrated and the residue was purified by silica gel column chromatography with 0.2% acetic acid/ethyl acetate to give 330 mg of the title compound (64%): $^1$H NMR (270 MHz, DMSO-$d_6$) δ12.30 (bs, 1H), 9.57 (s, 1H), 7.21 (d, 1H, J=2 Hz), 7.19 (d, 1H, J=2 Hz), 5.31–5.37 (m, 1H), 2.85 (dm, 1H, J=15.8 Hz), 2.45–2.68 (m, 2H), 1.92–2.10 (m, 1H).

EXAMPLE 144

9-Bromo-5-benzylaminomethyl-6,7-dihydro-1H, 5H-pyrido[1,2,3-de]quinoxaline-2,3-dione hydrochloride To a solution of 9-bromo-5-formyl-6,7-dihydro-1H, 5H-pyrido[1,2,3-de]quinoxaline-2,3-dione (154 mg, 0.5 mmol) and benzylamine hydrochloride (79 mg, 0.55 mmol)in methanol (3 mL) was added sodium cyanoborohydride (100 mg, 1.6 mmol) by portions at 0° C. The mixture was stirred for 4.5 h at 0° C. ~ room temperature and poured into 1/15M phosphate buffer (pH 7.4, 50 mL). The precipitates formed were collected by filtration and dried in vacuo. The solids were dissolved in dichloromethane and saturated hydrogen chloride in isopropanol was added. The resulting mixture was concentrated and the residual solid was rinsed with dichloromethane to give 90 mg of the title compound (41%): $^1$H NMR (270 MHz, DMSO-$d_6$) δ12.13 (bs, 1H), 9.13 (s, 1H), 9.09 (s, 1H), 7.40–7.59 (m, 5H), 7.24 (d, 1H, J=2 Hz), 7.20 (d, 1H, J=2 Hz), 5.33–5.23 (m, 1H), 4.20 (d, 1H, J=13.0 Hz), 4.10 (d, 1H, J=13.0 Hz), 3.18–3.29 (m, 2H), 2.73–2.99 (m, 2H), 2.27 (dm, 1H, J=12.9 Hz), 1.77–2.00 (m, 1H).

We claim:

1. A tricyclic quinoxalinedione represented by the formula:

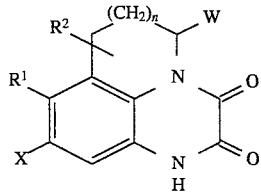

wherein

X represents alkyl, halogen, cyano, trifluoromethyl, nitro, hydroxy, amino, alkylamino, alkoxy, alkanoyl, alkoxycarbonyl, sulfamoyl, carbamoyl, alkylcarbamoyl, alkylthio, alkylsulfinyl, alkylsulfonyl, alkylsulfamoyl, alkylsulfonylamino, or acylamino;

$R^1$ represents hydrogen, alkyl, halogen, cyano, trifluoromethyl, nitro, hydroxy, amino, alkylamino, alkoxy, alkanoyl, alkoxycarbonyl, sulfamoyl, carbamoyl, alkylcarbamoyl, alkylthio, alkylsulfinyl, alkysulfonyl, alkylsulfamoyl, alkylsulfonylamino, or acylamino;

$R^2$ represent hydrogen, alkyl, cycloalkyl, alkenyl, alkynyl, cycloalkylalkyl, arylalkyl, substituted arylalkyl, aryl, or substituted aryl;

W represents hydrogen, $CO_2R^3$, $CO_2Y$, $CONR^3R^4$, $CONR^3Y$, $CON(OR^3)R^4$, $COR^3$, CN, tetrazolyl, or substituted alkyl;

$R^3$ and $R^4$ independently represent hydrogen, alkyl, cycloalkyl, alkenyl, alkynyl, cycloalkylalkyl, arylalkyl, substituted arylalkyl, aryl, substituted aryl, heteroarylalkyl, heteroaryl, substituted heteroaryl, substituted heteroarylalkyl or heterocyclic;

Y represents mono-substituted alkyl or di substituted alkyl; and n is an integer 0 or 1; or a pharmaceutically acceptable salt thereof; and wherein, the term "alkyl" as used herein means alkyl groups containing from 1 to 6 carbon atoms; the term "alkoxy" as used herein means alkoxy groups containing from 1 to 6 carbon atoms; the term "alkanoyl" as used herein means alkanoyl groups containing from 1 to 6 carbon atoms; the term "alkoxycarbonyl" used herein means alkoxycarbonyl groups containing from 2 to 6 carbon atoms; the term "alkylthio" as used herein means alkylthio groups containing from 1 to 6 carbon atoms; the term "alkylsulfinyl" as used herein means alkylsulfinyl groups containing from 1 to 6 carbon atoms; the term "alkylsulfonyl" as used herein means alkylsulfonyl groups containing from 1 to 6 carbon atoms; the term "alkylcarbamoyl" as used herein means mono- or dialkylcarbamoyl, wherein an alkyl moiety contains from 1 to 6 carbon atoms; the term "alkylsulfamoyl" as used herein means sulfamoyl groups substituted with 1 or 2 alkyl groups containing from 1 to 6 carbon atoms; the term "alkylsulfonylamino" as used herein means alkylsulfonylamino groups containing from 1 to 6 carbon atoms; the term "acylamino" as used herein means alkanoylamino groups containing from 1 to 6 carbon atoms, or the term "acylamino" means aroylamino groups containing from 7 to 11 carbon atoms; the term "cycloalkyl" as used herein means cycloalkyl groups containing from 3 to 7 carbon atoms; the term "alkenyl" as used herein means alkenyl groups containing from 2 to 6 carbon atoms; the term "alkynyl" as used herein means alkynyl groups containing from 2 to 6 carbon atoms; the term "cycloalkylalkyl" as used herein means alkyl groups attached to cycloalkyl groups, said cycloalkylalkyl containing up to 13 carbon atoms; the term "arylalkyl" as used herein means alkyl groups attached to aryl groups, said alkylaryl containing up to 15 carbon atoms; the term "aryl" as used herein means aryl groups containing up to 10 carbon atoms; the term "heteroaryl" as used herein means 5 or 6 membered heteroaryl groups containing up to 4 nitrogen atoms and the rest carbon atoms, or the term "heteroaryl" means 5 or 6 membered heteroaryl groups containing up to 2 nitrogen atoms, up to 1 oxygen atom or up to 1 sulfur atom and the rest carbon atoms, or the term "heteroaryl" means 5 or 6 membered heteroaryl groups containing up to 3 nitrogen atoms, up to 1 oxygen atom or 1 sulfur atom and the rest carbon atoms which are fused with a benzene ring; the term "heteroarylalkyl" as used herein means alkyl groups containing up to 6 carbon atoms which are attached to a heteroaryl group, wherein the heteroaryl group is as defined above; the term "heterocyclic" as used herein means heterocyclic groups containing up to 6 carbon atoms together with 1 or 2 heteroatoms which are selected from nitrogen, oxygen, and sulfur atoms, or the term "heterocyclic" means a heterocyclic group fused with a benzene-ring wherein the fused rings contain carbon atoms together with 1 or 2 heteroatoms which are selected from nitrogen, oxygen and sulfur atoms; the term "alkylamino" as used herein means mono- or dialkylamino groups, wherein the alkyl groups thereof contain from 1 to 6 carbon atoms; the alkyl groups of both of the terms "substituted alkyl" as used in W and "mono-substituted alkyl" as used in Y mean alkyl groups containing from 1 to 4 carbon atoms; the substituent of the term "substituted alkyl" as used in W means $CO_2R^3$, $CO_2Y$, $CONR^3R^4$, $CONR^3Y$, $CON(OR^3)R^4$, $COR^3$, $CN$, $NR^3CO_2R^4$, $NR^3CONR^4R^5$, phthalimido, heteroaryl, substituted heteroaryl, heterocyclic, $NR^3R^4$, $NR^3SO_2R^4$, $NR^3COR^4$, $NR^3COY$, $NR^3COCO_2R^4$, $NR^3COCONR^4R^5$, $NR^3COCOR^4$, $OR^3$, $OC(O)R^3$, $O-C-(O)Y$, $OCO_2R^3$, $O-CONR^3R^4$, $O-COCO_2R^3$, $O-COCOR^3$, $O-COCONR^3R^4$, $OSO_2R^3$, $PO(OR^3)_2$, $SR^3$, $SOR^3$, $SO_2R^3$, $SO_3R^3$, $SO_2NR^3R^4$, Cl, Br, or I, wherein $R^5$ represents hydrogen, alkyl, cycloalkyl, alkenyl, alkynyl, cycloalkylalkyl, arylalkyl, substituted arylalkyl, aryl, substituted aryl, heteroarylalkyl, heteroaryl, substituted heteroaryl, substituted heteroarylalkyl or heterocyclic, and $R^3$, $R^4$ and Y are the same as defined above; the substituent of the term "mono-substituted alkyl" as used in Y means $CO_2R^3$, $CONR^3R^4$, $COR^3$, $CN$, $NR^3CO_2R^4$, $NR^3CONR^4R^5$, phthalimido, $NR^3R^4$, $NR^3SO_2R^4$, $NR^3COR^4$, $OR^3$, $O-COR^3$, $OCO_2R^3$ or $O-CONR^3R^4$, wherein $R^3$, $R^4$ and $R^5$ are the same as defined above; the alkyl groups of the term "di-substituted alkyl" as used in Y mean straight-chained alkyl groups containing from 1 to 4 carbon atoms; the substituents of the term "di-substituted alkyl" as used in Y independently mean $CO_2R^3$, $CONR^3R^4$, $COR^3$, CN, $NR^3CO_2R^4$, $NR^3CONR^4R^5$, phthalimido, aryl, substituted aryl, heteroaryl, substituted heteroaryl, heterocyclic, $NR^3R^4$, $NR^3SO_2R^4$, $NR^3COR^4$, $OR^3$, $O-COR^3$, $OCO_2R^3$ or $O-CONR^3R^4$, wherein $R^3$, $R^4$ and $R^5$ are the same as defined above; the number of substituents of the terms "substituted aryl," "substituted arylalkyl," "substituted heteroaryl" or "substituted heteroarylalkyl", as respectively used herein is 1 to 3, with said substituents being selected from the group consisting of alkyl, halogen, cyano, trifluoromethyl, nitro, hydroxy, mercapto, amino, alkylamino, alkoxy, alkanoyl, alkoxycarbonyl, carboxy, sulfamoyl, carbamoyl, alkylcarbamoyl, alkylthio, alkylsulfinyl, alkylsulfonyl, alkylsulfamoyl, alkylsulfonylamino, acylamino, substituted alkyl, substituted alkenyl and substituted alkynyl, wherein the alkyl group of the term "substituted alkyl" means alkyl groups containing from 1 to 4 carbon atoms, the substituent of the term "substituted alkyl" is selected from the group consisting of amino, alkylamino, alkoxycarbonyl, carboxy and carbamoyl, the alkenyl group of the term "substituted alkenyl" means alkenyl groups containing 2 to 5 carbon atoms, the substituent of the term "substituted alkenyl" means amino, alkylamino, alkoxycarbonyl, carboxy or carbamoyl, the alkynyl group of the term "substituted alkynyl" means alkynyl groups containing from 2 to 5 carbon atoms, and the substituent of the term "substituted alkynyl" means amino, alkylamino, alkoxycarbonyl, carboxy, or carbamoyl.

2. A compound according to claim 1, wherein W is a carboxyl group or a substituted methyl group, wherein the substituent is the same as defined for that of substituted alkyl in claim 1.

3. A compound according to claim 1, wherein n is 1.

4. A compound according to claim 2, wherein a substituent of the substituted methyl group is a member selected from the group consisting of $CO_2R^3$, $CONR^3R^4$, $CON(OR^3)R^4$, and $NR^3COR^4$, wherein $R^3$ and $R^4$ are as defined in claim 1.

5. A compound according to claim 3, wherein $R^2$ is attached to said compound's C-6 position.

6. A pharmaceutical composition comprising a pharmaceutically effective amount of a compound as set forth in claim 1, or a pharmaceutically acceptable salt thereof, in admixture with a pharmaceutically acceptable carrier or diluent.

7. A method for treating epilepsy in a patient, which comprises:

administering to said patient a pharmaceutically effective amount of a compound as set forth in claim 1, or a pharmaceutically acceptable salt thereof.

* * * * *